United States Patent
Segura et al.

(10) Patent No.: US 7,029,697 B2
(45) Date of Patent: *Apr. 18, 2006

(54) CONTROLLED SURFACE-ASSOCIATED DELIVERY OF GENES AND OLIGONUCLEOTIDES

(75) Inventors: Tatiana Segura, Evanston, IL (US); Lonnie D. Shea, Evanston, IL (US); Angela Kaye Pannier, Glenview, IL (US); Zain Bengali, Naperville, IL (US); Jae-Hyung Jang, Skokie, IL (US); Peter Chung, Montgomery, AL (US); Brian C. Anderson, Libertyville, IL (US)

(73) Assignee: Northwestern University, Evanston, IL (US)

(*) Notice: Subject to any disclaimer, the term of this patent is extended or adjusted under 35 U.S.C. 154(b) by 17 days.

This patent is subject to a terminal disclaimer.

(21) Appl. No.: 10/893,572

(22) Filed: Jul. 15, 2004

(65) Prior Publication Data

US 2005/0090008 A1  Apr. 28, 2005

Related U.S. Application Data

(63) Continuation-in-part of application No. 10/076,060, filed on Feb. 14, 2002, now Pat. No. 6,890,556.

(60) Provisional application No. 60/268,626, filed on Feb. 14, 2001.

(51) Int. Cl.
*A61K 9/127* (2006.01)

(52) U.S. Cl. .................. 424/450; 435/458; 435/320.1; 536/23.1

(58) Field of Classification Search ............... 424/450; 435/458, 320.1; 536/23.1
See application file for complete search history.

(56) References Cited

U.S. PATENT DOCUMENTS

| 6,312,727 | B1 | 11/2001 | Schacht et al. |
| 6,544,790 | B1 * | 4/2003 | Sabatini ............ 435/455 |
| 2002/0197720 | A1 | 12/2002 | Uhler |
| 2003/0077824 | A1 | 4/2003 | Uhler |

OTHER PUBLICATIONS

Zheng et al., Biotechnol. Prog., vol. 16, 2000, pp. 254-257.*
Adami, et al., J. Pharm. scl., 87:678-683 (1998).
Bonadio, et al., Nat. Med., 5:753-759 (1999).
Bielinska, et al., Biomaterials, 21:877-887 (2000).
Bielinska, et al., Biochem. Biophys. Acta, 1353:180-190 (1997).
Duguid, et al., Biophys J., 74:2802-2814 (1998).
Fischer, et al., Pharm. Res., 16:1273-1279 (1999).
Gao, et al., Biochemistry, 35:1027-1036 (1996).
Luo, et al., Nat. Biotechnol. 18:893-895 (2000).
Shea, et al., Nat. Biotechnol., 17:551-554 (1999).
Vitiello, et al., Gene Ther., 3:396-404 (1996).
Zheng, et al., Biotechnol. Prog., 16:254-257 (2000).

* cited by examiner

*Primary Examiner*—James Ketter
(74) *Attorney, Agent, or Firm*—Klauber & Jackson

(57) ABSTRACT

A system and methods for controlled gene delivery comprising condensed nucleic acids complexed with polylinkers, wherein the complexes are covalently and/or non-covalently bound to the surface of a substrate capable of supporting cell adhesion. The gene delivery system achieves temporal and spatial control of nucleic acid delivery to a target cell or cells through control of complex density on the surface of the support substrate, and reversibility of the attachment of the polylinker to the support substrate. The system and method of the invention can be used to create spatial patterns of gene expression, and in tissue engineering, high throughput screening, and gene therapy applications.

26 Claims, 30 Drawing Sheets

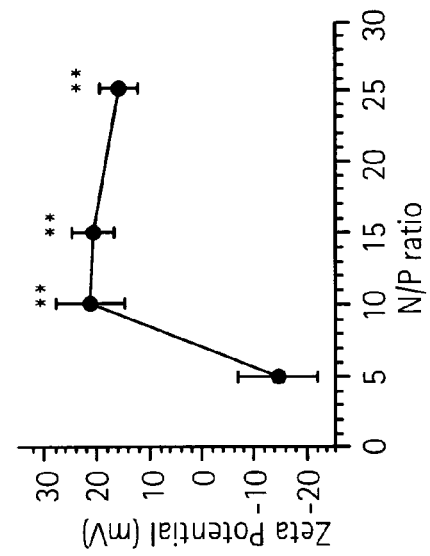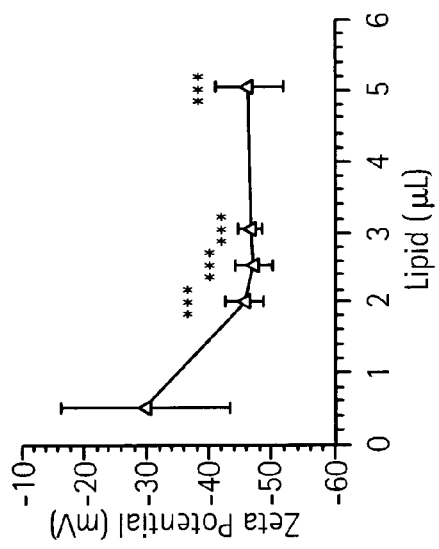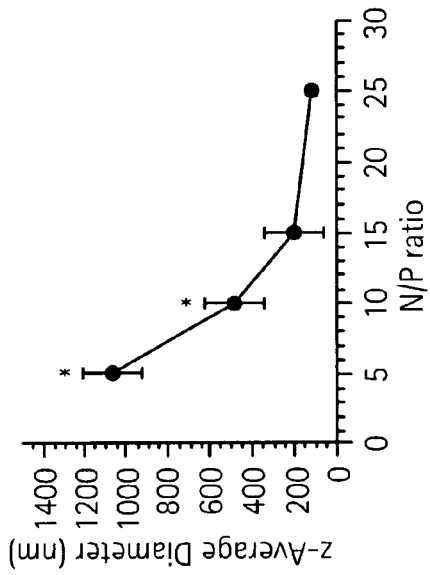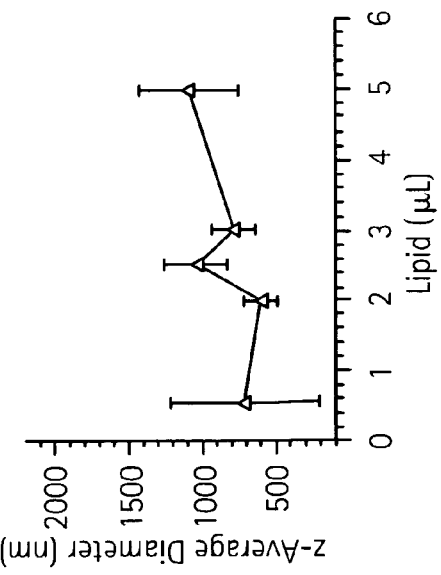

FIG. 23A
FIG. 23B
FIG. 23C
FIG. 23D
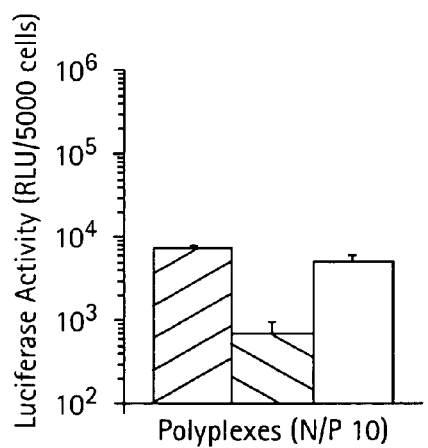
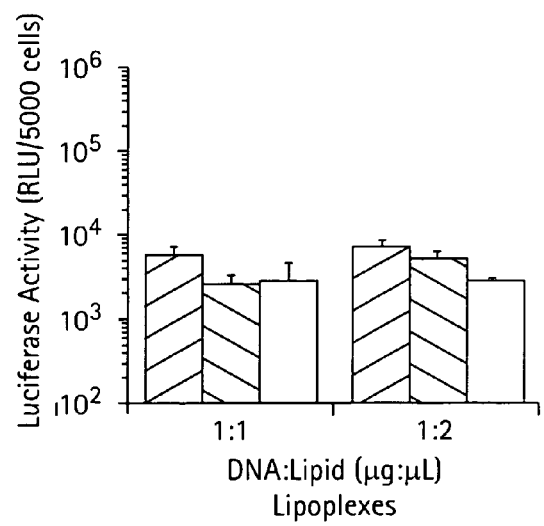

FIG. 27A
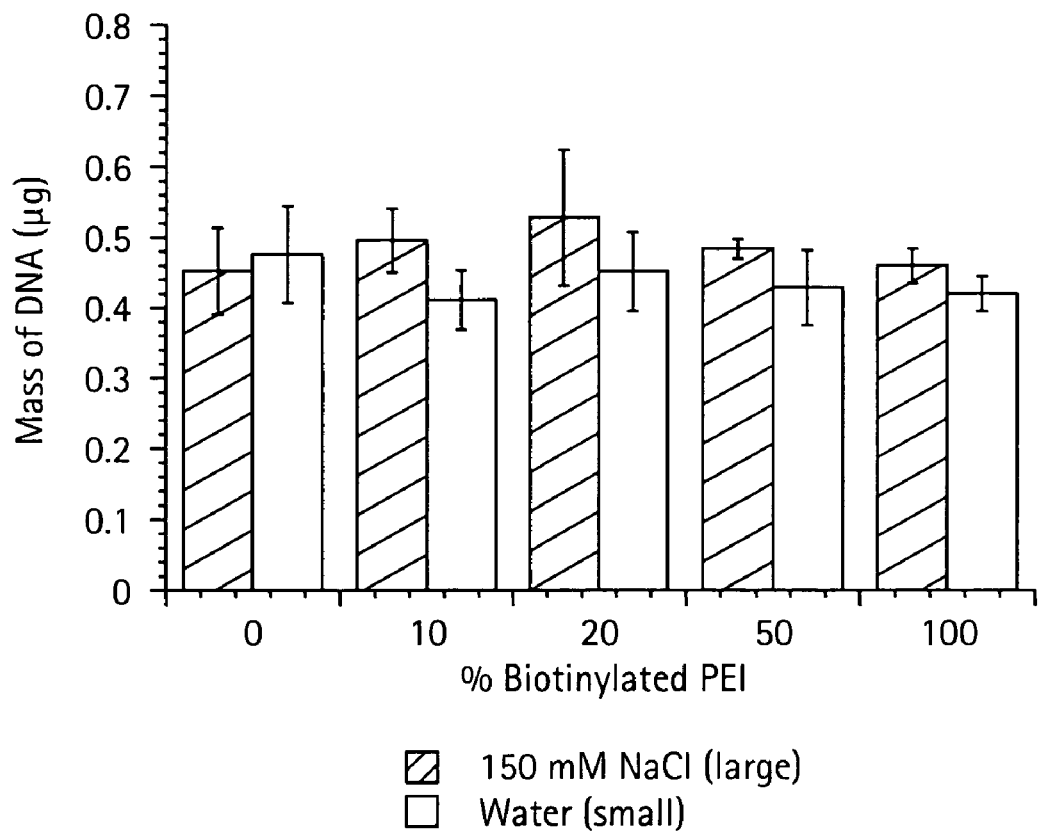
FIG. 27B    FIG. 27C
  

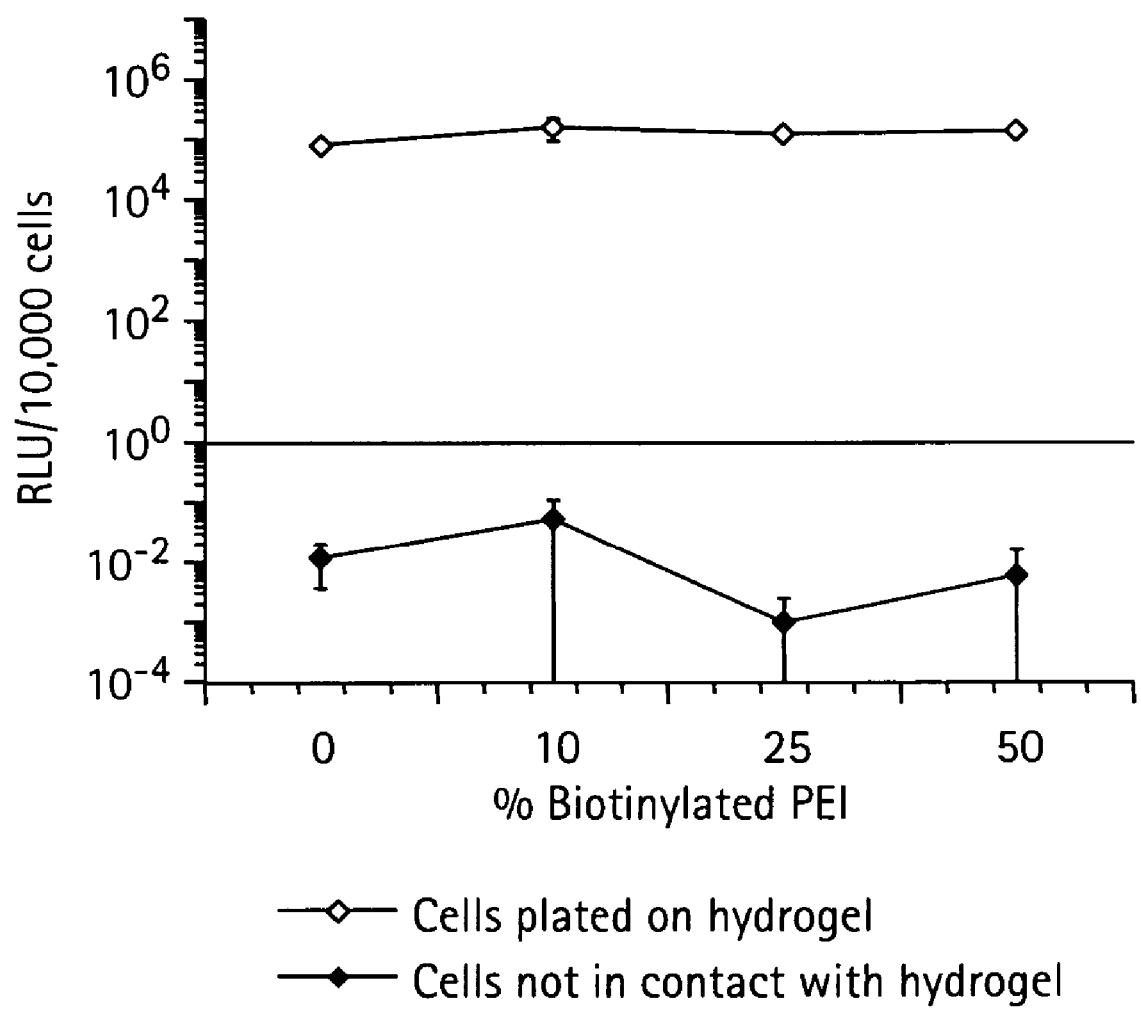

CONTROLLED SURFACE-ASSOCIATED DELIVERY OF GENES AND OLIGONUCLEOTIDES

CROSS-REFERENCE TO RELATED APPLICATIONS

The present application is a Continuation-in-Part of U.S. application Ser. No. 10/076,060, filed Feb. 14, 2002, now U.S. Pat. No. 6,890,556, which claims priority to provisional application Ser. No. 60/268,626, filed Feb. 14, 2001, the disclosures of which are hereby incorporated by reference in their entireties. Applicants claim the benefits of this application under 35 U.S.C. §119 (e) and §35 U.S.C. 120.

GOVERNMENT RIGHTS CLAUSE

The research leading to the present invention was supported by National Science Foundation Grant Number R01-GM066839-0141 and National Institutes of Health Grant Number BES-0092701. Accordingly, the Government has certain rights in the invention.

FIELD OF THE INVENTION

The present invention relates to methods for the controlled delivery of a nucleic acid into a cell. More specifically, the invention relates to methods of targeting and controlling the delivery of a nucleic acid to a cell or cell population with a system comprising DNA complexed to a polylinker which is attached to a support substrate.

BACKGROUND OF THE INVENTION

Developing systems capable of controlled and efficient gene transfer is a fundamental goal of biotechnology, with applications ranging from basic science to clinical medicine. Increasing or decreasing the expression level of a gene within a cell has the power to reveal or confirm the roles of specific components of signaling pathways and can lead to a mechanistic understanding of cell behavior, disease pathogenesis, and drug action. The successful application of gene transfer for basic science and clinical medicine requires the ability to manipulate the expression of target genes in the desired cell population. A variety of approaches are being taken to develop techniques to overcome barriers to gene transfer, which includes processes such as cellular internalization, endosomal escape, and nuclear trafficking.

Cationic polymers provide a versatile approach for gene transfer as the polymers can be designed or modified to overcome some of the current problems encountered with gene transfer. Complexation with cationic polymers functions to condense DNA, to produce a complex with a less-negative surface charge, to enhance cellular internalization of DNA, and to protect the DNA from degradation. Although many types of cationic polymers have been explored (see, for example, van de Wetering et al. (1999) Bioconjug. Chem. 10:589–597), polymers based on poly(L-lysine) (PLL)(see, for example, Choi et al. (1999) Bioconjug. Chem. 10:62–65), poly(ethylenimine) (PEI) (see, for example, Blessing et al. (2001) Bioconjug. Chem. 12:529–537), poly(amidoamine) (PAMAM) (see, for example, Qin et al. (1998) Hum. Gene Ther. 9:553–560), and poly(2-dimethylamino)ethylmethacrylate (p(DMAEMA)) (Arigita et al. (1999) Pharm. Res. 16:1534–1541) are among those utilized.

PEI covalently attached to a biodegradable polymer surface and to surface-immobilized collagen has been used as a gene delivery system. For example, Zheng et al. (2000) Biotechnol. Prog. 16:254–257, created a polymer surface with attached PLL and PEI, to which DNA was non-specifically adsorbed for delivery into a cell.

Recently, polymeric systems originally developed to deliver biologically active proteins have been adapted to deliver non-viral DNA. Polymeric scaffolds have been fabricated from a variety of materials, both natural (e.g., collagen) and synthetic (e.g., poly(lactide-co-glycolide)) which function as a support for cell adhesion and migration. These scaffolds act to increase the local concentration of DNA within the cellular microenvironment either by providing a sustained release of DNA (Shea et al. (1999) Nat. Biotechnol. 17:551–554) or by maintaining the DNA locally (Bonadio et al. (1999) Nat. Med. 5:753–759). Bielinska et al. (2000) Biomaterials 21:877–887 describe the use of a solid support membrane as a device for DNA delivery mediated by PAMAM dendrimers to skin cells. Synthetic systems have also been developed that increase cell-surface concentrations of DNA by adsorbing DNA complexes to the surface (Luo et al. (2000) Nat. Biotechnol. 18:893–895). U.S. Pat. No. 6,312,727 describes a nucleic acid delivery vehicle in which complexes formed from nucleic acids condensed with cationic polymer material are reacted with hydrophilic polymer material to form a hydrophilic coating or shield around the complex.

SUMMARY OF THE INVENTION

The present invention provides for novel systems for the controlled delivery of a nucleic acid to a target cell or cells that combines nucleic acid condensation with polymeric delivery by tethering or immobilizing nucleic acid complexes to a surface that supports cell adhesion. The gene delivery system of the invention allows both temporal and spatial control of gene delivery due to efficient internalization of the immobilized complex, elevated DNA concentrations in the microenvironment of cells adhered to the support substrate, and through alterations in the number of tether to the complexes and reversibility of complex immobilization.

The present invention also provides gene delivery by plasmids that are complexed with cationic polymers (polyplexes) or lipid (lipoplexes) and subsequently immobilized to cell culture or biomaterial substrates by adsorption. Polyplexes and lipoplexes were adsorbed to either unmodified (PS) or serum-adsorbed (FBS-PS) polystyrene. The quantity of DNA immobilized increases with time of exposure, and the deposition rate and final amount deposited depends upon the properties of the substrate and complex. For maximal transfection, this approach requires that the affinity of the DNA complex for the substrate must be sufficient to support immobilization, yet not excessive to limit cellular internalization.

The studies reported on herein have focused on manipulating the properties of the complex and substrate to modulate this binding affinity. Polyplexes and lipoplexes were examined based on their differences in chemical composition, size, and zeta potential, which may affect their interaction with the substrate. Additionally, serum adsorption was used as a simple approach to modulate the interaction of these complexes with the culture substrate. Substrate binding and cellular transfection (i.e., transfected cells, transgene expression) were measured for polyplexes and lipoplexes formed with varying amounts of cationic polymer or lipid, respectively. The mechanism of gene transfer was examined through the distribution and stability of complexes on the substrate. Furthermore, the invention demonstrates that substrate-mediated delivery can transfect primary human-derived cells, and that this approach can be extended to widely used biomaterials.

For polyplexes, serum modification maximally enhanced reporter gene expression 1500-fold relative to unmodified substrates, and yields equivalent or greater expression compared to bolus delivery. For lipoplexes, serum modification significantly increased the number of transfected cells relative to unmodified substrates, yet provided similar levels of expression. Immobilized complexes transfect primary cells with lower cytotoxicity relative to bolus delivery. This substrate-mediated delivery approach was successfully applied to a widely used biomaterial, poly(lactide-co-glycolide).

The invention also provides a substrate mediated strategy for delivering DNA complexes from hyaluronic acid (HA)-collagen hydrogels. Hydrogels were formed by crosslinking HA with poly(ethylene glycol) diglycidyl ether, and a topography was introduced using pattern transfer. DNA/PEI complexes of varied sizes were immobilized to the hydrogel substrate using biotin/neutravidin binding and non-specific adsorption.

Accordingly, in a first aspect, the invention features a controlled nucleic acid delivery system comprising nucleic acid-polylinker complexes tethered or immobilized to a support substrate, wherein the nucleic acid-polylinker complex is capable of being delivered or internalized by a cell adhering to the support substrate.

The nucleic acid-polylinker complexes are immobilized to the surface of a support substrate by a functional group attached to the polylinker. A polylinker modified by a functional group may attach to the support substrate directly or may attach through a modifying functional group present on the support substrate. The polylinker may be modified with a functional group before or after formation of the complex, but the complex must be formed prior to attachment to the solid support. The polylinker may be modified with a functional group before or after formation of the complex, but the complex must be formed prior to attachment to the solid support.

The complexes may be covalently or non-covalently immobilized. In one embodiment, the complexes are covalently attached to the support substrate. In this embodiment, the complexes may be formed by condensation of the nucleic acid with a non-modified polylinker. The complex is then reacted with a functional group on the support substrate to generate a covalent bond between the polylinker and the support substrate. In another embodiment of the covalent attachment of the complexes to the support substrate, the nucleic acid is condensed with a modified polylinker. The resulting complex is then reacted with a functional group on the solid support to generate a covalent bond between the polylinker and the support substrate. In another embodiment, the complexes are non-covalently immobilized to the support substrate. In this embodiment, the complexes may be formed by condensation of the nucleic acid with a non-modified polylinker. The complex is then modified with a functional group that will specifically interact with a functional group on the solid support to generate a non-covalent bond. In another embodiment of the non-covalent attachment of the complexes to the support substrate, the nucleic acid is condensed with a modified polylinker. The complex is then reacted with a functional group on the solid support to generate a non-covalent bond. In one embodiment, more than 0.2% of the immobilized complexes are bonded to the support substrate. In a specific embodiment, a covalent bond between a polylinker and the support substrate is broken after a cell is plated on the support surface.

In specific embodiments, the nucleic acid is DNA, RNA, or an oligonucleotide. In a more specific embodiment, the oligonucleotide is an antisense oligonucleotide or catalytic RNA capable of interfering with the expression of a gene. In another more specific embodiment, the DNA or RNA directs the intracellular expression of a gene.

In more specific embodiments, the polylinker is a cationic polymer, cationic lipid, cationic protein, or cationic peptide. In a specific embodiment, the polylinker is a cationic polymer or cationic peptide.

The support substrate of the invention is any substrate capable of supporting cell adhesion. In more specific embodiments, the support substrate is glass, collagen, peptide polymers, polysaccharide polymers, carbohydrate, polymers, polystyrene, lipid, metal, plastic, alumina gels, nitrocellulose, nylon membranes, cotton, or glass wool. In another embodiment, the support substrate is HA-collagen hydrogel. The support substrate either contains or can be chemically modified to contain a functional group that allows the support substrate to covalently bind to a bifunctional crosslinker or polylinker modified to have a functional group.

In the controlled nucleic acid delivery system of the invention, nucleic acid delivery is controlled through (i) complex density at the surface of the support substrate, (ii) complex location on the surface of the support substrate, and (iii) the number of bonds linking the polylinkers in the complex to the support substrate. In one embodiment, the bonds between the polylinkers and the support substrate are reversible. In a specific embodiment, complex density on the surface of the support substrate ranges from 0.01 to 10.0 µg DNA/cm$^2$; and in a more specific embodiment, from 0.05 to 5.0 µg DNA/cm$^2$.

The relative strength of the attachment between the immobilized complex and the support substrate, and the reversibility of complex immobilization at the surface of the support substrate are factors that determine the release rate of a complex from the support substrate, and the availability of the released complex for internalization, e.g., delivery, to a cell or cell population.

In a second aspect, the invention features a method of controlled nucleic acid delivery, comprising (a) contacting a nucleic acid with a polylinker, wherein the nucleic acid complexes with the polylinker to form a nucleic acid-polylinker complex, and (b) immobilizing the nucleic acid-polylinker complex of step (a) to a support substrate able to support cell adhesion, wherein the immobilization is through the polylinker, and wherein delivery of the nucleic acid to a cell is controlled by (i) density and location of the complex on the surface of the support substrate, and (ii) the number of bonds attaching the polylinkers in the complex to the support substrate.

In specific embodiments, the complexes may be covalently or non-covalently immobilized through the polylinker to the support substrate. In one embodiment, the complexes are covalently attached to the support substrate. In another embodiment, the complexes are non-covalently immobilized to the support substrate. In either embodiment, the complexes may be formed by condensation of the nucleic acid with a modified polylinker, by condensation of the nucleic acid with a non-modified polylinker, or by condensation of the nucleic acid with a mixture of modified polylinker and non-modified polylinker. The number of bonds linking the polylinker to the support substrate can be manipulated by i) varying the extent of modification of the polylinker, or ii) varying the ratio of modified to non-modified polylinker during complex formation.

In one embodiment, the support substrate is modified with a functional group capable of interacting with the non-modified polylinker in the complex. In another embodiment, the polylinkers are modified with a first functional group prior to step (a) and the support substrate is modified with a second functional group capable of interacting with the first functional group. In one embodiment, the nucleic acid is contacted with both modified and unmodified polylinkers, forming nucleic acid-polylinker complexes which bind to the support substrate with varying binding strengths, and thus are released over a period of time as a result of the different bond strengths. In another embodiment, the bond between the polylinker and the support substrate is reversible. In a further embodiment, the support substrate may be modified with a second functional group able to interact with the first functional group modifying a polylinker. In a specific embodiment, polylinker is poly-L-lysine (PLL), the first functional group is biotin, and the second functional group is avidin, strepavidin, or an avidin derivative.

In a third aspect, the invention features a method of making a controlled nucleic acid delivery system, comprising (a) contacting a nucleic acid with polylinkers; wherein the nucleic acid complexes with the polylinkers to form a condensed nucleic acid; and (b) immobilizing the polylinker present in the complex to a support substrate, wherein delivery of the nucleic acid to a cell is controlled by (i) density and location of the complex on the surface of the support substrate, and (ii) reversibility of the attachment of the polylinker to the support substrate the number of bonds linking the polylinker in the complex to the support substrate wherein a desired release rate is achieved. In one embodiment, the polylinkers are modified with a first functional group prior to step (a) and the support substrate is modified with a second functional group capable of interacting with the first functional group. In a further embodiment, the nucleic acid is contacted with both modified and unmodified polylinkers.

In a fourth aspect, the invention features a method of spatially controlling the delivery of a nucleic acid to a cell comprising: (a) modifying a polylinker with a first functional group; (b) contacting a nucleic acid with modified polylinker; wherein the nucleic acid complexes with the polylinker to form a condensed nucleic acid; and (c) immobilizing the nucleic acid-polylinker complex to a surface of a support substrate, wherein the surface of the support substrate is modified with a second functional group capable of interacting with the first functional group, and wherein complexes formed with modified polylinker are specifically bound to the support surface, and wherein the specific binding of the complexes to the surface of the support substrate is located at specific regions of the substrate in a defined pattern.

In one embodiment, the nucleic acid is contacted with both modified and unmodified polylinker in step (a) and the unmodified polylinker in the complex is not bound to the support surface in step (c). In a specific embodiment, the substrate is a microtiter plate comprising multiple wells.

In a fifth aspect, the invention features a method of temporally controlling the delivery of a nucleic acid to a cell population comprising: (a) modifying a polylinker with a first functional group; (b) contacting a nucleic acid with modified polylinker; wherein the nucleic acid complexes with the polylinker to form a condensed nucleic acid; and (c) immobilizing the nucleic acid-polylinker complex to a surface of a support substrate, wherein the surface of the support substrate is modified with a second functional group capable of interacting with the first functional group, and wherein the modified polylinker present in the complex is specifically bound to the support surface, and wherein the specifically bound complexes are released at desired times and internalized by a cell adhering to the surface of the support substrate.

In a sixth aspect, the invention features a method of temporally and spatially controlling the delivery of a nucleic acid to a cell population comprising: (a) modifying a polylinker with a first functional group; (b) contacting a nucleic acid with modified polylinker; wherein the nucleic acid complexes with the polylinker to form a condensed nucleic acid; and (c) immobilizing the nucleic acid-polylinker complex to a surface of a support substrate, wherein the surface of the support substrate is modified with a second functional group capable of interacting with the first functional group, and wherein complexes formed with modified polylinker are specifically bound to the support surface and located at specific regions of the substrate in a defined pattern, and wherein the specifically bound complexes are released at desired times and internalized by a cell adhering to the surface of the support substrate.

In a seventh aspect, the invention provides methods for increasing transgene expression. In one embodiment, the method comprises making a controlled nucleic acid delivery system, comprising forming nucleic acid polylinker complexes, wherein the complexes are covalently or non-covalently immobilized to the surface of a support substrate, and wherein the method comprises:

a) contacting a nucleic acid with a polylinker to form a nucleic acid-polylinker complex;

b) immobilizing the nucleic acid-polylinker complex to a support substrate; and wherein the cells are added to the support substrate after immobilization of the nucleic acid-polylinker complex to the support substrate.

In another embodiment, the method further comprises modification of the support substrate with serum prior to addition of the nucleic acid-polylinker complex, and wherein said modification allows for an increase in transgene expression.

In yet another embodiment, the extent of transgene expression is dependent upon substrate modification and complex formation. In a particular embodiment, the nucleic acid polylinker complexes are polyplexes or lipoplexes. In a particular embodiment, the increase in transgene expression occurs when the polyplexes are immobilized to the support substrate at low densities or low doses, such as, but not limited to the doses used herein. The optimal doses and densities of the polyplexes and/or lipoplexes may depend on the support substrate used, as well as the cell type for which gene delivery is desired. The methods for determining such would be known to one skilled in the art. In yet another particular embodiment, the increase in transgene expression is optimized at a particular N/P ratio, which also may be optimized depending on the substrate used and the cell type for which gene delivery is desired.

In yet another particular embodiment, the support substrate is biodegradable or non-biodegradable. In a more particular embodiment, the support substrate is polystyrene (PS), gold, or poly(lactide-co-glycolide) (PLG). In yet another particular embodiment, the support substrate is a hydrogel. In a more particular embodiment, the hydrogel is hyaluronic acid (HA)-collagen hydrogel.

In yet another embodiment, the support substrate may be treated with (modified) serum, such as but not limited to, fetal bovine serum. In a particular embodiment, the delivery of the nucleic acid-polylinker complexes to cells occurs from a polystyrene surface treated with serum, and such delivery results in a similar or a greater percentage of transfected cells relative to bolus delivery. In yet another particular embodiment, such delivery further comprises release of the nucleic acid from the nucleic acid-polylinker complexes, and the release is maximized when the support substrate is pretreated with serum. In yet another particular embodiment, the release of nucleic acid from the nucleic acid-polylinker complexes is further enhanced when the support substrate containing the complexes is incubated in conditioned medium. In yet another particular embodiment, the delivery of the nucleic acid-polylinker complexes to cells from a serum-modified support substrate results in higher cellular association of the nucleic acid-polylinker complexes with the support substrate.

In an eighth aspect, the invention provides a method for increasing transgene expression, comprising the steps of:
a) making a controlled nucleic acid delivery system by contacting a nucleic acid with a polylinker to form a nucleic acid-polylinker complex;
b) immobilizing the nucleic acid-polylinker complex to a support substrate; wherein said immobilizing is accomplished by covalent or non-covalent means, and
c) adding the cells into which transgene expression is desired to the support substrate after immobilization of the nucleic acid-polylinker complex to the support substrate.

In one particular embodiment, the support substrate comprises a biodegradable or non-biodegradable material. In a more particular embodiment, the biodegradable material is poly(lactide-co-glycolide) or a hydrogel and the non-biodegradable material is polystyrene. In a more particular embodiment, the hydrogel is hyaluronic acid (HA)-collagen hydrogel.

In yet another particular embodiment, the nucleic acid-polylinker complexes are formed prior to attachment to the solid support substrate.

In yet another particular embodiment, the method promotes transfection of primary cells. In a particular embodiment, the primary cells are fibroblast cells, although any primary cell or cell line for which gene delivery is desired may be envisioned by the present invention. These may include neuronal cells, skin cells, stem cells, tumor cells and the like.

In yet another particular embodiment, the nucleic acid polylinker complexes are immobilized to the support substrate using biotin and avidin or an avidin derivative, such as streptavidin or neutravidin. In yet another particular embodiment, the nucleic acid-polylinker complexes are immobilized to the support substrate by non-specific adsorption.

In yet another particular embodiment, the method further comprises controlling the size of the nucleic acid polylinker complex by regulating the salt content during complex formation. In a more particular embodiment, the forming of large diameter complexes in the presence of salt results in increased transgene expression, and the forming of small diameter complexes in the absence of salt results in a greater percentage of cells being transfected. In a more particular embodiment, the salt is sodium chloride.

In yet another particular embodiment, the method further comprises release of the nucleic acid from the substrate, wherein the release is optimized by using conditioned medium. In a more particular embodiment, the method further comprises biotinylation of the complex to enhance release of the complex from the substrate.

In another particular embodiment, the nucleic acid is DNA, RNA or an oligonucleotide. In a more particular embodiment, the oligonucleotide is an antisense oligonucleotide or a catalytic RNA capable of interfering with the expression of a gene.

In yet another particular embodiment, the polylinker is a cationic polymer, cationic lipid, cationic protein, or cationic peptide.

Other objects and advantages will become apparent from a review of the ensuing detailed description taken in conjunction with the following illustrative drawings.

BRIEF DESCRIPTION OF THE FIGURES

FIG. 15 shows the diameter and zeta-potential of DNA complexes. (A) z-average diameter and (B) zeta potential of PEI polyplexes with increasing polymer/DNA ratio (N/P). (C) z-average diameter and (D) zeta potential of Lipofectamine 2000 lipoplexes with increasing volumes of lipid used to complex 1 μg of DNA. Data is presented as average ± standard deviation of the mean. * indicates $p<0.05$ relative to remaining data (A).  indicates $p<0.05$ relative to N/P equal to 5 (B). * indicates $p<0.05$ relative to 0.5 μL of lipid. For this and all other figures, p values were obtained using the Student's t test with single comparisons.

FIG. 23 shows transfection of primary human dermal fibroblasts. (A) GFP expression from bolus delivery of 0.5 μg lipoplexes. (B) GFP expression from FBS-PS substrate-mediated delivery of 1 μg lipoplexes incubated on substrate. Luciferase activity from substrate and bolus delivery of (C) polyplexes and (D) lipoplexes. Data is presented as average ±standard deviation of the mean. * indicates $p<0.05$ relative to other delivery methods for that condition.

FIG. 27 shows surface densities of DNA/PEI complexes immobilized to HA collagen-NA hydrogels for complexes formed in 150 mm NaCl or water (A). Plotted data is an average of triplicate conditions. Fluorescence photomicrographs of immobilized biotinylated DNA/PEI complexes (N/P=5) to HA-collagen-NA hydrogels. Biotinylated complexes formed in water (B) or 150 mm NaCl (C) were incubated on the substrate for 120 min. Images were captured after washing the substrate with PBS buffer.

FIG. 32 shows luciferase transgene expression in NIH/3T3 cells mediated by immobilized complexes to HA-collagen-NA substrates for cells durectly attached to the hydrogel (open diamonds) or not in contact with the hydrogel (closed diamonds). % biotinylated PEI indicate the percent biotinylation of the complexes. All complexes were formed at an N/P ratio of 5. Plotted data are an average of triplicate conditions.

DETAILED DESCRIPTION OF THE INVENTION

Figure 1:
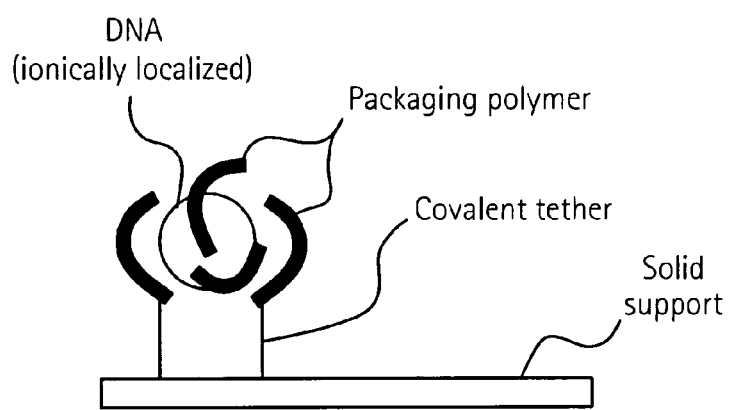
FIG. 1 is a schematic depiction of DNA condensation (ionically localized) with polymeric delivery to tether DNA complexes to the surface of a hydrogel.

Before the present methods and compositions are described, it is to be understood that this invention is not limited to particular methods, compositions, and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a polylinker" includes mixtures of such polylinkers, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Definitions

By the term "nucleic acid", "gene", or the like, is meant a polynucleotide such as a plasmid, DNA, or RNA capable of being internalized by a cell in the nucleic acid-polylinker complex of the invention. The internalized nucleic acid may encode a protein, a growth factor, a hormone, etc., or may be an antisense oligonucleotide which interferes with the expression of a gene. The instant invention provides a condensed nucleic acid in the form of a nucleic acid-polylinker complex immobilized on the surface of a support substrate; the complex is released from the surface of the support subtrate into the cell microenvironment, and is capable of being internalized by the cell. As shown in the experiments reported below, a cell taking up the released complex is transformed and able to express the transgene of the internalized complex.

The terms "support substrate", "solid substrate", "solid support", "support" and "supporting scaffold" are used interchangeably and represent a material that binds a polylinker which is complexed with a nucleic acid, which provides a surface for a cell to interact with the nucleic acid associated with the solid substrate, and which is biocompatible, e.g., non-toxic, to cells.

The solid substrate may contain, or can be chemically modified to contain a functional group that allows the solid substrate to covalently bind to a bifunctional polylinker. Examples of material that can be used as solid substrates include glass, peptide polymers (e.g., collagen), HA-collagen hydrogel, peptoid polymers, polysaccharides (including commercial beads, e.g., SEPHADEX and the like), carbohydrates, hydrophobic polymers, polymers, tissue culture polystyrene, planar lipid layers, planar lipid bilayers, metals, derivatized plastic films, glass beads, plastic beads, alumina gels, magnetic beads, nitrocellulose, cellulose, nylon membranes, cotton, and glass wool.

Figure 5:
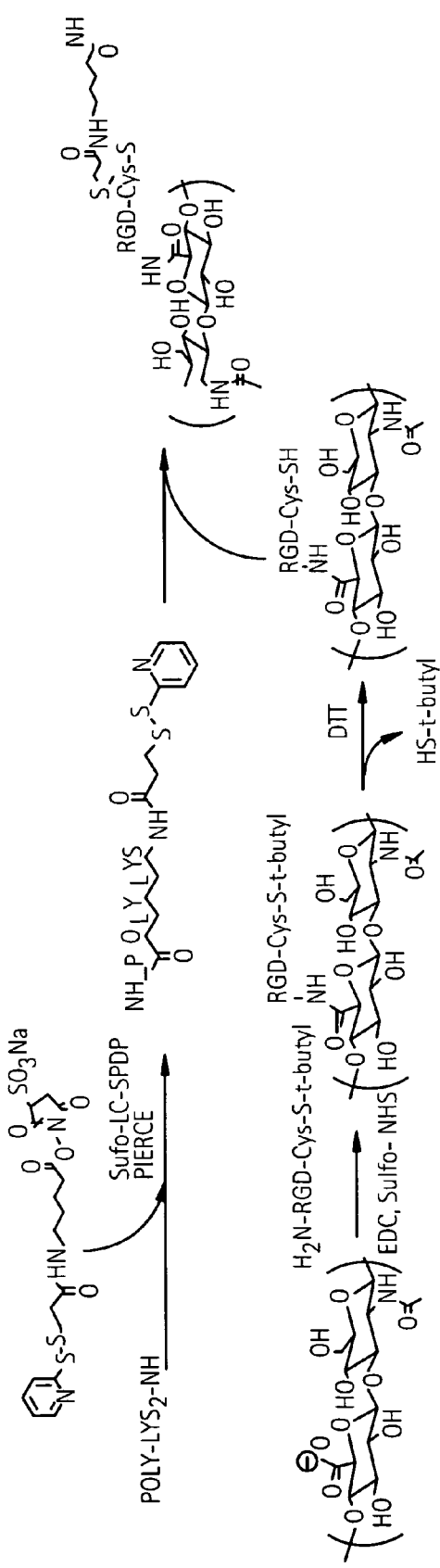
FIG. 5 depicts a method of surface modification and DNA tethering.
Figure 6:
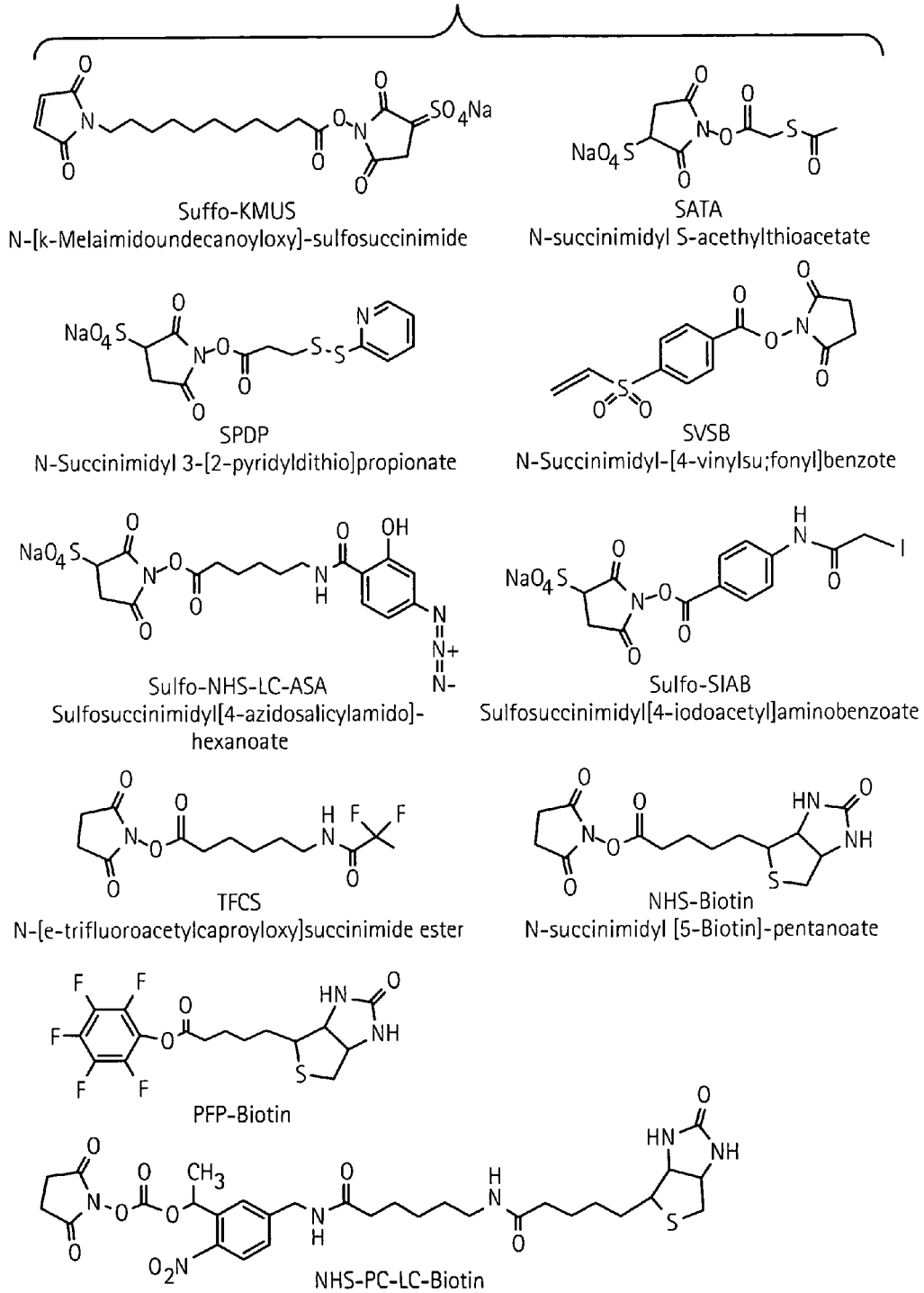
FIG. 6 shows the chemical structures of bifunctional cross-linkers exemplifying some of the types of compound that can be employed by the present invention. These cross-linkers are bifunctional, e.g., having two reactive centers. As shown, these molecules have their reactive centers at opposite ends and can be used to bind two molecules together.

The term "bifunctional agent" is used interchangeably with "bifunctional cross-linker" and is a compound that comprises two chemically reactive groups such as a thiol, an amine, a ketone, or an aldehyde, or a pair of binding partners such biotin-streptavidin, biotin-avidin, antibody-antigen, and receptor-ligand. Particular bifunctional cross-linkers are exemplified in FIG. 6. Bifunctional cross-linkers are used in the present invention in one embodiment to covalently bind a polylinker to a support substrate, in which one end of the bifunctional cross-linker is covalently attached to a reactive group on the substrate and the other end is covalently bound to the polylinker. See FIG. 5 as an example of modification of the surface support and DNA tethering or immobilization.

The terms "polylinker" or "accessory molecule", are used herein interchangeably to define a polymer or other cationic compound that can act to complex with and condense the molecule of interest, e.g., a nucleic acid, and immobilize it on or tether it to a solid substrate. Examples of polylinkers include cationic polymers, cationic peptides, cationic peptoids, or cationic compounds such as cationic lipids.

As used herein a "tether" is a bond that covalently or non-covalently attaches an accessory molecule to the solid substrate, either directly or through a bifunctional cross-linker. Preferably, this bond is reversible and/or can be broken enzymatically.

As used herein the term "condensed nucleic acid" is a nucleic acid (e.g., a DNA plasmid or an oligonucleotide) that is non-covalently associated with accessory molecules thereby forming a complex (see examples below). Examples of condensing agents include cationic polymers, cationic lipids and polycations.

As used herein the term a "molecule of interest" is a molecule that is tethered to a solid support for use in the methodology disclosed by the present invention. Such molecules of interest include nucleic acids such as a DNA (preferably a plasmid), an oligonucleotide, or a modified oligonucleotide (e.g., phosphorothioate).

As used herein the term "polyplex" refers to a nucleic acid that is complexed with cationic polymers, such as, but not limited to, polyethylenimine (PEI).

As used herein, the term "lipoplex" refers to a nucleic acid that is complexed with a lipid, such as, but not limited to, the cationic lipid Lipofectamine 2000.

As used herein, immobilizing a nucleic acid to the cell culture substrate prior to cell seeding has been termed "substrate-mediated delivery" or "solid phase delivery".

"N/P" refers to the ratio of nitrogen to phosphorous.

As used herein, the term "conditioned media" refers to growth media collected from cells having been in culture for at least 24 hours. The particular cells from which culture media was collected in the present studies were NIH/3T3 cells.

As used herein, "modification of the support substrate" may be defined as any alteration in the surface characteristics of the substrate which may affect binding of the complexes. Such modifications may be chemical modifications such as the covalent or non-covalent interactions described herein. Alternatively, the modifications may refer to non-chemical modifications that affect the binding of the complexes to the substrate. For example, the use of serum for modifications of the substrate may have a two-fold effect. In one case, the nitrogens from the proteins present in serum may alter the binding characteristics of the complex to the substrate. Alternatively, the serum may "modify" the surface of the substrate by altering the wettability, which in turn may affect the binding characteristics of the complexes to the substrate.

General Description

One aspect of the invention provides a nucleic acid-polylinker complex immobilized or tethered to a supporting substrate or scaffold, wherein a cell adhered onto the supporting substrate is capable of internalizing the nucleic acid complex and expressing the protein encoded by the nucleic acid.

The approach involves forming a non-covalent binding complex between the nucleic acid and the polylinker molecule. The polylinker molecules are bound to the solid substrate. The tethering of the complex serves to localize the nucleic acid to the surface, thus placing it directly into the cell microenvironment.

The invention also provides for characterization of gene transfer by DNA complexes adsorbed to tissue culture polystyrene and biomaterial substrates. Polyplexes and lipoplexes were adsorbed to either unmodified (PS) or serum-adsorbed (FBS-PS) polystyrene. Complex immobilization to the substrate increased with time of exposure, and the deposition rate and final amount deposited depended upon the properties of the substrate and complex.

Polyplexes immobilized to FBS-PS provide greater transfection than polyplexes immobilized to PS, and equivalent or greater transfection than "bolus" delivery of complexes, wherein the delivery of the nucleic acid complexes to cells is accomplished all at one time. Moreover, there is greater cytotoxicity associated with bolus delivery as compared to the substrate-mediated approach. Lipoplexes, however, provide similar levels of transgene expression on serum coated and uncoated surfaces. Interestingly, transfection on serum coated surfaces increases the number of transfected cells relative to uncoated surfaces. Immobilized complexes are able to transfect primary cells, and result in lower cytotoxicity relative to bolus delivery. Finally, this delivery mechanism can be adapted to biomaterial surfaces, such as PLG, which is commonly used for biomedical applications such as tissue engineering.

Reverse transfection and substrate-mediated delivery are based on the immobilization of DNA complexes to the culture substrate, which has been achieved by several methods. Ziauddin and Sabatini deposit naked DNA followed by addition of a cationic lipid. Plasmid DNA is suspended in gelatin and spotted onto a slide, which is followed by lipid addition to the culture media. Substantial transfection of HEK 293 cells was observed using this approach (Ziauddin and Sabatini 2001, Nature 411(6833): 107–10), and may require some modification to transfect other cell types (Bailey et al. 2002, Drug Discov Today 7(18 Suppl):S113–8; Wu et al. 2002, Trends Cell Biol 12(10):485–8).

An alternative to the DNA/gelatin immobilization procedure involves the complexation of plasmid with cationic lipids or polymers, which are then immobilized to the substrate. Biotin residues have been attached to cationic polymers, which are then mixed with plasmid to facilitate specific binding of DNA complexes to an avidin-modified substrate (Segura and Shea 2002, Bioconjug Chem 13(3): 621–9; Segura et al. 2003, J Control Release 93(1):69–84). Increasing the number of biotin residues enhanced substrate binding, whereas maximal transfection of HEK293 and NIH/3T3 cells was observed with few numbers of biotin residues. However, complexes can be non-specifically adsorbed to the substrate, likely through interactions between the cationic lipid or polymer and the substrate.

Complexes have been formed in the presence of extracellular matrix components and dried onto the substrate (Yoshikawa et al. 2004, J Control Release 96(2):227–32). This approach transfected a variety of cell types, including human mesenchymal stem cells.

The present invention provides for polyplex and lipoplex binding to the substrate from solution, and the ability to transfect cell lines and primary human-derived cells, all of these aspects having advantages over the existing methods. The studies presented herein have sought to characterize properties of the substrate and the complexes that mediate substrate immobilization and transgene expression.

Substrate immobilization of DNA complexes by adsorption results from non-covalent, nonspecific interactions between the substrate and complexes, and can depend upon the molecular composition of both vector and substrate. Non-specific adsorption of proteins to surfaces has been characterized by molecular interactions, which include hydrophobic, electrostatic, and van der Waals interactions (Norde and Lyklema 1991, J Biomater Sci Polym Ed 2(3): 183–202). DNA complex adsorption likely occurs through similar mechanisms. Both lipoplexes and polyplexes adsorb to the substrates, with at least 60% immobilized after 24 hour incubation. Substrate immobilization can prevent complex aggregation (Segura et al. 2003, J Control Release 93(1):69–84), maintain complexes at the surface during wash steps, and may enhance complex stability.

Figure 22A:
FIG. 22 shows distribution of cells and polyplexes on substrate following cell culture. Confocal microscopic images of polyplexes on (A) PS and (B) FBS-PS 20 hours after cell seeding. Polyplexes (2 μg, N/P=25) was incubated on substrates for 2 hours. Images captured 20 hours after cell seeding. Plasmid was labeled with tetramethyl-rhodamine and cells were stained with fluorescein diacetate.
Figure 22B:

Maximal transfection from the substrate is hypothesized to represent a balance between complex binding to the substrate and cellular internalization. As shown herein, transfection was observed with both polyplexes and lipoplexes adsorbed to serum modified and unmodified polystyrene, suggesting that substrate-mediated delivery is applicable to a variety of transfection reagents and substrates. However, this cellular transfection by the immobilized DNA complexes was not equivalent across substrates and transfection reagents. Serum coating of polystyrene could enhance transgene expression (polyplexes) or the percentage of transfected cells (lipoplexes). These differences in the transfection profile do not reflect substantial differences in the amount of DNA immobilized (FIG. 18), and may result from differences in cellular internalization from the substrate. Conditions with relatively low transfection had DNA bound to the substrate, whereas conditions with higher transfection showed less substrate-associated DNA and more cell-associated DNA (FIG. 22). Addition of conditioned media to the substrates significantly enhanced release of the complexes relative to incubation with PBS. A cellular product, such as proteases, may promote release of the complexes from the substrate. The mechanism of cellular internalization from the substrate, and DNA distribution among the cell populations are the focus of continuing studies.

Maximal transgene expression for polyplexes and lipoplexes by substrate-mediated delivery is similar, yet the transfection profile and dependence on the substrate properties reflect differences in composition and intrinsic transfection properties. Polyplexes and lipoplexes have substantially different z-average diameters, zeta-potential, and chemical composition. Increasing the N/P ratio for polyplexes increases their zeta potential and reduces their size (Boussif et al. 1995, Proc Natl Acad Sci USA 92(16): 7297–301; Choosakoonkriang et al. 2003, J Pharm Sci 92(8):1710–22; Ogris et al. 2001, AAPS PharmSci 3(3): E21). Conversely, altering the composition of lipoplexes has less marked effects on the complex diameter and zeta-potential (FIG. 15). An increasing N/P ratio decreases binding of polyplexes to PS and has no effect on FBS-coated PS. As shown herein, for a 2 hour deposition, polyplexes bind more effectively than lipoplexes, with a difference of approximately 16%. Polyplex delivery from serum-modified substrates could increase transgene expression relative to delivery from PS and to equivalent quantities delivered as a bolus. However, lipoplex delivery yields similar levels of expression across delivery methods. Interestingly, lipoplexes increase the number of transfected cells relative to polyplex delivery, and produce the greatest percentage of transfected cells by delivery from serum-coated substrates.

Immobilization of DNA complexes by adsorption can be extended to biomaterials for applications such as tissue engineering. Porous PLG or collagen scaffolds have been fabricated with encapsulated polyplexes or lipoplexes, which have achieved substantial transfection in vitro (Cohen-Sacks et al. 2004, J Control Release 95(2):309–20; Huang et al. 2003, J Biomed Mater Res 67A(4): 1384–92; Scherer et al. 2002, J Gene Med 4(6):634–43) and in vivo (Scherer et al. 2002, J Gene Med 4(6):634–43.). The presence of the cationic lipid or polymer can significantly alter the release profile compared to plasmid DNA. The biotin-avidin interaction has been used to bind both viral and non-viral vectors to a variety of materials (Levy et al. 2001, Gene Ther 8(9):659–67; Segura et al. In Press). Alternatively, complexes formed with polyamidoamine (PAMAM) dendrimers have been dried onto PLG and collagen membranes coated with phosphatidyl glycerol (1–5%) (Bielinska et al. 2000, Biomaterials 21(9):877–87). In vitro transfection was comparable to bolus controls, while in vivo delivery enhanced expression six to eight-fold relative to plasmid delivery. Alternatively, plasmid DNA has also been incorporated into inorganic calcium phosphate co-precipitates that are adsorbed onto PLGA matrices, which are mostly released by 48 hours (Kofron and Laurencin 2004, Biomaterials 25(13):2637–43). The present invention demonstrates the ability to adsorb complexes to PLG to obtain significant transfection on the substrate.

Hyaluronic Acid-Collagen Hydrogels for DNA Delivery via a Substrate Mediated Approach Another aspect of the invention provides a substrate mediated strategy for delivering DNA complexes from hyaluronic acid-collagen hydrogels. Hydrogels were formed by crosslinking HA with poly(ethylene glycol) diglycidyl ether, and a topography was introduced using pattern transfer. DNA/PEI complexes of varied sizes were immobilized to the hydrogel substrate using biotin/neutravidin binding and non-specific adsorption.

Manipulating complex properties for substrate mediated delivery can be employed to regulate the transfection profile (number of transfected cells, transgene expression). Complex size was modulated by forming complexes in the absence or presence of salt. Large complexes increased the extent of transgene expression relative to small complexes, whereas small complexes increased the number of transfected cells relative to large complexes. The aggregation of complexes in solution has limited the ability to correlate transfection to complex size at a specific N/P ratio (Hagstrom J E., Curr Opin Mol Ther 2000;2(2): 143–9; Ogris M, Steinlein P, Kursa M, Mechtler K, Kircheis R, Wagner E., Gene Ther 1998;5(10):1425–33; Ogris M, Steinlein P, Carotta S, Brunner S, Wagner E., AAPS PharmSci 2001;3 (3):E21). Cationic polymer/DNA (e.g., DNA/PEI) complexes aggregate in polyelectrolyte solutions (150 mm NaCl) (Goula D, Remy J S, Erbacher P, Wasowicz M, Levi G, Abdallah B, et al., Gene Ther 1998;5(5):712–7; Plank C, Tang M X, Wolfe A R, Szoka Jr F C., Hum Gene Ther 1999;10(2):319–32; Trubetskoy V S, Loomis A, Slattum P M, Hagstrom J E, Budker V G, Wolff J A., Bioconjug Chem 1999;10(4):624–8), and/or in solutions containing serum proteins such as albumin, fibronectin, and fibrinogen (Ogris M, Brunner S, Schuller S, Kircheis R, Wagner E., Gene Ther 1999;6(4):595–605; Lucas P, Milroy D A, Thomas B J, Moss S H, Pouton C W, J Drug Target 1999;7(2):143–56; Oupicky D, Howard K A, Konak C, Dash P R, ulbrich K, Seymour L W., Bioconjug Chem 2000;11(4):492–501; Xu B, Wiehle S, Roth J A, Cristiano R J., Gene Ther 1998;5(9):1235–43). Strategies to stabilize complex size in solution involve steric stabilization (Ogris M, Steinlein P, Carotta S, Brunner S, Wagner E., AAPS PharmSci 2001;3(3):E21; Goula D, Remy J S, Erbacher P, Wasowicz M, Levi G, Abdallah B, et al., Gene Ther 1998;5(5):712–7; Ogris M, Brunner S, Schuller S, Kircheis R, Wagner E., Gene Ther 1999;6(4):595–605; Xu B, Wiehle S, Roth J A, Cristiano R J., Gene Ther 1998;5(9):1235–43; Wolfert M A, Dash P R, Nazarova 0, Oupicky D, Seymour L W, Smart S, et al., Bioconjug Chem 1999;10(6):993–1004; Toncheva V, Wolfert M A, Dash P R, Oupicky D, Ulbrich K, Seymour L W, et al., Biochim Biophys Acta 1998;1380(3):354–68), caging (Trubetskoy V S, Loomis A, Slattum P M, Hagstrom J E, Budker V G, Wolff J A., Bioconjug Chem 1999;10(4):624–8; Adami R C, Rice K G., J Pharm Sci 1999;88(8):739–46), and anionic polymer/DNA particles (Trubetskoy V S, Budker V G, Hanson L J, Slattum P M, Wolff J A, Hagstrom J E., Nucleic Acids Res 1998;26(18):4178–85; Trubetskoy V S, Loomis A, Hagstrom J E, Budker V G, Wolff J A., Nucleic Acids Res 1999;27(15):3090–5). The increase in complex size with time in the presence of salts and/or serum proteins has been hypothesized to result from increased inter-complex interactions, which create bridges between complexes (Hagstrom J E., Curr Opin Mol Ther 2000;2(2): 143–9). Nevertheless, transfection results obtained here are consistent with a previous report showing large complexes (600 nm) achieved up to 500 fold greater luciferase expression than small complexes (60 nm); however, the percentage of transfected cells was less substantial between large complexes and small complexes (Ogris M, Steinlein P, Kursa M, Mechtler K, Kircheis R, Wagner E., Gene Ther 1998;5(10): 1425–33). The dependence of the transfection profile on complex size has been attributed to mass transport to the cell surface, and altered endosomal release (Ogris M, Steinlein P, Kursa M, Mechtler K, Kircheis R, Wagner E., Gene Ther 1998;5(10): 1425–33). For substrate-immobilization, mass transport limitations are likely insignificant and thus the transfection profile would be affected by endosomal release. Enhanced transgene expression for the large complexes may result from an increased content of DNA and PEI per complex, which can facilitate endosomal escape and increase the probability of DNA transport to the nucleus. Furthermore, these results suggest that small complexes are more effectively internalized resulting in larger numbers of transfected cells, but are not as effectively transported through the cell and thus lower transgene expression. In the present invention, immobilization of DNA complexes to the substrate occurred through non-specific adsorption and biotin-neutravidin (NA) binding. Non-specific adsorption of proteins to surfaces occurs through a variety of interactions, such as hydrophobic, electrostatic, and van der Waals (Norde W, Lyklema J., J Biomater Sci Polym Ed 1991;2(3):183–202). The adsorption of DNA complexes likely occurs through similar mechanisms, and is hypothesized to depend on the molecular composition of the vector (e.g., cationic polymer) and substrate. Cationic polymers such as polylysine and PEI have been used to coat tissue culture plastic for in vitro studies, and PEI/DNA complexes interact with serum proteins (Ogris M, Brunner S, Schuller S, Kircheis R, Wagner E., Gene Ther 1999;6(4):595–605; Lucas P, Milroy D A, Thomas B J, Moss S H, Pouton C W., J Drug Target 1999;7(2): 143–56; Oupicky D, Howard K A, Konak C, Dash P R, Ulbrich K, Seymour L W., Bioconjug Chem 2000;11(4):492–501; Xu B, Wiehle S, Roth J A, Cristiano R J. The contribution of poly L-lysine, epidermal growth factor and streptavidin to EGF/PLL/DNA polyplex formation. Gene Ther 1998;5(9): 1235–43). Previous reports demonstrated that the presence of biotin groups in the complex resulted in substantially increased binding to the NA-coated polystyrene substrate and transgene expression compared with nonbiotinylated complexes (Segura T, Shea L D., Bioconjug Chem 2002;13(3):621–9; Segura T, Volk M J, Shea L D, J Control Release 2003;93(1):69–84). AS shown herein, biotin residues have no significant effect on binding to the substrate, while DNA release and transgene expression are only moderately enhanced. For release in conditioned media and hyaluronidase, biotinylated complexes had an increased release (E15%) after 8 days with no significant effect at earlier times. Transgene expression, which is analyzed at two days, is enhanced by a factor of 2 or less with biotinylated complexes. These observations regarding in vitro binding, release, and transfection suggests that immobilization primarily occurs by non-specific interactions between the DNA/PEI complexes and the substrate. Release studies of the immobilized complexes in different release mediums indicate that complexes are released during incubation, and that released complexes transfect only cells that are adhered to the substrate. Immobilization of DNA complexes occurred through complexes interacting with the substrate, which contained NA (biotinylated complexes only), HA, and collagen. Hyaluronidase treatment would release DNA by degrading the HA backbone, the primary component of the substrate. Alternatively, conditioned media contains serum proteins and other cellular products that could induce release enzymatically or through competitive protein adsorption. Although approximately 50% of DNA/PEI complexes are released in conditioned media after 48 h, gene transfer at 48 h was only observed in cells that were directly attached to the hydrogel substrate (FIG. 32). The transfection of cells cultured on the hydrogel, but not incubated with the hydrogel, likely results from an elevated concentration in the cellular microenvironment. For cells cultured with the hydrogel, released complexes may be deactivated (e.g., aggregation) prior to cellular internalization, or mass transport limitations may minimize cellular uptake (Luo D, Saltzman W M., Nat Biotechnol 2000;18 (8):893–5).

The presence of RGD peptides in the DNA complex, which was hypothesized to increase cellular binding to the complexes through integrin receptors, resulted in lower transgene expression than unmodified complexes. The modification of cationic polymers with receptor ligands such as transferrin (Kircheis R, Kichler A, Wallner G, Kursa M, Ogris M, Felzmann T, et al., Gene Ther 1997;4(5):409–18), RGD (Kunath K, Merdan T, Hegener 0, Haberlein H, Kissel T.; J Gene Med 2003;5(7):588–99; Harbottle R P, Cooper R G, Hart S L, Ladhoff A, McKay T, Knight A M, et al., Hum Gene Ther 1998;9(7): 103747), and galactose (Plank C, Zatloukal K, Cotten M, Mechtler K, Wagner E., Bioconjug Chem 1992;3(6):533–9; Kunath K, von Harpe A, Fischer D, Kissel T., J Control Release 2003;88(1):159–72), enhance binding and internalization for complexes delivered as a bolus. Reduced transgene expression with ligand-modified complexes has been seen previously for complexes with a net positive charge (Kunath K, Merdan T, Hegener 0, Haberlein H, Kissel T., J Gene Med 2003;5(7):588–99; Kircheis R, Kichler A, Wallner G, Kursa M, Ogris M, Felzmann T, et al., Gene Ther 1997;4(5):409–18; Harbottle R P, Cooper R G, Hart S L, Ladhoff A, McKay T, Knight A M, et al., Hum Gene Ther 1998;9(7):1037–47; Plank C, Zatloukal K, Cotten M, Mechtler K, Wagner E., Bioconjug Chem 1992;3(6):533–9; Kunath K, von Harpe A, Fischer D, Kissel T., J Control Release 2003;88(1): 159–72). For substrate-mediated delivery, transgene expression decreased by an order of magnitude for complexes formed with 0% and 75% RGD-PEI, respectively. To our knowledge, this reduction in transgene expression as RGD content is increased at a fixed N/P has not been previously reported. A reduction in transgene expression with the presence of RGD peptides suggests that cellular interactions with the complex are not a factor limiting transgene expression.

Reduction in transgene expression with increased RGD content may result from the RGD peptide affecting intracellular transport or reduced complex internalization as a result of multiple cellular interactions occurring per complex, which could limit internalization. Biomaterial scaffolds that support cell adhesion and are capable of efficient gene delivery can provide a fundamental tool for localized transgene expression, which can stimulate and direct cellular processes that lead to tissue formation. The scaffold is typically biodegradable, functions to create and maintain a space for tissue formation, provides a support for cell adhesion and migration, and allows integration of the regenerating tissue with the host (Murphy W L, Mooney D J., J Periodontal Res 1999;34(7):413–9). DNA delivery from the scaffold frequently targets infiltrating fibroblasts, which can serve as bioreactors for the localized production of tissue inductive factors (Bonadio J, Smiley E, Patil P, Goldstein S., Nat Med 1999;5(7):753–9). Several strategies employ biomaterials to provide a sustained release of DNA or DNA complexes (Pannier A K, Shea L D. Mol Ther, in press.); however, DNA complexes can also be immobilized to concentrate the DNA at the biomaterial surface and prevent distribution to non-target tissues. The present invention demonstrates a strategy to immobilize DNA to hydrogels for delivery to adherent cells, with the properties of the immobilized complexes regulating the transfection profile (transgene expression, number of transfected cells). The appropriate expression profile will likely depend upon the physiological system and gene of interest. For example, transplanting engineered cells that secrete low levels of vascular endothelial growth factor (VEGF) produced a mature vascular network, which was not observed by transplantation of cells secreting high levels of VEGF (Ozawa C R, Ban. A, Glazer N L, Thurston G, Springer M L, Kraft P E, et al., J Clin Invest 2004;113(4):516–27). For genes that act intracellularly, such as tumor suppressor genes or transcription factors, the delivery system must transfect large numbers of cells (Braddock M., Ann Med 2001;33(5): 313–8; Scholl S M, Michaelis S, McDermott R., J Biomed Biotechnol 2003;2003(1):35–47). The present invention also demonstrates that immobilization enables spatial patterning of gene transfer by transfecting cells that attach and orient along a topographical pattern. The engineering of tissue structures, such as the intricate networks of the vascular and nervous systems, will require methods for controlling the physical placement of molecular signals (Saltzman W M, Olbricht W L., Nat Rev Drug Discov 2002;1(3):177–86). The ability to spatially regulate gene delivery on the scaffold can be employed to create spatial gradients in the expression of various tissue inductive factors (e.g., growth factors, matrix molecules), which are characteristic of many developing tissues. Opportunities for spatially controlled gene delivery include directing neurite outgrowth, or orienting cell growth for tissues such as muscle. This spatial control of cell attachment and transfection can be a powerful tool with broad applicability to tissue engineering.

Nucleic Acids

The present invention therefore utilizes condensed nucleic acids in a complex with polylinkers, wherein the polylinkers or a percentage thereof, are covalently and/or non-covalently bound to the surface of the support substrate. In one such embodiment the nucleic acid is a DNA molecule. In a more specific embodiment, the DNA molecule is a plasmid. In a related embodiment the DNA molecule encodes a protein. In another embodiment the nucleic acid is an oligonucleotide, and in specific embodiments, the oligonucleotide is an antisense molecule, a ribozyme, or a triple helix molecule.

Antisense, Ribozymes, and Triple Helix Molecules

The antisense nucleic acids of the invention comprise a sequence complementary to at least a portion of an RNA transcript of a gene, however, absolute complementarity, although preferred, is not required. A sequence "complementary to at least a portion of an RNA," as referred to herein, means a sequence having sufficient complementarity to be able to hybridize under stringent conditions (e.g., highly stringent conditions comprising hybridization in 7% sodium dodecyl sulfate (SDS), 1 mM EDTA at 65° C. and washing in 0.1×SSC/0.1% SDS at 68° C., or moderately stringent conditions comprising washing in 0.2×SSC/0.1% SDS at 42° C. with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In another embodiment, the nucleic acid of interest is a ribozyme or triple helix molecule used to modulate the activity, expression or synthesis of the gene present in the cell. Techniques for the production and use of such molecules are well known to those of skill in the art.

Ribozyme molecules designed to catalytically cleave gene mRNA transcripts can be used to prevent translation of target gene mRNA and, therefore, expression of the gene product. (See, e.g., PCT International Publication WO90/11364, published Oct. 4, 1990; Sarver et al. (1990) Science 247:1222–1225).

Ribozymes are enzymatic RNA molecules capable of catalyzing the specific cleavage of RNA. (For a review, see Rossi (1994) Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers (1995) Molecular Biology and Biotechnology: A Comprehensive Desk Reference, VCH Publishers, New York, (see especially FIG. 4, page 833) and in Haseloff and Gerlach (1988) Nature, 334, 585–591, each of which is incorporated herein by reference in its entirety.

Preferably the ribozyme is engineered so that the cleavage recognition site is located near the 5' end of the mRNA to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al. (1984) Science, 224, 574–578; Zaug and Cech (1986) Science, 231, 470–475; Zaug, et al. (1986) Nature, 324, 429–433; published International patent application No. WO 88/04300 by University Patents Inc.; Been and Cech (1986) Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the gene of interest.

As in the antisense approach, the ribozymes can be composed of modified oligonucleotides (e.g., for improved stability, targeting, etc.) and should be delivered to cells that express the gene of interest in vivo. A preferred nucleic acid for delivery involves using a DNA construct "encoding" the ribozyme under the control of a strong constitutive pol III or pol II promoter, so that transfected cells will produce sufficient quantities of the ribozyme to destroy endogenous mRNA encoding the protein of interest and inhibit translation. Because ribozymes, unlike antisense molecules, are catalytic, a lower intracellular concentration is required for efficacy.

Alternatively, the endogenous expression of an encoding gene of interest can be reduced by targeting deoxyribonucleotide sequences complementary to the regulatory region of the gene (i.e., the gene promoter and/or enhancers) to form triple helical structures that prevent transcription of the encoding gene of interest (See generally, Helene (1991) Anticancer Drug Des. 6(6), 569–584; Helene et al. (1992) Ann. N.Y. Acad. Sci., 660, 27–36; and Maher (1992) Bioassays 14(12), 807–815).

Nucleic acid molecules to be used in triplex helix formation for the inhibition of transcription in the present invention should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Antisense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Bifunctional Cross-Linkers

In one method of the invention, bifunctional cross-linkers are used as first and second functional groups to immobilize the nucleic acid-polylinker complex to the surface of the support substrate. Bifunctional cross-linkers have two reactive centers, which are generally at opposite ends of the cross-linker, e.g., a first and a second functional group, and are used to bind two molecules together (see, for example, FIG. 2). Sulfo-KMUS, SPDP, SATA, SVSB, and Sulfo-SIAB react with primary amines at one reactive center and sulfhydryl groups at the other reactive center. Sulfo-NHS-LC-ASA contains two reactive centers that react with primary amines. The reactions at either end of this cross-linker are independent since the reaction involving the azidosalicylamido group is activated by ultraviolet light. TFC reacts with primary amino groups at one of its reactive centers and activated carboxylic acids at its other reactive center. NHS-biotin, PFP-Biotin, and NHS-PC-LC-Biotin only have one reactive center that reacts with amino groups, whereas, the natural binding of biotin to streptavidin is employed as the second reactive center. NHS-PC-LC-Biotin is unique because when it is exposed to ultraviolet light it releases the original primary amine containing the molecule.

Polylinkers

A polylinker is selected for condensing with the molecule of interest, e.g., a nucleic acid. In different embodiments, the polylinker is a cationic polymer, a cationic protein or peptide, or a cationic lipid. The polylinkers of the present invention function to form a complex with the molecule of interest, and to immobilize the complex to the surface of the support substate. The polylinker may be covalently bound to the solid substrate. In a particular embodiment, the percentage of polylinkers covalently bound to the surface of the solid substrate is greater than 0.2%. In another embodiment, between 0.5–50% of the polylinkers are covalently bound to the surface of the solid substrate. In a more specific embodiment, between 1.0–25% of the polylinkers are covalently bound to the surface of the solid substrate. In a particular embodiment, the covalent bond between the polylinker and the solid substrate is broken after a cell is plated on the solid substrate.

Cationic lipids: The main components of a cationic lipid are a hydrophilic lipid anchor, a linker group, and a positively charged headgroup. The lipid anchor is typically either a fatty chain (e.g., derived from oleic or myristic acid) or a cholesterol group, which determines the physical properties of the lipid bilayer, such as flexibility and the rate of lipid exchange. The linker group is an important determinant of the chemical stability, biodegradability, and transfection efficiency of the cationic lipid. Biodegradable lipids can be metabolized by various enzymes (e.g., esterases, peptidases) to minimize any toxicity. The linker can also provide sites for the introduction of novel side chains to enhance targeting, uptake, and trafficking. The positively charged head group on the cationic lipid is responsible for interacting with the negatively charged DNA and is a critical determinant of the transfection and cytotoxicity of liposome formulations. The headgroups differ markedly in structure and may be single- or multiple-charged as primary, secondary, tertiary, and/or quaternary amines. The hydrophobicity of the lipid moiety has a crucial effect on in vitro gene transfer. Multivalent headgroups, such as spermine, in a "T-shape" configuration tend to be more effective than their monovalent counterparts at facilitating gene transfer. Generally, increases in the linker length correspond to increases in the gene delivery activity. Mixing of DNA and cationic lipid results in the collapse of DNA to form a condensed structure—termed lipoplex—in which nucleic acids are buried within the lipid. The thermodynamic driving force for association of the DNA and lipid is the entropy increase from the release of counter ions and bound water associated with DNA and the lipid surface.

The colloidal properties (e.g., size, stability) of the lipoplexes are principally determined by the cationic lipid/

DNA charge ratio and not the composition of the lipid or the helper lipid. The charge ratio (+/−) is typically defined as the number of amines on the cationic lipid relative to the number of phosphate groups on the DNA. A neutral charge ratio (1:1 charge ratio for lipid:DNA) should generally be avoided because it results in the formation of large aggregates (>1 μM). Lipoplexes prepared at a positive charge ratio and a negative charge ratio likely represent structures with different lipid and DNA packaging (Xu et al. (1999) Biophys. J. 77:341–353). At a positive charge ratio, large multilamellar vesicles (LMV, diameter 300–700 nm) transfect cells more efficiently than the small unilamellar vesicles (SUV, diameter 50–200 nm) (Felgner et al. (1994) J. Biol. Chem. 269:2550–2561; Turek et al. (2000) J. Gene Med. 2:32–40; Ross and Hui (1999) Gene Ther. 6:651–659). The order in which DNA and lipid are mixed is critical and significantly affects the lipid and DNA packing (Xu et al. (1999) supra). For the addition of DNA to lipid, a gradual increase in size is observed. When adding lipid to DNA, the particle size remains roughly constant until the amount of lipid positive charge exceeds the nucleic acid negative charge, whereupon the particles grow rapidly in size (Kennedy et al. (2000) Biophys. J. 78:1620–1633).

The net charge on the lipoplex affects its interactions with other components present in vivo and in vitro (e.g., media, serum, extracellular matrix glycoproteins, mucosal secretions), which can limit the transfection efficiency. A positive charge ratio, which facilitates interactions with the cell membrane, is generally prefered for in vitro studies (3:1), whereas in vivo use may require the charge ratio to be altered because of interactions with components of the physiological environment. The charge ratio of the complex determines the zeta potential, which ranges from −55 mV to +55 mV as the charge ratio is increased. Multivalent anions present in the serum or media can facilitate fusion of the lipids causing an increase in the size of the particle. Polyanions with adequate anionic charge density (e.g. heparin) released DNA from the complex by binding the cationic lipid. Serum can be a complicating factor for positively charged complexes, possibly causing premature release of the DNA from the complex and enhancing degradation by nucleases. For ON:lipid complexes, the various components of serum (e.g., BSA, lipoproteins, and macroglobulin) interact with the complexes and alter the complex diameter, zeta potential, and interfere with cellular uptake and nuclear trafficking.

To improve lipoplex stability, PEG-PE can be incorporated into the cationic liposome. Such liposomes are prevented from aggregating and interacting with serum components, which increases their stability (Hong et al. (1997) FEBS Lett. 400:233–237; Meyer et al. (1998) J. Biol. Chem. 273:15621–15627). Alternatively, a detergent can be placed in solution with the cationic lipid and DNA (Hofland et al. (1996) Proc. Natl. Acad. Sci. USA 93:7305–7309). Removal of the detergent by dialysis allows the formation of uniform complexes. Lyophilization can also increase their shelf life. Cryoprotectants (e.g., sucrose, trehalose) also can be added to prevent aggregation and fusion of plasmid/lipid complexes during lyophilization.

Formulations of cationic lipids have been widely applied for in vitro nucleic acid transfection (see, for example, Felgner et al. (1987) Proc. Natl. Acad. Sci. USA 84:7413–7417) and more than 30 products are commercially available for this purpose, including Lipofectin (a 1:1 mixture of DOTMA and DOPE), Transfectam, Lipofectase, Lipofect-AMINE, and LipoTaxi. Formulations of cationic lipids can further contain a zwitterionic or neutral colipid, such as DOPE or cholesterol, to enhance transfection.

Cationic Polymers: All cationic polymers contain high densities of primary amines, which are protonatable at neutral pH. This high density of positive charges allows the cationic polymers to form stable complexes with non-viral DNA. The cationic polymers self-assemble with DNA to generate condensed structures (40–100 nm in diameter) capable of entering the cell. Cationic polymers include polyallylamine, peptoids, methacrylamide, and cyclodextrin containing polymers. Such polymers vary widely in their structure, which ranges from linear to highly branched molecules and influences their complexation with nucleic acids and their transfection efficiency. In addition to providing positive charges for DNA complexation, the primary amines also serve as functional groups with which to chemically modify the polymers with ligands and peptides that can enhance one or more of the steps in the transfection process.

Poly-L-lysine (PLL) and poly-L-ornithine are the most commonly used cationic polymers for gene delivery. Differing in chemical structure only by the length of their side chain (4 versus 3 carbons), they are capable of mediating gene delivery both in vitro and in vivo (Duguid et al. (1998) Biophys. J. 74:2802–2814). In order to form uniform complexes, these polymers are generally synthesized on a solid support using a series of protecting/de-protecting synthetic steps (e.g. Fmoc chemistry) to obtain mono-disperse peptides. PLL is typically used at charge ratios (+/−) ranging from 3:1 to 6:1. The ideal length of the PLL represents a balance between two competing effects: effective condensation and cytotoxicity. Relative to low molecular weight, the high molecular weight PLL forms tighter, smaller condensates that are more resistant to the effects of salt concentration and sonication [Adami et al. (1998) J. Pharm. Sci. 87: 678–683). However, cytotoxicity has been found to be inversely related to particle size (Duguid et al. (1998) supra), likely due to the high molecular weight PLL.

Poly(ethylenimine) (PEI) has been widely used to mediate gene delivery due to its high cationic charge density resulting from the protonatable amine on every third carbon. PEI can be synthesized by the acid catalyzed ring opening polymerization of aziridine as either a linear or a branched structure. Similar to the PLL complexes, low molecular weight PEI is less cytotoxic than high molecular weight PEI. Furthermore, PEI/DNA complexes must also bear a net positive charge (6–13:1+/−ratio) in order to efficiently transfect cells (Boussif et al. (1995) Proc. Natl. Acad. Sci. USA 92:7297–7301; Fischer et al. (1999) Pharm. Res. 16:1273–1279, Goula et al. (1998) Gene Ther. 5:712–717). The presence of sodium chloride during complexation can result in particles with amorphous shapes and diameters greater than 1 μm.

Dendrimers are an attractive architecture for gene transfer because their well-defined structure and robust chemistry enables the synthesis of many generations of protonatable amines. Starbust dendrimers such as polyamidoamine dendrimers (PAMAM) are capable of mediating gene delivery (Fischer et al. (1999) supra; Bielinska et al. (1997) Biochim. Biophys. Acta 1353:180–190; Qin et al. (1998) supra). PAMAM can be synthesized from either an ammonia or ethylenediamine core by successive addition of methyl acrylate and ethylenediamine (Tomalia et al. (1990) Angew Chem. Int. Ed. Engl. 29:138–175). The surface charge and diameter of the dendrimer is determined by the number of synthetic steps (i.e. number of generations). The generation of PAMAM used to complex DNA determines particle size and transfection efficiency. At charge ratios (+/−) above or equal to one, no free DNA is observed. Higher levels of transfection are observed for PAMAM/DNA complexes formed from generation 5 and 6 dendrimers than with lower PAMAM generations [Fischer et al. (1999) supra].

Cationic polymers can also be used in combination with liposomes. DNA is initially complexed with PLL at low charge ratios and cationic lipids are subsequently added to completely condense the DNA. Alternatively, the PLL condensed DNA containing a net positive charge can subsequently be complexed with an anionic lipid. Precondensation with polylysine has been shown to reduce serum inhibition and also enhanced the transfection efficiency (Vitiello et al. (1996), Gene Ther. 3:396–404; Gao and Huang (1996) Biochemistry 35:1027–1036).

Control of DNA Delivery to Cell

The nucleic acid may be internalized directly from the surface since each nucleic acid molecule is complexed with many acessory molecules and only a fraction of them are tethered. Alternatively, the tethers linking the complex to the surface may be broken, thus releasing the entire complex as a soluble factor into the immediate cellular microenvironment for internalization. This system also provides the potential to spatially and temporally control gene delivery to cells on the scaffold. Spatial control is obtained through regulating the location where the DNA is tethered to the surface. Temporal control is obtained through the number of tethers used in localizing the DNA complex to the surface. Release of the complex into solution or uptake by cells may not occur if few tethers remain; thus, the timing of release or uptake can be regulated through the number of tethers that must be broken. The surface density of DNA, the number and type of tethers, the properties of the scaffold, and the design of the polylinker are major design criteria that affect release and uptake.

The number of tethers can be used to regulate how tightly a molecule of interest is associated with the solid support. Fewer tethers can allow for a quicker release or uptake of the molecule of interest, whereas more tethers can delay the release or increase uptake time.

The tethers or the bifunctional cross-linkers of the present invention can either be transient, that is a tether that they can be designed to break or be broken after a certain desired time frame, or they can be designed to be relatively stable. such as a protein which is susceptible to proteolytic enzymes, or alternatively, the tether can be relatively stable such a plastic or nylon.

In the case of a transient tether, the freeing of the molecule of interest can be effected by hydrolysis, in which the tether degrades slowly with time in the presence of water. In another embodiment, the tether is sensitive to an outside stimulus such as light, free radicals, radiation, etc., thereby being degraded by the stimulus and releasing the molecule of interest. One example of a transient cross-linker, is a protein that can be enzymatically cleaved causing the molecule of interest to be released. The enzymes catalyzing the bond-breaking reaction may be secreted by the cells or alternatively may be present in the extracellular space.

The case of a permanent tether or cross-linker, the molecule of interest would not be released as a soluble factor into the media, but would have to interact with the cell directly from the substrate surface. If the molecule of interest needs to be internalized, the cell would have to pull the molecule away from the components that link it to the surface; thus, the strength of interaction of the molecule with the cell would need to be greater than the interaction of the molecule with the substrate. Alternatively, the solid substrate itself may degrade to release the molecule of interest.

In one particular aspect, the method of the present invention spatially controls gene delivery to cells within predefined domains on a support substrate. A DNA sequence encoding for a specific gene, for example, is localized to a distinct domain on a support (e.g., a glass slide) for delivery to cells cultured within that domain. Internalization of the DNA complex modulates the expression of a specific gene within each domain. Thus, an array of cells is created in which gene expression varies between domains.

Reporter genes can be used to quantify the effectiveness of gene delivery. Reporter genes enable the quantification of the spatial location of protein production and the quantity of protein produced. A plasmid encoding for green fluorescent protein (GFP) for example, may be used to follow expression in the cell population cultured on the surface over time using a fluorescence microscope (see the examples below). The quantity of protein production also can be quantified using the reporter gene luciferase, which is assayed with a luminometer.

Uptake of the complex can be tracked by attaching a label (e.g., a fluorescent tag) to the molecule of interest or to the tether polylinker. The labeled molecule could be followed by fluorescence microscopy to determine if it has been internalized or acted upon by the cell. Labeling the tether polylinker with one fluorescent tag and the molecule of interest with a different tag may be used to follow the position and timing of each component separately.

The technique of tethering DNA to adhesive surfaces for enhanced gene transfer has additional applications for in vivo gene delivery and tissue engineering. Tethering of DNA to the surface of a solid support (e.g., polymer, glass) increases cellular uptake by placing the DNA directly at the cell surface, thus overcoming many mass transfer limitations associated with gene transfer. Cells will adhere to the material surface to which the DNA is tethered. Additionally, the tethering provides for a technique to control which cells have access to the DNA and allows for spatially regulated gene delivery.

In the present invention, controlled gene delivery and expression is achieved by sequestering DNA to specific locations, using techniques that still allow for internalization and expression. The strategy, shown in FIG. 1, combines the techniques of protein patterning, DNA packaging, and sustained release. In one example of the method of the invention, plasmid DNA is initially complexed with multiple types of cationic peptides in a process known as DNA condensation—a process designed to enhance cellular uptake and nuclear trafficking. Hundreds of cationic peptides bind to each plasmid. A fraction of these peptides are subsequently tethered to a support substrate using techniques established for controlled protein delivery. A support substrate can be glass or plastic, but for in vivo gene delivery and tissue engineering is more preferably a biocompatible solid substrate such as collagen or alginate, or a polyethylene glycol (PEG) based hydrogel. The tethering results in DNA being localized ionically at the surface of the support substrate by the covalently bound peptides. The peptides function to package the DNA for efficient transfection while the substrate surface localization maintains the DNA in the cell microenvironment for extended times, thus providing prolonged opportunities for internalization. The optimal number of tethers represents a balance between competing effects. If no tethers are present, the DNA is free in solution to be internalized, but spatial control cannot be achieved. If every peptide is a tether, internalization may not be possible because of the strong ionic interaction between the DNA and the peptide. Therefore, the amount of tethering of the DNA to the support substrate will vary with application. This can be achieved by forming DNA complexes that are tethered to the solid support with varying number of tethers. For example, cells can be seeded onto the solid support and examined for their ability to internalize and express a given gene. The optimal number of tethers to employ is therefore, readily determined by testing this parameter for any given desired application.

Another consideration is that the number of tethers can be designed to decrease with time, either through the action of proteases or through a degradable linker. The appropriate tethering serves to maintain the DNA at the surface for internalization either by receptor-mediated endocytosis which pulls the DNA from its ionic interaction with the tether or by degradation of the tethers which releases the DNA complex into solution in the cell microenvironment.

Cell Culture

Cells seeded onto the solid substrate can be cultured in vitro to ultimately produce tissues or portions of tissues for tissue transplantation. The culturing of cells on the solid substrate can be performed by placing the cell/solid substrate in a medium that contains the necessary factors for cell survival. The cell/solid substrate is subsequently placed in a 37° C. incubator, that may have controlled humidity and oxygen tension. Frequently, culturing of cells is performed in a bioreactor which acts to tightly regulate the temperature, oxygen and nutrient supply for optimal cell growth on the solid substrate.

The present invention also provides methods for preparing tissue ex vivo. One such embodiment comprises seeding a cell on a solid substrate of the present invention and culturing the cell in a medium that contains the necessary factors for survival. In a particular embodiment the cell is a native progenitor cell. In another embodiment the cell is a transplanted stem cell. In a particular embodiment the cell is an osteoblast. In yet another embodiment, the cell is a hematopoietic stem cell. In still another embodiment, the cell is a hepatocyte. In yet another embodiment, the cell is an embryonic stem cell. In a particular embodiment the condensed nucleic acid of the solid substrate had been delivered in a spatially controlled pattern to the solid substrate. In a preferred embodiment, the condensed nucleic acid comprised by the solid substrate encodes a protein that directs tissue formation. In a particular embodiment of this type, the protein is a growth factor. In an alternative embodiment the protein is a cytokine. In still another embodiment, the condensed nucleic acid comprised by the solid substrate encodes a transcription factor. In yet another embodiment, the condensed nucleic acid comprised by the solid substrate encodes at least two of the following: a growth factor, a transcription factor and a cytokine.

Applications

Tissue engineering aims to create functional tissue replacements for patients suffering from organ loss or tissue failure. To achieve this objective, these tissues will develop from native progenitor cells or transplanted stem cells on a synthetic scaffold that mimics the natural environment. Controlled gene delivery allows spatial variations in gene expression enabling the organization of multiple cell types within a tissue (e.g., nerve cells surrounded by supporting Schwann cells) or provide a directional signal (e.g., neurite extension). Temporal patterns regulate the switching of cell function from an immature to a mature stage. For example, during bone development, osteoblasts switch from an initial proliferation stage to a final mineralization stage. By means of controlled gene delivery, tissues could be engineered by incorporation of appropriate signals into a support scaffold.

An application of spatially controlled gene delivery is nerve regeneration. Neurite extension is guided by gradients in various factors (e.g., NGF, netrins). Spatially controlled expression of these genes can be used to create these concentration gradients. The number and orientation of neurites in response to the chemical gradients are quantified as measures of the cellular response.

An application of temporally controlled gene delivery is bone development, which has been characterized by three stages. The expression of stage-specific genes is examined for effects on mineralized tissue formation. A gene encoding for a growth factor (e.g., TGFβ) is delivered early to increase cell density while a second gene (e.g., osteocalcin) is delivered later to enhance mineralization. Cell density, mineralization, and bone-specific gene expression are used as measures of tissue formation. These applications demonstrate the potential of this approach, which has additional application to numerous cell systems.

The present invention also provides methods of determining the effect of gene expression on cell function. A particular method of this type comprises adding a cell to a well of the microtiter plate comprising multiple wells in which the wells contain condensed nucleic acids encoding a protein. The function of the cell is then monitored. The effect of the expression of the protein encoded by the condensed nucleic acid on cell function is then determined. In another approach, the cells are then assayed for a desired effect, for example, decreased resistance to a chemotherapeutic drug. The DNA molecule encoding the protein causing the response can be identified based on its location in the array. Similar approaches could be used using arrays of antisense oligonucleotides; for example, by preparing DNA polylinker complexes with different DNAs of unknown function, tethering the complexes to a solid support in a microarray format, and adding cells to in an array, cells plated on the array would then be assayed for their ability to respond to certain stimuli. In this manner, one could identify important targets for pharmaceutical intervention (e.g., through the use of pharmaceutical compositions comprised of antisense oligonucleotides or other molecules inhibiting the expression or activity of the target). The invention also provides a useful tool for research; e.g., by selectively inhibiting the expression of different proteins involved in intracellular signaling, one could identify the signaling pathways involved in a cellular response to a stimulus. It is anticipated that the cell function assays of the present invention can be adapted into a format suitable for high-throughput screening.

The present invention further provides methods for regenerating tissue at the site of a wound. In one embodiment, the method comprises contacting a solid substrate of present invention with a cell at the site of the wound. In a preferred embodiment of this type, the condensed nucleic acid comprised by the solid substrate encodes a protein that directs tissue formation. In a particular embodiment of this type, the protein is a growth factor. In an alternative embodiment the protein is a cytokine. In still another embodiment, the condensed nucleic acid comprised by the solid substrate encodes a transcription factor. In yet another embodiment, the condensed nucleic acid comprised by the solid substrate encodes at least two of the following: a growth factor, a transcription factor and a cytokine.

Creating Spatial Patterns for Expression of the Nucleic Acid

Spatial patterning of genes onto surfaces can be performed using a multitude of methodologies. For example, an arrayer may be used to place a specified volume onto a specific spot on the solid substrate. An arrayer is currently being employed to spatially pattern oligonucleotides for gene chips. Alternatively, microfluidics technology can be used to specifically deposit a liquid containing DNA onto a specific region of the solid substrate. In yet another embodiment, the solid substrate can be chemically modified using any of a variety of photolithography techniques.

Specific Embodiments

Thus the present invention combines DNA condensation with polymeric delivery to tether DNA complexes to a surface (FIG. 1), to which cell adhesion can be controlled. DNA is ionically complexed with a cationic peptide to stabilize against degradation and to enhance uptake. A fraction of the cationic peptides that package the DNA are subsequently tethered to the surface of a support substrate, thus maintaining the DNA at the surface through an ionic interaction. The linkages can be designed to be temporary, either through enzymatic degradation of the bifunctional crosslinker or through a reversible tether. The mechanism of uptake may be direct internalization of the plasmid from the surface (e.g., few tethers per complex) or may follow complete degradation of the tethers or bifunctional crosslinkers, which would release the plasmid directly into the cell microenvironment. Controlled delivery and uptake occurs through variations in the type and number of tethers per plasmid.

Figure 2:
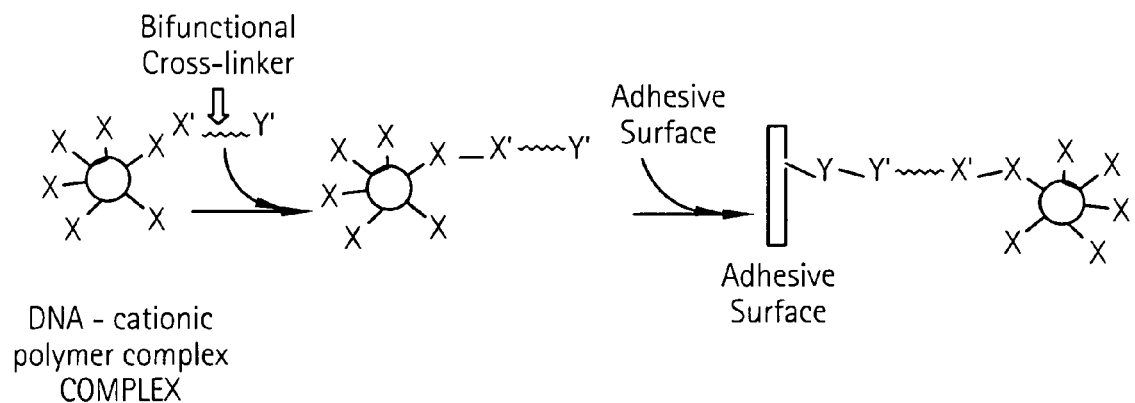
FIG. 2 is a schematic depiction of the coupling of DNA complexes to the surface with a bifunctional cross-linker.

One important aspect of the present invention is based upon the efficient and spatially controlled delivery of nucleic acids to cells cultured on a slide. By themselves, plasmid DNA and oligonucleotide are not efficiently internalized by cells and delivery cannot be spatially controlled; however, packaging the nucleic acids into complexes can overcome these limitations. Complexation with a cationic polymer (e.g., poly-L-lysine, PLL)—a process termed condensation—produces a particle with size ranging from 40–100 nm, a size readily internalized by cells (Mahato et al. (1999) Adv. Genet. 41:95–156). These condensates can contain fusogenic peptides or nuclear localization signals or may be functionalized with receptor ligands to enhance targeting, internalization, and intracellular trafficking of the complex (Cristiano and Curiel (1996) Cancer Gene Ther. 3:49–57). The desired spatial control over delivery is obtained by combining DNA complexation with spotting technology and localized drug delivery. Following condensation, plasmids and oligonucleotides are spotted into domains (100–500 µm) on a slide using, for example, the Affymetrix Pin and Ring. The nucleic acid condensate is retained within the domain by subsequent tethering of the complex to the surface using a bifunctional cross-linker (FIG. 2). One functional group on the cross-linker is coupled to a fraction of the cationic polymers that condense the nucleic acid. The remaining functional group on the bifunctional cross-linker reacts with functional groups on the surface, thus tethering the complex to the surface. The nucleic acid is maintained ionically at the surface for direct delivery into the cell microenvironment. Sustained plasmid delivery from surfaces that support cell adhesion has demonstrated an increased uptake and expression (Shea et al. (1999) supra), likely due to high concentrations at the cell surface (Luo et al. (2000) supra) and prolonged exposure to the plasmid, which provides multiple opportunities for internalization.

In a particular embodiment of the present invention a support surface is employed that has the ability to gel upon implantation into the body (Elisseeff et al. (1999) Plast Reconstr Surg, 104:1014–1022). Implantation of the material results in gelling and filling of the desired space. Cells from the surrounding tissue would then interact with the material and would be presented with the molecule of interest to direct its action, such as for regeneration of a tissue (i.e., tissue engineering), stimulation of an immune response (e.g., cancer therapies), secretion of a therapeutic molecule (i.e., drug delivery), or any other desired cell function.

Example 1 below describes experiments examining tethering complexed polylysine (PLL)/DNA on glass slides, surface densities achieved, and use in cell transfection.

Figure 7:
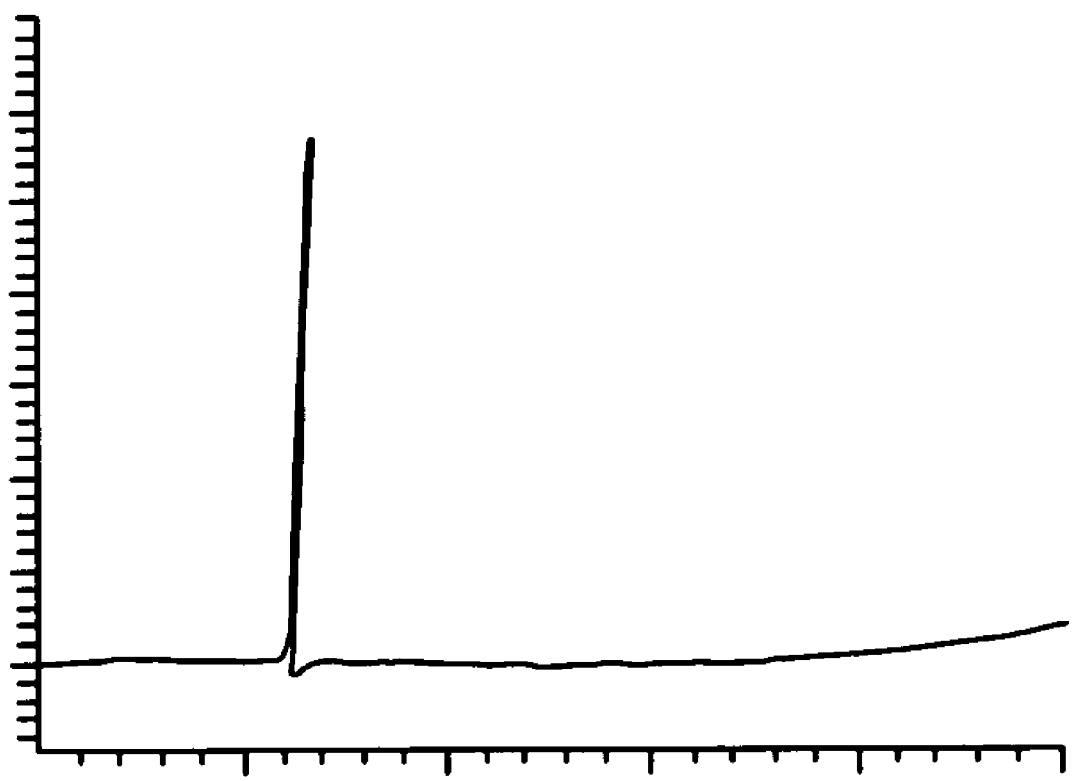
FIG. 7 shows the results of HPLC analysis of the formation of biotinylated $K_{19}$, starting material 1 and the reaction mixture 2. The shift in molecular weight between 1 and 2 and absence of the low molecular weight peak in 2 confirmed that the reaction went to completion.
Figure 8:
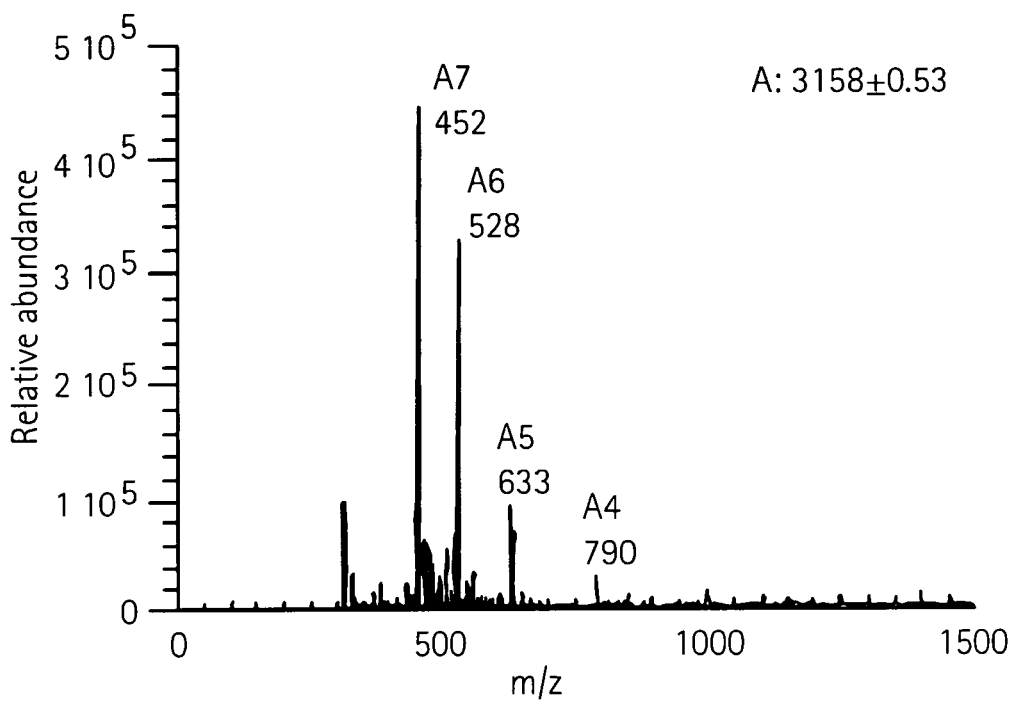
FIG. 8 shows the results of mass spectrometric analysis of the purified reaction mixture of the formation of biotinylated $K_{19}$.

Example 2 describes the synthesis of biotinylated PLL and complexation with DNA. Polylysine was covalently modified with biotin residues either through an N-terminal cysteine side chain ($K_{19}$) or through an amine ($K_{150}$). HPLC analysis of the initial peptide ($K_{19}$) and the peptide reaction mixture ($K_{19}$-B) demonstrated that the reaction proceeded to completion (FIG. 7), as evidenced by the increase in molecular weight in the reaction mixture and the absence of the lower molecular weight $K_{19}$ peak. Mass spectrometry (FIG. 8) suggests that the approach for modifying the peptide $K_{19}$ results in the attachment of a single biotin group. A good correspondence was found between the theoretically expected molecular weight for $K_{19}$ modified with a single biotin (3158 Da), and the experimentally obtained molecular weight (3157.66±0.77 Da). Alternatively, the chemistry employed for modification of $K_{150}$ allows for multiple biotin residues to be attached per PLL. The $K_{150}$-B synthesis resulted in a 3.1:1 molar ratio of biotin to $K_{150}$ by using a 10:1 molar ratio of biotinylation reagent to $K_{150}$ in the reaction mixture.

As described in Example 3, the synthesized biotinylated and non-biotinylated peptides were subsequently analyzed for their ability to complex with DNA using gel electrophoresis. The non-biotinylated peptides ($K_{19}$, $K_{150}$) completely eliminate the electrophoretic mobility at charge ratios of 3.1 and 1.2 respectively (results not shown). However, the presence of the biotin group on the peptide affected the charge ratio at which the mobility is eliminated, which is 4.6 and 4.9 for $K_{19}$-B and $K_{150}$-B respectively. Mixtures of $K_{150}$-B with $K_{19}$ were also examined by gel electrophoresis for DNA complexation at a charge ratio of 5.5:1. The inhibition of mobility was observed for all combinations of the two peptides. The results illustrate that the biotinylated peptides, non-biotinylated peptides, and mixtures of biotinylated and non-biotinylatd peptides are capable of electrostatically neutralizing plasmid DNA and eliminating its electrophoretic mobility.

The availability of the biotin groups on the PLL for tethering to a surface was determined using the affinity of biotin for neutravidin (non-glycosylated avidin). Surface-associated DNA was visualized for DNA complexed with $K_{150}$-B. Fluorescence images taken after the initial incubation on the surface and before the wash demonstrates the presence of complexes across the entire surface (results not shown). Thorough washing of the surfaces resulted in a reduction of the quantity of surface-associated DNA. All subsequent studies used surfaces that were thoroughly washed to ensure binding specificity of the complexes.

Figure 9:
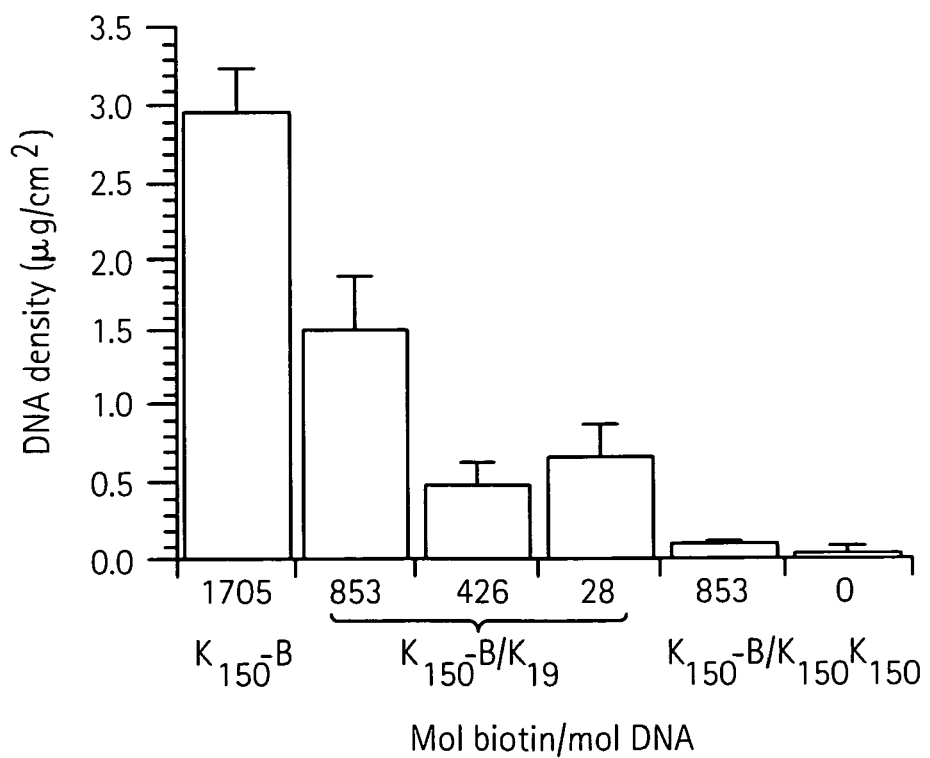
FIG. 9 shows the density of surface-associated DNA for complexes formed by mixing $K_{150}$-B DNA with either $K_{19}$ or $K_{150}$ at a charge ratio of 5.5. The moles of biotin per mole DNA (i.e., average number of biotin groups per complex), which varied from 28 to 1705 for $K_{150}$-B and 217 to 4342 for $K_{19}$-B, are listed beneath each bar. The symbol * indicates statistical significance ($p<0.05$) in the surface densities relative to complexes without biotin.
Figure 10:
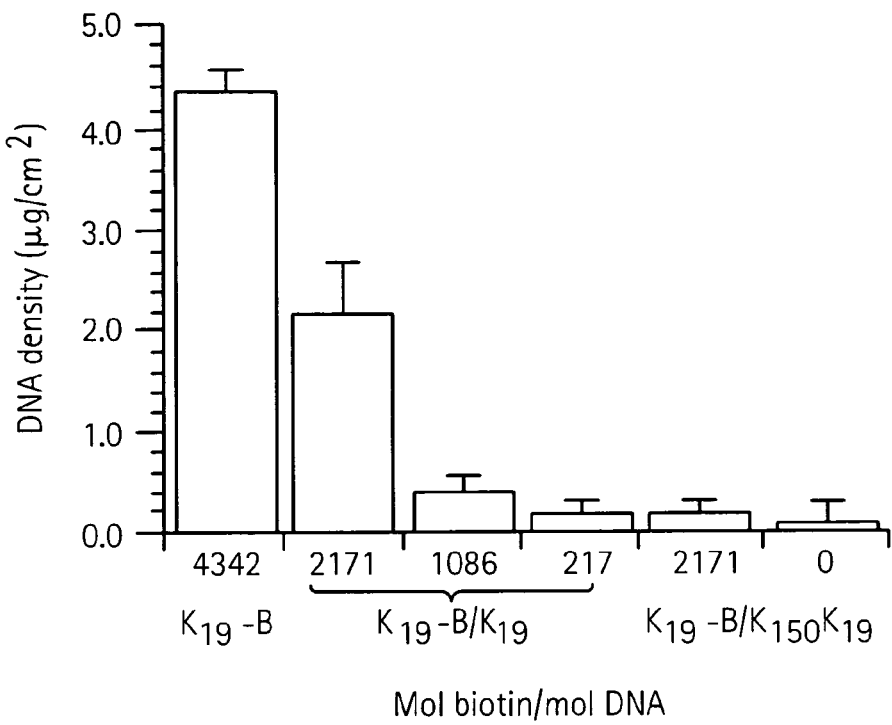
FIG. 10 shows the density of surface-associated DNA for complexes formed by mixing $K_{19}$-B DNA with $K_{150}$-B with either $K_{19}$ or $K_{150}$ at a charge ratio of 5.5 as described in FIG. 11.

The quantity of surface associated DNA was subsequently measured as a function of the PLL peptides and the number of biotin groups per complex. Non-biotinylated peptides used for DNA condensation resulted in low surface densities (<0.1 µg DNA/cm$^2$) due to non-specific adsorption. The use of biotinylated peptides for DNA complexation increased the surface density of DNA relative to the condition of no biotin groups (p<0.05), suggesting that biotin groups are available on the DNA complexes for interactions with the surface-associated neutravidin. The maximal amount of surface-associated DNA was observed for DNA complexes formed solely with biotinylated peptides (p<0.001), with densities of 2.9 and 4.3 µg DNA/cm$^2$ obtained for $K_{150}$-B and $K_{19}$-B respectively (FIGS. 9–10). Complexes formed from either $K_{150}$-B or $K_{19}$-B were calculated to have an average number of biotin groups equal to 1705 and 4342 respectively. These surface densities correspond to a tethering efficiency (mass DNA on surface/mass DNA added) of 24% ($K_{150}$) and 35% ($K_{19}$). For the $K_{150}$-B and $K_{19}$-B, decreasing the amount of DNA incubated on the surface was found to decrease the amount of surface-associated DNA (data not shown). The quantity of surface-associated DNA was also found to decrease as the number of biotin groups in the DNA/PLL complex decreased. The molecular weight of polylysine, both biotinylated and non-biotinylated also affected the quantity of surface-associated DNA. For the biotinylated peptide $K_{150}$-B, fewer numbers of biotin groups were required to obtain an equivalent amount of surface associated DNA as for the peptide $K_{19}$-B. However, the use of the non-biotinylated peptide $K_{19}$ for complexation resulted in increased DNA surface densities relative to the use of $K_{150}$.

Figure 11:
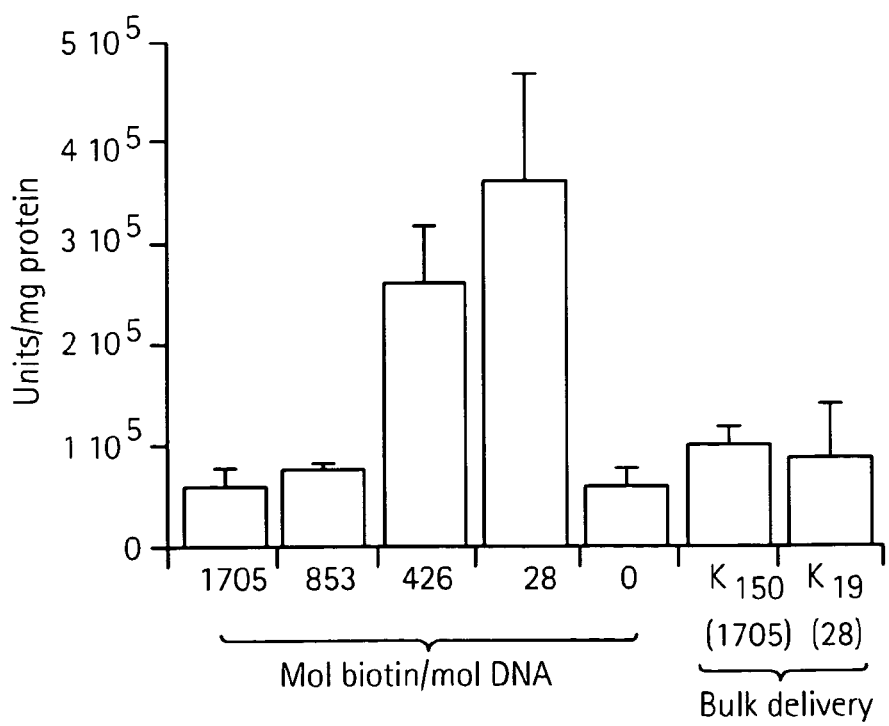
FIG. 11 shows the expression levels achieved by surface mediated transfection after 48 hours of incubation for HEK293T cells determined using an assay for β-galactosidase activity. The symbol * indicates statistical significance in transfection levels ($p<0.05$) relative to both bulk delivery conditions.
Figure 12:
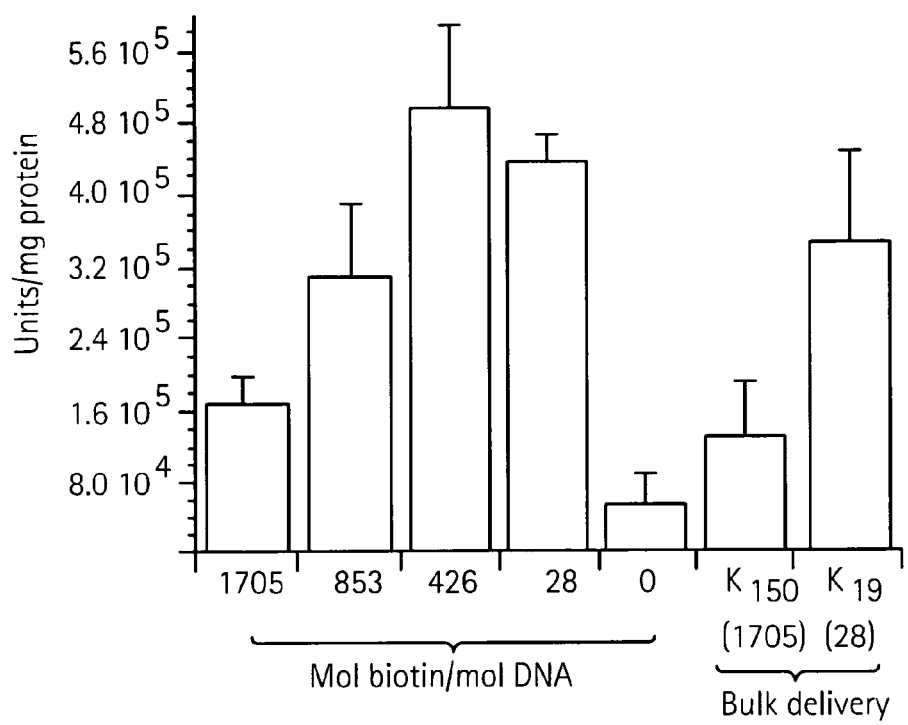
FIG. 12 shows the expression levels achieved by surface mediated transfection after 48 hours of incubation for NIH/3T3 cells as described in FIG. 11.

Culture of HEK293T and NIH/3T3 cells on the DNA modified surfaces led to cellular transfection at 48 hours, with levels of protein production equal to or greater than that obtained by bulk delivery. The transfection experiments (Example 4) used mixtures of $K_{150}$-B and $K_{19}$ for DNA complexation because this combination had an increased amount of surface associated DNA relative to the other peptide mixtures, particularly when the complexes had few numbers of biotin groups. Quantification of protein expression levels for HEK 293T demonstrated that complexes with 28 and 426 biotin groups produced the maximal transfection (FIG. 11), which was statistically greater (p<0.05) than other conditions with greater numbers of biotin groups. Expression levels obtained for surface-associated complexes with 1705 and 853 biotin groups were not significantly different from the control conditions, which consisted of bulk delivery of DNA complexes formed from either $K_{150}$ or $K_{19}$. For bulk delivery, the amount of DNA added in complexes with $K_{150}$ or $K_{19}$ corresponded to the surface quantities of DNA for $K_{150}$-B (1705 biotin groups) and $K_{150}$-B/$K_{19}$ (28 biotin groups), respectively. These conditions were chosen as the control conditions to represent the limiting cases of surface associated delivery regarding DNA quantities (0.7 µg and 0.16 µg) and PLL composition ($K_{150}$, $K_{19}$). For the NIH/3T3 cells (FIG. 12), expression levels obtained by surface associated complexes with 28, 426, and 853 biotin was significantly greater than that obtained with complexes containing 1705 biotin residues (p<0.05). No significant difference between complexes with 28 biotin groups and its bulk control (p>0.05) and 1705 biotin groups and its bulk control (p>0.05) were found. The distribution of transfected cells throughout the cell population also differed between the delivery mechanisms. For bulk delivery, transfected cells were seen throughout the cell population (not shown); however, surface-mediated delivery resulted in cells that were transfected in clusters. Additionally, the location of transfected cells on the surface was consistent with the location of surface-associated DNA seen with the fluorescently-tagged plasmid.

Figure 13:
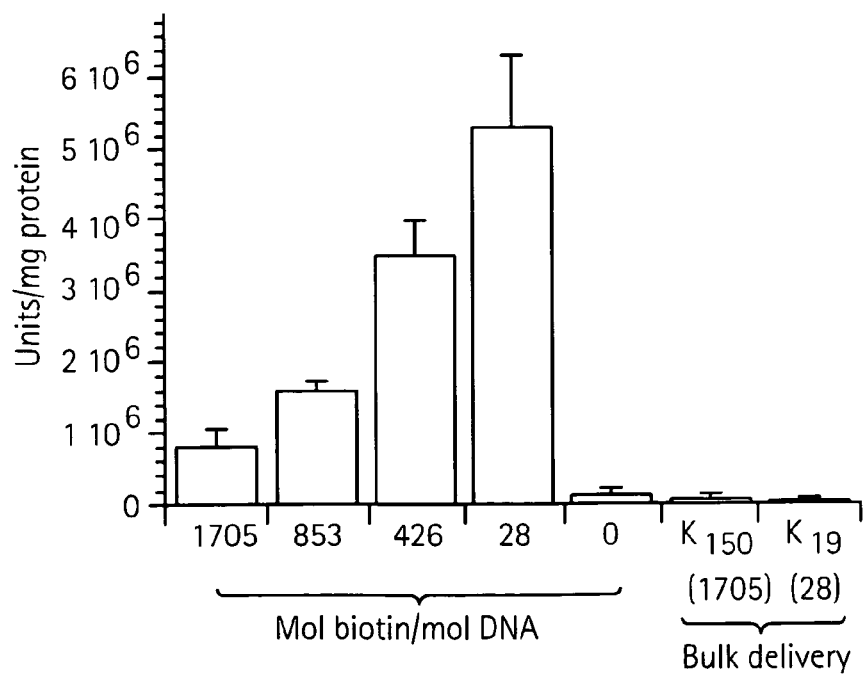
FIG. 13 shows expression levels achieved by surface mediated transfection after 96 hours of incubation for HEK293T cells.
Figure 14:
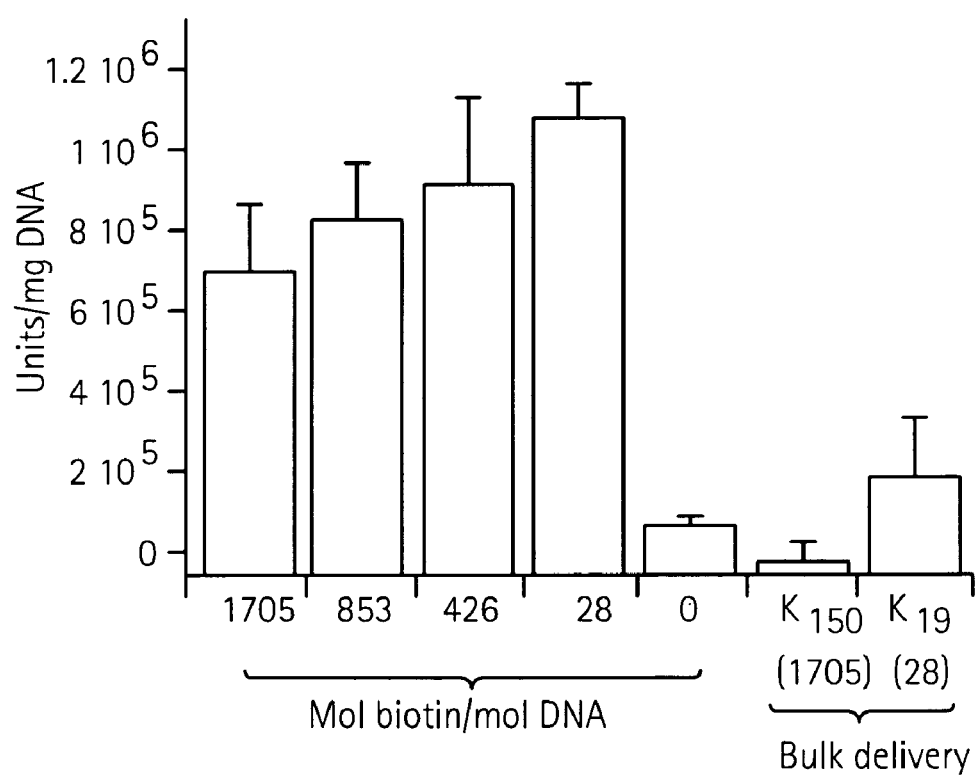
FIG. 14 shows expression levels achieved by surface mediated transfection after 96 hours of incubation for NIH/3T3.

The expression levels of protein at 96 hrs by cells cultured on DNA-modified surfaces increased relative to the that observed at 48 hours and, for all biotinylated DNA complexes, was greater than that obtained by bulk delivery. Maximal expression levels by HEK293T cells was obtained for the complexes containing 28 biotin groups and was statistically significant from all other conditions tested (p<0.05) (FIG. 13). The expression level decreased as the average number of biotin groups on the complex increased (p<0.05). The complexes formed with $K_{150}$-B (1705 biotin groups) had the lowest transfection level of the surface associated delivery; however, the expression level was significantly greater than the bulk control (p<0.01). The expression levels for the NIH/3T3 cells were less dependent on the number of biotin groups, yet the decreasing expression levels for increasing numbers of biotin groups was again observed (FIG. 14). For all conditions tested with surface associated delivery of DNA complexes tethered to the surface with biotin groups, an increased level of transfection was observed relative to the delivery of non-biotinylated DNA complexes and the bulk delivery of DNA complexes (p<0.01).

EXAMPLES

Example 1

Use of Tethered PLL/DNA Complexes

Figure 3:
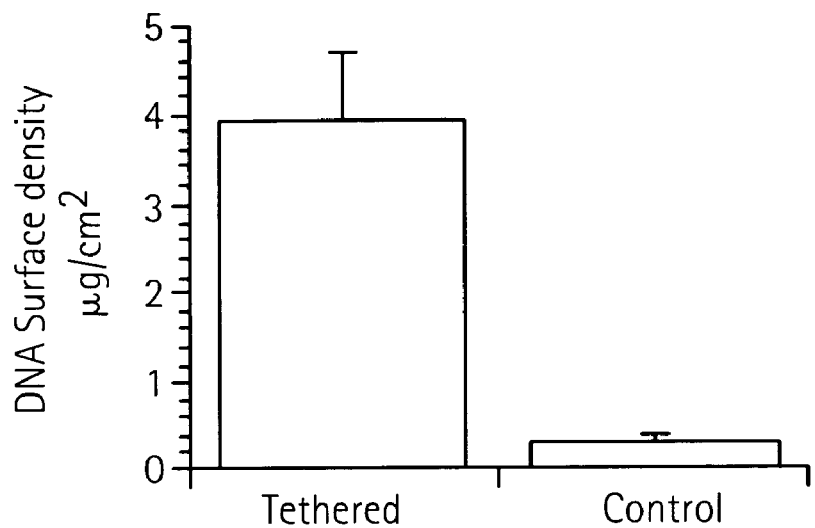
FIG. 3 shows the quantity of surface associated DNA obtained following trypsinization of the slide.

Experiment 1. Plasmid DNA encoding either green fluorescent protein (GFP) or luciferase was complexed with modified poly-L-lysine (PLL) at a ratio of 3.1. PLL was modified by PLL reaction with the bifunctional cross-linker sulfosuccinirnidyl 6-[3'-(2-pyridyldithio)-propionamido] hexanoate (Sulfo-LC-SPDP, Pierce) prior to DNA complexation at a 1:1 molar ratio. The PLL/DNA complexes were subsequently incubated with glass slides that were modified with (3-mercaptopropyl)-trimethoxysilane (MPTS, Sigma) to create pendant thiol groups. Following coupling of PLL/DNA complexes to the slide, the surfaces were extensively washed and treated with trypsin to degrade the PLL and release the DNA into solution. The surface density of DNA was determined to be 3.9±0.78 µg/cm$^2$. Control slides incubated with PLL/DNA complexes without the sulfo-LC-SPDP tether had a surface density of 0.3±0.1 µg/cm$^2$ (FIG. 3).

Figure 4:
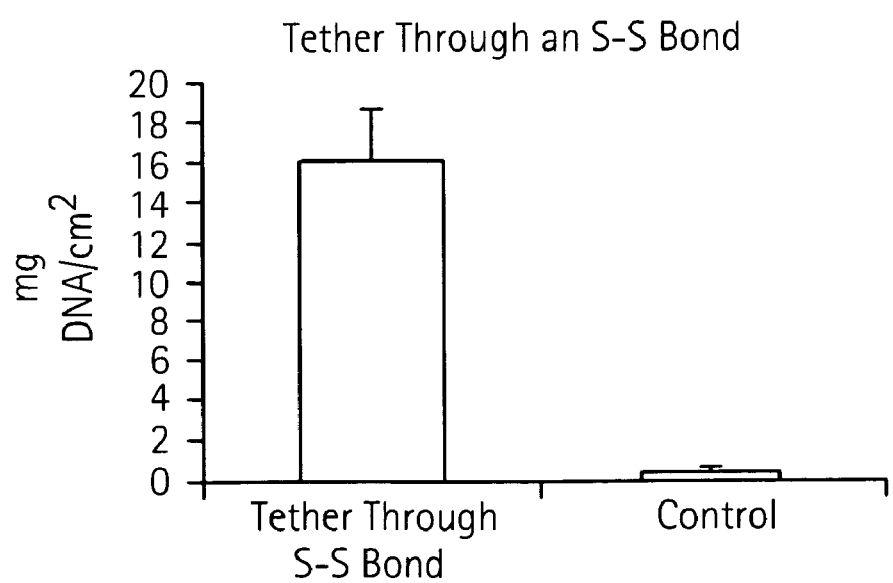
FIG. 4 shows the surface density of tethered DNA/Poly-Lysine-Cys complexes.

Experiment 2. Glass surfaces were prepared with pendant disulfide groups by initially coupling MPTS to create pendant thiol groups. The thiol groups were then reacted with dipyridyldisulfide to form pendant disulfide groups on the surface. Plasmid DNA encoding GFP was mixed for 30 minutes with PLL at a charge ratio of 1:1 (positive to negative). The polylysine chains in the PLL/DNA complexes was covalently coupled to cysteine (which had a protected amino group) using EDC and Sulfo-NHS. The PLL/DNA complex was subsequently tethered to the glass slide through the thiol group on the attached cysteine. The glass slides were washed to remove non-specifically bound complexes. To verify attachment of the PLL/DNA complexes, the slides were then treated with trypsin to degrade the PLL and release the DNA into solution. This quantity of DNA in solution was measured using the Hoechst 33258 fluorometric dye. The amount of DNA released into solution was equal to 17.8±3.51 µg, which corresponds to a surface density of 3.93±0.78 (FIG. 4). The efficiency of incorporation was determined to be 13.8±2.7%. Control slides in which cysteine was not complexed to DNA released 0.63±0.18 µg, which corresponds to a surface density of 0.28±0.08 µg/cm². The amount of DNA tethered to the slides was consistent with the amounts typically used in transfections. The integrity of the released DNA was subsequently analyzed by gel electrophoresis and found to be intact.

NIH3T3 cells were plated into the well of the 96 well dish containing the tethered DNA prepared as described above. Cells were cultured at 37° C. At various times, the cells were examined using a fluorescence microscope for the expression of GFP. Transfected cells were observed within the wells of the dish.

Experiment 3. Tethered DNA complexes were attached to 96 well polystyrene microtiter plates with a streptavidin coating as follows: PLL was reacted with the bifunctional cross-linker sulfo-NHS-LC-Biotin (Pierce) prior to DNA complexing at a 1:1 or 10:1 molar ratio (Biotin:PLL), generating biotinylated PLL. To form the complexes, biotinylated PLL was mixed with DNA at a charge ratio of 3:1 and allowed to self-assemble for 30 minutes. The complexes are formed such that the biotin groups are available for specific coupling to a surface through a streptavidin-biotin interaction. These complexes were subsequently incubated (1–2 hours) in streptavidin modified 96-well plates. Following coupling of PLL/DNA complexes to the wells, the surfaces were extensively washed with TNBS buffer and treated with trypsin to degrade the PLL and release the DNA into solution. The number of biotin groups available for coupling controlled the surface density of DNA. Experiments using 200, 100, and 50 moles biotinylated PLL/moles DNA and the 1:1 molar ratio (Biotin:PLL) PLL, yielded the following surface densities: 1.16±0.01 µg/cm², 2.54±0.05 µg/cm², 2.17±0.08 µg/cm² respectively. Similar experiments with the 10:1 molar ratio yielded surface densities of 2.14±0.16 µg/cm², 0.32±0.05 µg/cm², and 0.41±0.06 µg/cm². Control slides incubated with PLL/DNA complexes without the sulfo-LC-Biotin tether had a surface density of 0.06±0.02 µg/cm².

Example 2

Synthesis of Biotinylated Poly-Lysine

Plasmid DNA encoding for β-galactosidase (pNGVL1-β-gal) was purified from bacteria culture using Qiagen (Santa Clara, Calif.) reagents and stored in Tris-EDTA buffer solution (10 mM Tris, 1 mM EDTA, pH=7.4). Fluorescein tagged β-galactosidase vector (Fl-β-gal) was purchased from Gene Therapy Systems (San Diego, Calif.). Two polylysine (PLL) peptides were used for DNA complexation: Cys-Trp-Lys$_{19}$ (K$_{19}$, BioPeptide, San Diego, Calif.) and Lys$_{150}$ (K$_{150}$, average molecular weight of 20,000, Sigma, St Louis, Mo.). Avidin and biotin reagents for peptide modification and surface tethering were purchased from Pierce (Rockford, Ill.). All other reagents were obtained from Fisher Scientific (Fairlawn, N.J.) unless otherwise noted.

Peptide K$_{19}$ was modified with a biotin group through the terminal cysteine residue by reaction of the sulfhydryl group with the iodoacetyl group of the biotinylation reagent, EZ-link-PEO-Iodoacetyl-Biotin. K$_{19}$ (10 mg) was dissolved in 850 µL of buffer (50 mM Tris, 5 mM EDTA, pH=8.3) that was previously bubbled with nitrogen gas. The EZ-link-PEO-Iodoacetyl-Biotin (3.8 mg) was also dissolved in 150 µL of buffer (0.1 M Sodium Phosphate, 5 mM EDTA, pH=6.0). The biotin solution was added dropwise to the peptide solution, mixed gently, covered with aluminum foil and incubated for 90 minutes. The starting peptide solution and the reaction mixture were analyzed by HPLC to determine if the reaction had gone to completion. The starting peptide solution and the reaction mixture were resolved by injecting 20 µg through a C18 RP-HPLC column eluted with water (0.1% trifluoroacetic acid (TFA)) and a acetonitrile gradient (0.1% TFA, 0 to 95% over 50 minutes at 60° C.) while detecting the absorbance at 260 nm. For purification, sephadex (G15) was equilibrated in deionized water for 30 minutes prior to packing in a glass column (2 cm diameter× 12 cm height). The reaction mixture was passed though the column using deionized water. Twenty fractions were collected and the presence of the tryptophan side chain was examined by measuring the absorbance at 260 nm (Beckman Instruments Inc., Fullerton, Calif.). The fractions with the greatest absorbance at 260 nm were lyophilized (Labconco Corp., Kansas City, Mo.) and analyzed by mass spectrometry. The purified biotinylated peptide (K$_{19}$-B) was stored as a powder at −20° C.

Peptide K$_{150}$ was biotinylated using succinimide ester (NHS)/amine chemistry. K$_{150}$ (10 mg) was dissolved in 1 mL of phosphate buffered saline (PBS, pH=7) and EZ-link-Sulfo-NHS-LC-Biotin (2.8 mg) was added directly to the solution, mixed gently and incubated for 2 hours at 4° C. The reaction mixture was purified using dialysis cassettes immersed in deionized water. The dialyzed product was further purified using a monomeric avidin column to separate the biotinylated components from non-biotinylated species. The biotinylated product was eluted with 10 ml of a 10 mM biotin solution and dialyzed to remove the unconjugated biotin. The purified biotinylated peptide (K$_{150}$-B) was then lyophilized and stored as a powder at −20° C. The degree of biotinylation of K$_{150}$-B was determined by quantifying the mole ratio of biotin to K$_{150}$ using 2[4'-hydroxyazobenzene]-benzoic acid (HABA). The absorbance at 500 nm of a HABA/avidin solution in PBS was recorded before and after the addition of the K$_{150}$-B and used to calculate the molar ratio of biotin to K$_{150}$.

Example 3

Complex Formation and Surface Tethering

The ability of the biotinylated and non-biotinylated polylysine (K$_{150}$, K$_{150}$-B, K$_{19}$, K$_{19}$-B) synthesized as described above, to condense DNA was assessed by gel electrophoresis. Biotinylated and non-biotinylated peptides were mixed and added in a stepwise manner (1 µL of 1 mg/mL) to a DNA solution (200 µL of µg/mL). After each addition step, the solution was vortexed for 4 seconds, incubated for 10 min and a sample (10 µL) removed. Upon complete addition of peptide, trypsin was added to digest the polylysine. Gel electrophoresis was performed to assess the extent of complex formation for the samples and the trypsin-digested DNA solution.

DNA/PLL complexes were incubated on surfaces to specifically tether the complexes through the biotin-neutravidin binding. DNA (90 µL of 44.4 µg/mL) was complexed at a charge ratio (+/−) of 5.5:1 with the four peptides (K$_{150}$, K$_{150}$-B, K$_{19}$, or K$_{19}$-B) individually or with mixtures of biotinylated and non-biotinylated peptides. The number of tethers on each complex is varied by mixing biotinylated and non-biotinylated PLLs prior to complexation with DNA. Complexes were incubated after mixing for 30 min at room temperature and then allowed to bind to pre-washed neutravidin coated surfaces for 2 hours. The unbound complexes were then removed from the wells and washed with tris-buffered saline (TBS). The surface quantities of DNA were determined by incubating with trypsin (100 µL) at 37°

C. for 2 hours to degrade the PLL and release the DNA into solution. The quantity of DNA was measured with a fluorometer (Turner Designs TD-360) using the Hoechst dye. Tethered DNA complexes were visualized by fluorescence microscopy using the Fl-β-gal vector before and after washing with TBS.

Example 4

Cell Culture and Transfection

Transfection of cells on the DNA-modified surfaces, produced as described above, was examined using a β-galactosidase plasmid and two cell lines (HEK293T and NIH/3T3). Polyethyleneimine (PEI, 22 kDa, MBI-Fermentas, Hanover, Md., 0.5 μL of 10 μM) was added to DNA-modified surfaces and incubated for 5 min. Cells were then plated and cultured on the surfaces for 48–96 hours and then lysed for assay of β-galactosidase enzyme activities (Promega, Madison, Wis.) and protein levels (BioRad, Hercules, Calif.). Alternatively, cells were stained with X-gal to determine the location of transfected cells. HEK293T and NIH/3T3 were cultured at 37° C. and 5% $CO_2$ in Dulbecco's modified eagle medium (DMEM, Life Technologies, Gaithersburg, Md.) supplemented with 10% heat inactivated FBS and 1% penicillin/streptomycin. Control experiments to characterize the effectiveness of surface-mediated delivery were performed by using bulk delivery of DNA complexed with the non-biotinylated $K_{150}$ or $K_{19}$. For bulk delivery of $K_{150}$/DNA complexes, the quantity of DNA delivered was determined based on the amount of surface associated DNA obtained when DNA was complexed only with $K_{150}$-B. For bulk delivery of $K_{19}$/DNA, the quantity of DNA delivered was determined based on the amount of surface-associated DNA obtained when DNA was complexed with a mixture of $K_{150}$-B/$K_{19}$, which had a predominance of $K_{19}$ over $K_{150}$-B. For the bulk delivery experiments, HEK293T and NIH3T3 cells were plated at one day prior to transfection and cultured in complete media.

Example 5

Gene Delivery Through Adsorbed DNA Complexes

Materials and Methods

Materials

Plasmid DNA encoding for luciferase or enhanced green fluorescent protein (GFP) with a CMV promoter was purified from bacteria culture using Qiagen (Santa Clara, Calif.) reagents and stored in Tris-EDTA buffer (10 mM Tris, 1 mM EDTA, pH=7.4). Branched polyethylenimine (PEI, 25 kDa) was purchased from Aldrich (St. Louis, Mo.). Lipofectamine 2000 was purchased from Invitrogen (Gaithersburg, Md.). All other reagents were obtained from Fisher Scientific (Fairlawn, N.J.) unless otherwise noted.

Surface Modification

Tissue culture polystyrene (PS) was used as provided or after modification with fetal bovine serum (FBS-PS). Modification was characterized using X-ray Photoelectron Spectroscopy (XPS), which uses x-rays to eject electrons, which can be measured and correlated to chemical states. XPS spectra were recorded using an Omicron ESCAProbe system with an Al/Mf anode X-ray source. The wettability of the surfaces was determined through measurement of the contact angle of water droplets on the surface. Contact angles were determined at room temperature with a goniometer (Ramé-Hart), which is equipped with a camera system and DROPimage Standard software. A water droplet was dispensed and angle measurements were recorded as the angle between the surface and tangent at the droplet contact with the surface.

Complex Formation and Immobilization

Addition of cationic polymers or lipids to plasmid DNA results in self-assembly to form colloidal polyplexes and lipoplexes, respectively. The complexing agents used were the branched cationic polymer polyethylenimine (PEI) and Lipofectamine 2000. Complexes with PEI, termed polyplexes, were formed at the desired N/P (range 5–25), while DNA complexed with Lipofectamine 2000, termed lipoplexes, were formed at ratios of DNA:lipid (μg:μL, range 0.5–5). For polyplexes, polymer solution (60 μL in tris buffered saline) is added drop wise to DNA (60 μL), vortexed, and incubated for 15 minutes at room temperature. For lipoplexes, lipid (50 μL) is added drop wise to DNA, mixed by gentle pipetting, and incubated for 20 minutes.

Lipoplexes were formed in serum free cell growth media. Zeta potential and z-average diameter were measured with a Zetasizer Nano ZS (Malvern, Worcestershire, UK). Complexes were immobilized by incubation on either untreated or serum-coated tissue culture polystyrene. Polystyrene (PS, 96-well strip plate) was serum-coated (FBS-PS) by incubation with heat inactivated fetal bovine serum (200 μL, 10% in PBS, pH=7.4) for 2 hours, followed by two wash steps with PBS. Complexes were immobilized immediately following complex formation by incubation of DNA complexes (100 μL) with the substrate for 1–24 hours, which was followed by two wash steps.

Quantification of Immobilized DNA and DNA Release

The binding and release of DNA from the substrates was monitored using plasmid DNA radiolabeled with $^{32}P$ dATP. Briefly, a nick translation kit (Amersham Pharmacia Biotech, Piscataway, N.Y.) was used following the manufacturer's protocol with minor modifications (Segura et al. 2003). Following immobilization and washing, complex surface density was determined by immersing individual wells in scintillation cocktail (5 mL, ScintiVerse II) for measurement with a scintillation counter. The counts were correlated to DNA mass using a standard curve. To determine the release profile, substrates with immobilized DNA were incubated with PBS or conditioned media (200 μL) at 37° C. in a humid chamber. Conditioned media was collected from cultures (at least 24 hours) of NIH/3T3 cells. At predetermined time points, half of the solution (100 μL) was removed and replaced with fresh solution. The activity of the collected sample was measured in a scintillation counter. At the final time point, the counts remaining on the substrate were also determined. The percentage of DNA released was calculated as the ratio of the cumulative counts released through a given time divided by the total counts initially on the substrate.

Cell Culture and Transfection

Transfection studies were performed with NIH/3T3 (ATCC) cells cultured at 37° C. and 5% $CO_2$ in DMEM supplemented with 5% sodium pyruvate, 1.5 g NaHCO3 and 10% FBS. Cells were seeded at a density of 5,000 cells per well in 96-well plates. For substrate-mediated delivery, cells were seeded immediately following complex immobilization and wash. Control studies were performed with bolus delivery to cells plated in a 48-well dish at a density of 15,000 cells/well and allowed to incubate overnight. The quantity of DNA delivered as a bolus was equivalent to the amount of DNA immobilized to the substrate, with normalization to the larger well. Complexes were formed as described above, but with a final volume of 30 µL. Transfection was analyzed following a 48-hour culture.

Transfection was characterized through the extent of transgene expression (luciferase) and the number of transfected cells (GFP). The extent of transgene expression was quantified by measuring the luciferase activity using the Luciferase Assay System (Promega, Madison, Wis.). Cells were lysed and assayed for enzymatic activity after 48 hours. The luminometer was set for a 3 second delay and an integration of the signal for 10 seconds. Transfected cells were visualized and manually counted using a GFP plasmid and epifluorescence microscopy (Leica, Bannockburn, Ill.) with a FITC filter and equipped with a digital camera. The percentage of transfected cells was calculated as the ratio of the number of transfected cells divided by total cell number, which was determined by manual counting of bright field images.

Confocal Microscopy

DNA complexes were fluorescently labeled with tetramethyl rhodamine (Mirus). Polyplexes were then immobilized followed by cell seeding. Cells were cultured for 16 hours, and then labeled with the cytoplasmic stain fluorescein diacetate (Sigma, St. Louis, Mo.). The distribution of cell and complexes on the substrate was visualized with confocal microscopy (Leica).

PLG Disk

The biomaterial poly(lactide-co-glycolide) was fabricated into a disk using a gas foaming process (Jang and Shea 2003; Nof and Shea 2002). After fabrication, disks were coated with serum and complexes were incubated with the disk for 24 hours as described. After washing, cells were seeded onto the disk. Transgene expression was determined using the luciferase assay as previously described. Transfected cells were visualized by delivering a plasmid encoding for nuclear targeted β-galactosidase and staining with X-gal following culture (Shea et al. 1999).

Results

Complex Formation and Surface Modification

The z-average diameter and zeta potential of DNA complexes, which may impact substrate immobilization and transfection, were measured and are consistent with published reports. The zaverage diameter (dz) of the polyplexes decreased with increasing amounts of cationic polymer in the complex, with mean diameters ranging from 1062 nm to 121 nm for N/P ratios of 5 and 25, respectively (FIG. 15A). Increasing the amount of cationic polymer led to increases in the zeta potential of polyplexes, which ranged from −14.33 mV to a maximum of 21.21 mV at an N/P of 10 (FIG. 15B). N/P ratios greater than 10 did not significantly affect the zeta potential (p>0.05). For lipoplexes, the mean dz ranged from 603±104 nm to 1089±340 nm for increasing amounts of lipid (FIG. 15C). For DNA:lipid ratios greater than 1:2, increasing the amount of lipid had no significant effect on the zeta potential (p>0.05), which averaged −50 mV (FIG. 15D).

Figure 16:
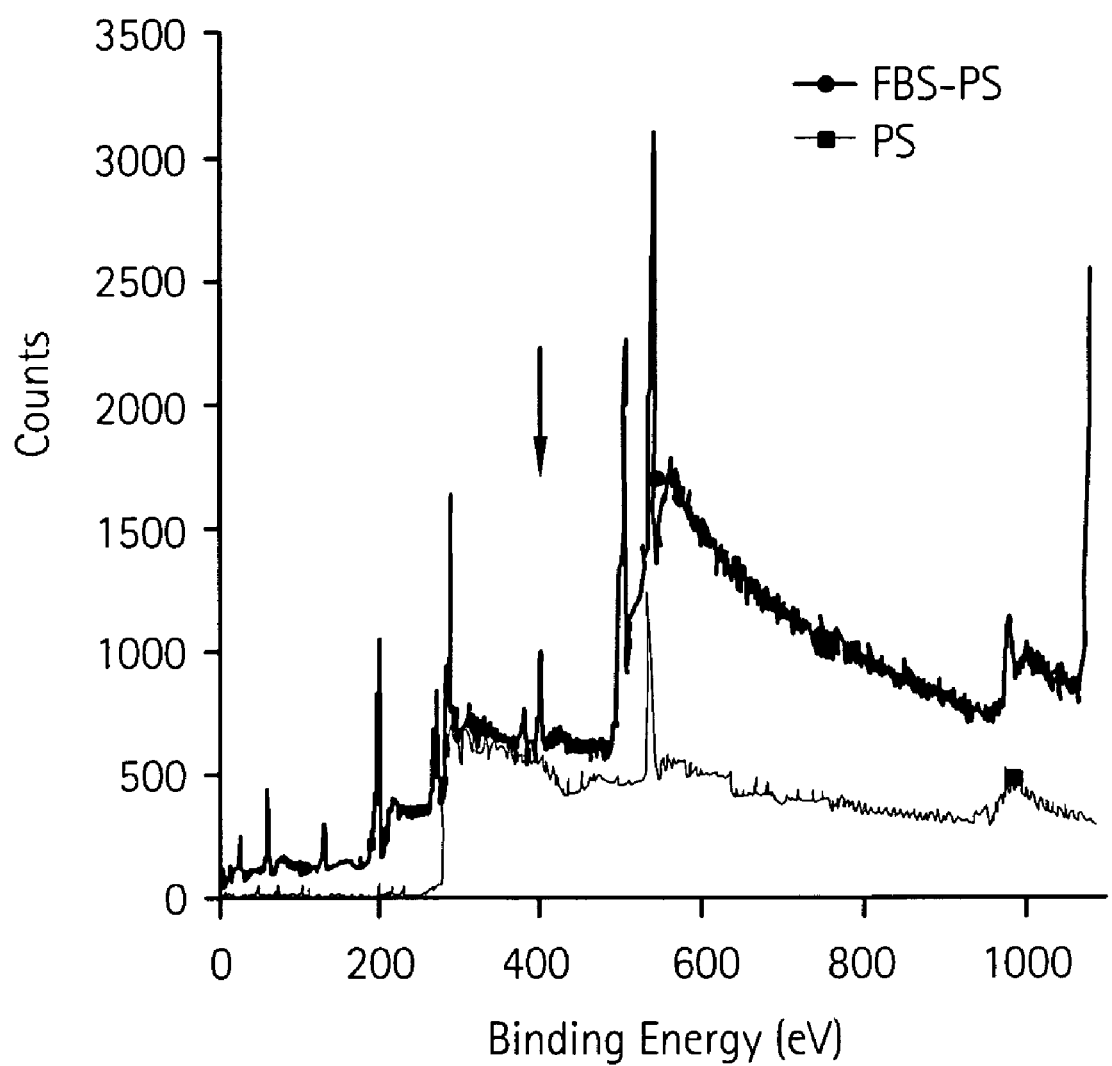
FIG. 16 Shows the X-ray photoelectron spectrum of polystyrene and a serum modified polystyrene surfaces. The peak denoted by the arrow indicates the presence of nitrogen on the substrate.

The altered surface chemistry induced by serum coating was confirmed with X-ray photon spectroscopy (XPS) and contact angle measurements. The XPS spectrum indicates that nitrogen groups are present on FBS-PS, and not on PS (FIG. 16). Serum coating also increased the wettability of the surfaces as determined by contact angle measurements (Table 1). The FBS treated surfaces had a low contact angle (<15°) relative to the unmodified PS surface (48°).

Complex Immobilization and Stability

Figure 17A:
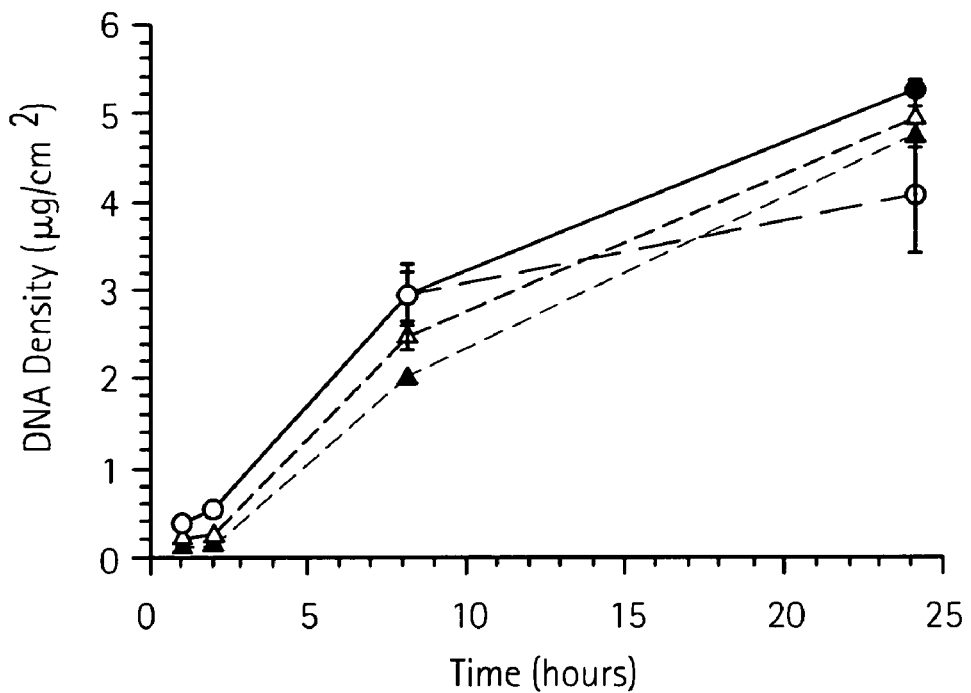
FIG. 17 shows DNA deposition and stability. (A) Polyplexes (circles) and lipoplexes (triangles) were deposited onto polystyrene (●, ▲) and serum coated polystyrene (○, ∆) for 24 hours. Substrates were incubated with 2 μg of DNA. (B) Immobilized polyplexes and lipoplexes were exposed to phosphate buffered saline (PBS, pH=7.4) at 37° C. Data is presented as average ±standard deviation of the mean. * indicates $p<0.05$ relative to FBS-PS deposition of polyplexes after 24 hours. ** indicates $p<0.05$ relative to lipoplexes released from PS at 8 days.
Figure 17B:
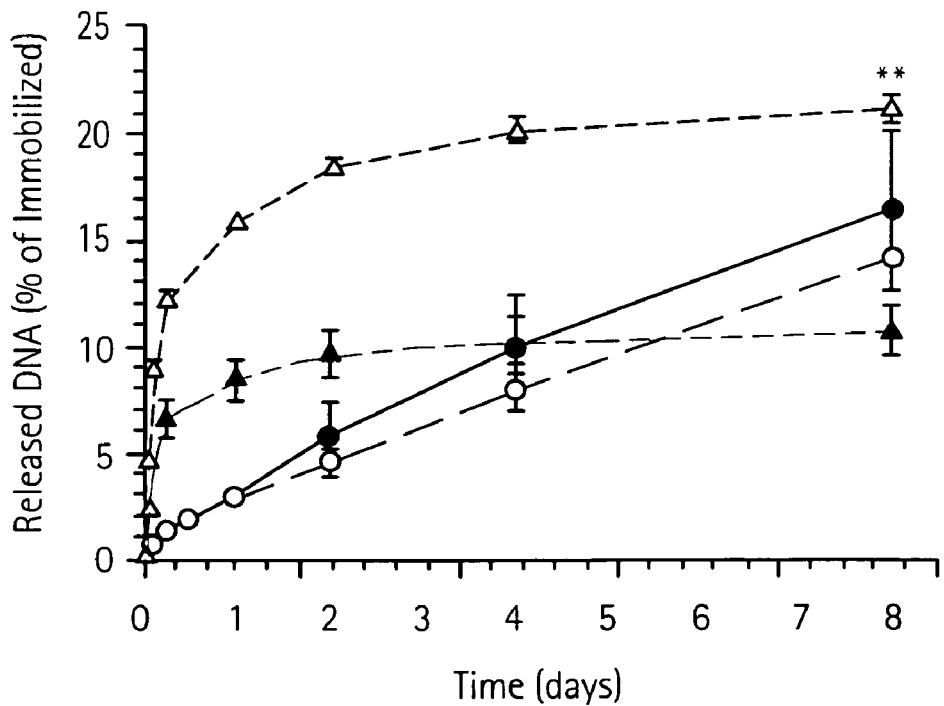
Figure 18A:
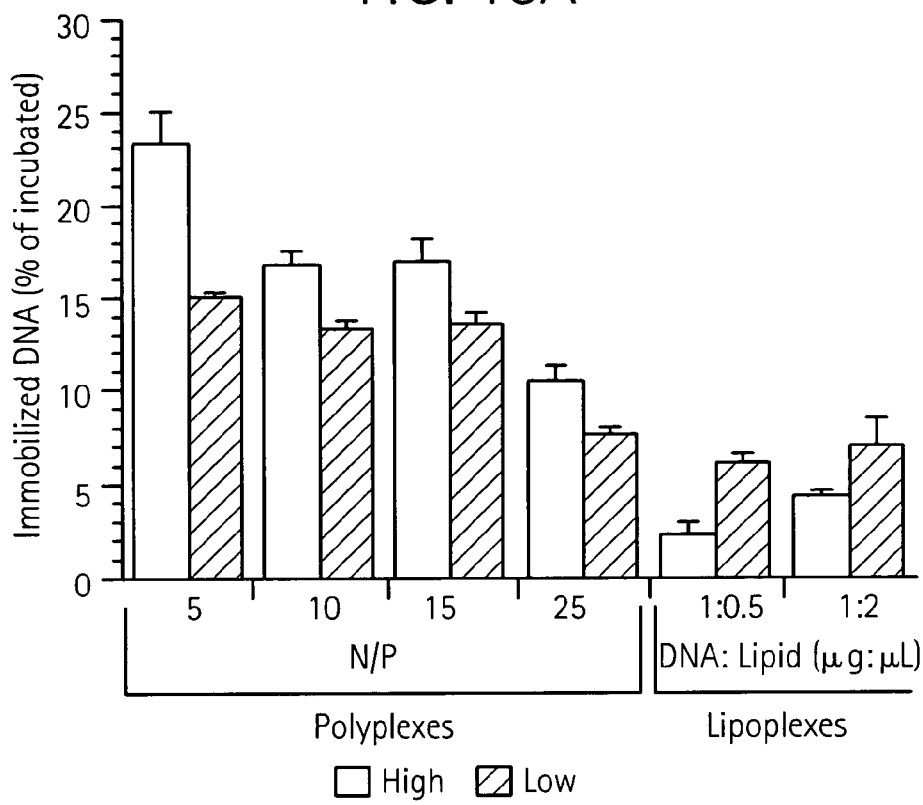
FIG. 18 shows DNA adsorption to surface. Polyplexes and lipoplexes were incubated on (A) PS and (B) FBS-PS surfaces for 2 hours. Black bars indicated 2 μg and gray bars indicated 0.5 μg of DNA incubated on the surface. Data is presented as average ±standard deviation of the mean. High doses have $p<0.05$ relative to corresponding low doses at the same N/P (A). * indicates $p<0.05$ relative other polyplex conditions.
Figure 18B:
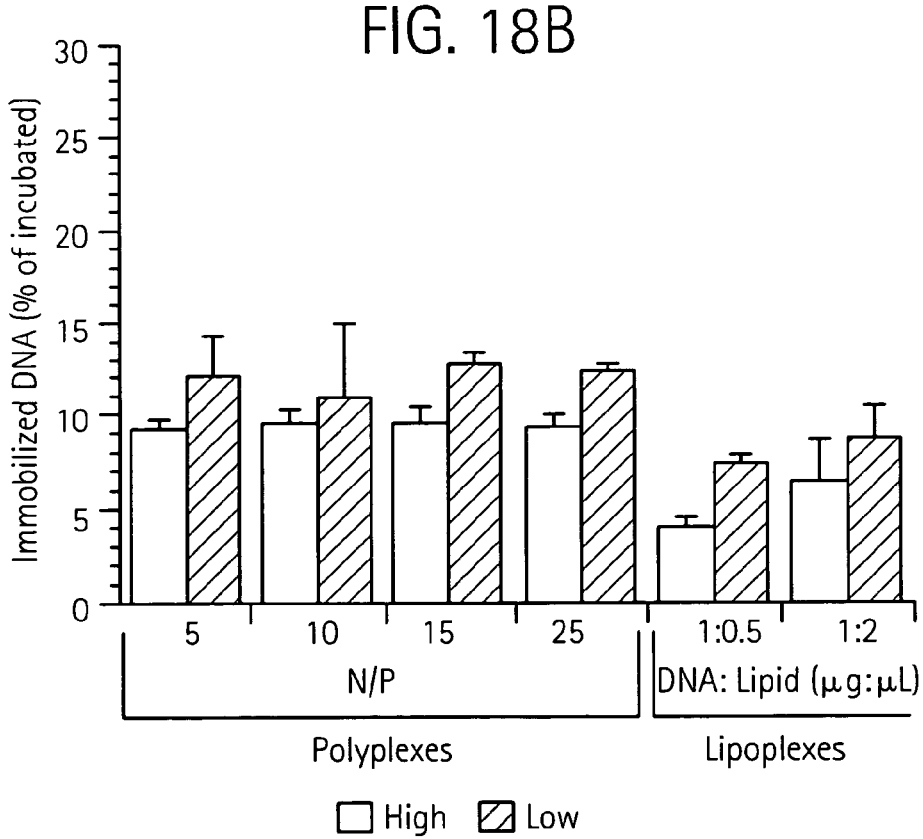

The amount of DNA immobilized to the surfaces increased with time of incubation on the surface and was dependent upon the chemical properties of the surface and DNA complex. Incubation of DNA complexes with the substrate for 24 hours resulted in surface densities of at least 4 µg/cm2, which corresponds to immobilization of more than 60% of the DNA (FIG. 17A). Polyplex deposition on PS and FBS-PS occurred at similar rates during the first 8 hours of incubation; however, deposition onto FBS-PS slowed relative to PS during the final 16 hours, resulting in surface densities of 4.1 µg/cm2 and 5.3 µg/cm2, respectively. Lipoplex binding to the substrate was not substantially affected by the surface properties during the 24-hour incubation (p>0.05). The retention of complexes on both PS and FBS-PS substrates during incubation in PBS was unaffected by surface modification. For polyplexes, incubation in PBS resulted in 16.5% and 14.3% (p>0.05) release after 8 days from PS and FBS-PS, respectively (FIG. 17B). For lipoplexes, incubation in PBS resulted in 10.5% and 21.4% (p>0.05) release after 8 days from PS and FBS-PS, respectively (FIG. 17B). The release of polyplexes gradually increases during the 8-day incubation in PBS, whereas lipoplexes reach maximal release after 2 to 4 days. Transfection experiments typically involve cell culture for 24–96 hours, which corresponds to release of 2.75% to 20% of immobilized DNA. Increasing the quantity of DNA incubated with the substrate resulted in increased quantities of immobilized DNA; however, the percentage of DNA immobilized after a 2-hour incubation is dependent upon surface modification, and complex properties. For polyplexes immobilized to PS substrates, increasing the quantity of DNA incubated on the surface led to a greater percentage immobilized for all N/P ratios (FIG. 18A). Furthermore, increasing the N/P ratio resulted in decreasing quantities of immobilized DNA. Conversely, polyplexes immobilized to FBS-PS substrates exhibited no dependence on DNA quantities or N/P ratio (p>0.05). Lipoplex binding to PS substrates exhibited a dependence on DNA quantities, with lower quantities binding more effectively than higher quantities, and the concentration dependence was significant for FBS-PS at the lower lipid content. For both PS and FBS-PS, the lipid content of the complexes did not affect the percentage bound to the substrate.

Cellular Transfection

Cells cultured on substrates with immobilized polyplexes and lipoplexes were transfected and the extent of transgene expression depended upon substrate modification, and complex formulation. Polyplexes and lipoplexes immobilized to FBS-PS substrates yielded equal or greater transgene expression than delivery from PS. For polyplexes immobilized at low densities.

Figure 19A:
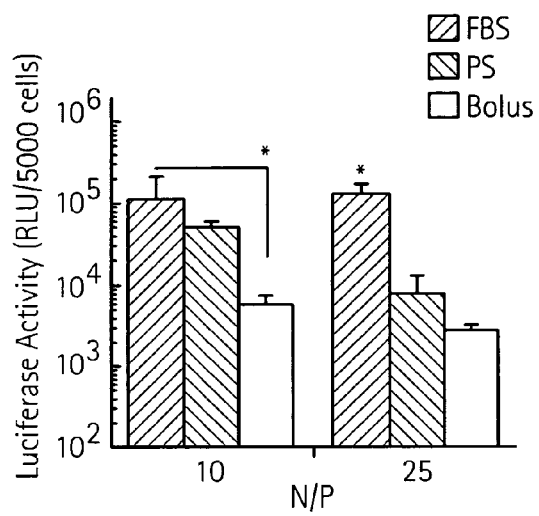
FIG. 19 shows transgene expression by substrate-mediated delivery. (A, B) Polyplexes and (C, D) lipoplexes with plasmid encoding for luciferase were incubated on substrates at low (0.5 μg; A, C) and high (2.0 μg; B, D) doses for 2 hours. Bolus delivery used equivalent amounts of DNA that were immobilized to the substrate: (A) 0.2 μg/cm2, (B) 0.5 μg/cm2, (C) 0.25 μg/cm2 and (D) 0.1 μg/cm2. Activity was normalized to the number of cells seeded. Data is presented as average ±standard deviation of the mean. * indicates $p<0.05$ relative to other delivery methods for that condition. ** indicates $p<0.05$ at different complex conditions.
Figure 19B:
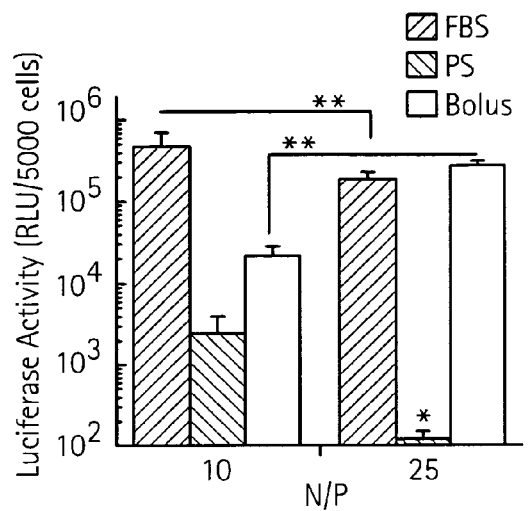

FBS-PS substrates yielded 17-fold greater transgene expression than PS at an N/P of 25, and similar levels for N/P equal to 10 (FIG. 19A). For higher densities of immobilized polyplexes, transgene expression on FBS-PS was increased 194-fold and 1638-fold compared to PS surfaces for N/P equal to 10 and 25, respectively (FIG. 19B). Polyplex delivery from FBS-PS surfaces enhanced expression 20 to 49-fold relative to equivalent doses delivered in bolus, with the exception that the highest dose and N/P ratio providing similar expression levels.

Figure 19C:
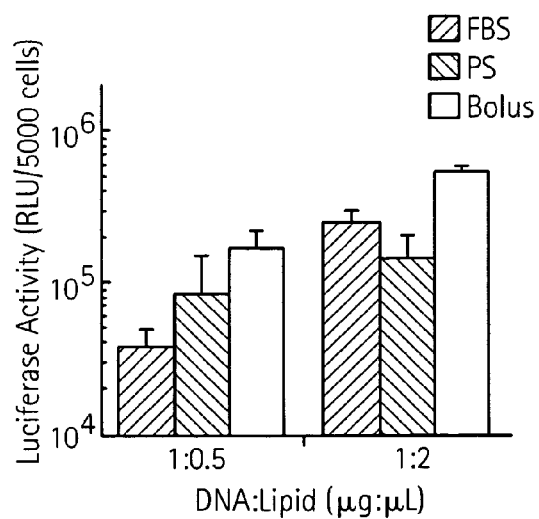
Figure 19D:
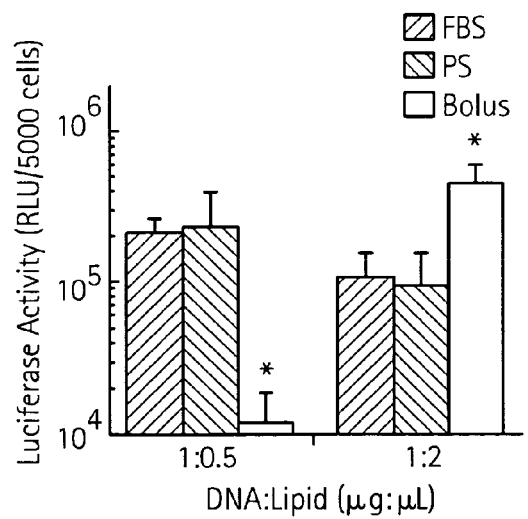

Lipoplex delivery from PS and serum-modified PS yielded equal levels of luciferase activity under similar dosage and complex conditions. At low dose conditions, increasing the lipid content of the complexes led to a 6.5 fold enhancement in luciferase activity (FIG. 19C), which was not observed at the higher dose (FIG. 19D). For lipoplexes with the lowest lipid content and at the highest dose, an 18-fold enhancement in activity was observed from serum-modified surfaces when compared to bolus delivery. Otherwise, transgene expression was similar between substrate-mediated and bolus delivery.

Figure 20A:
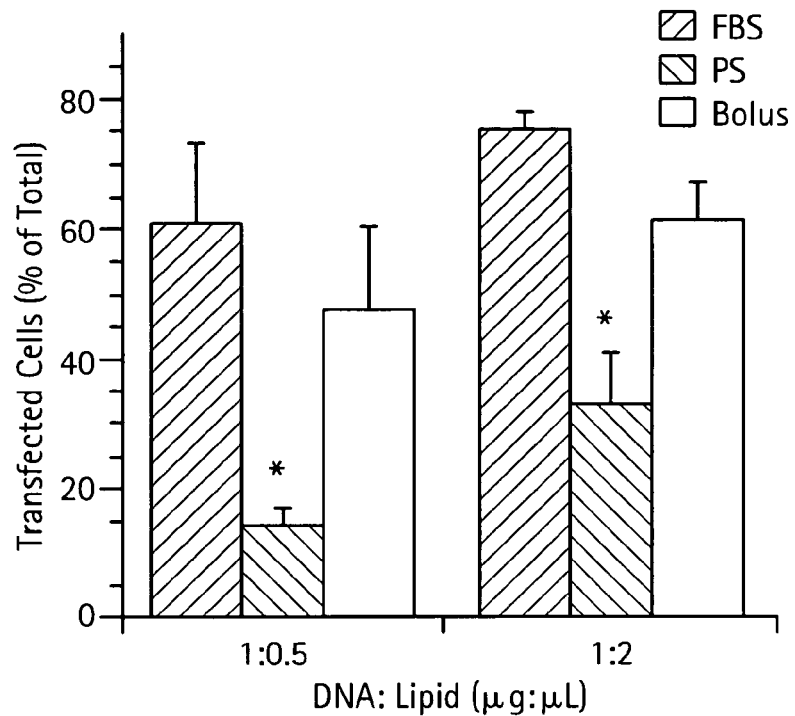
FIG. 20 shows transfected cell numbers by substrate-mediated delivery. Lipoplexes with plasmid encoding for GFP were incubated on substrates with quantities of (A) 0.5 μg and (B) 2 μg for 2 hours. Bolus delivery used equivalent amounts of DNA that were immobilized to the substrate: (A) 0.25 μg/cm2 and (B) 0.1 μg/cm2. Data is presented as average ±standard deviation of the mean. * indicates $p<0.05$ relative to the other delivery methods for that condition.
Figure 20B:
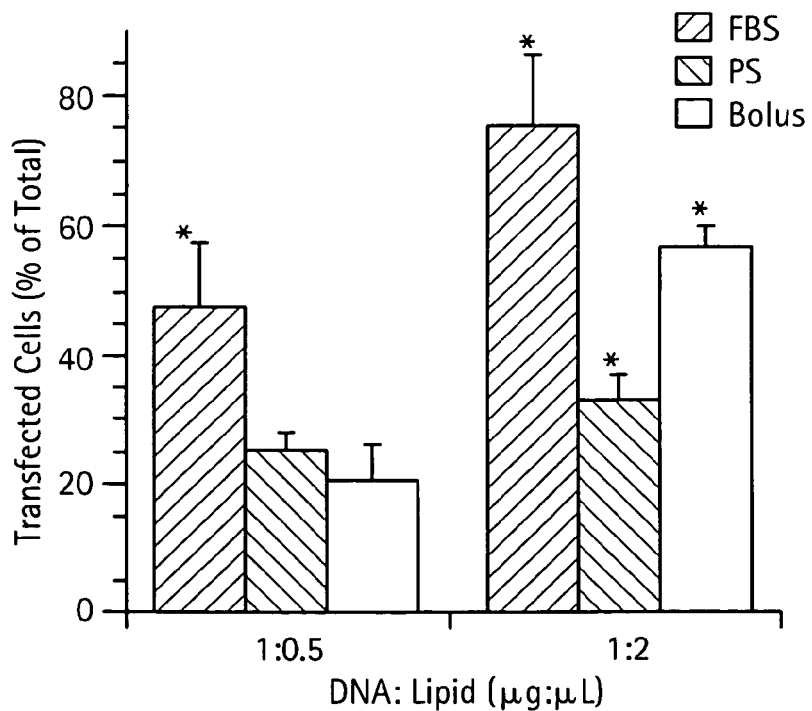

The similar levels of transgene expression obtained by lipoplex delivery from both PS and FBS-PS substrates were further examined by quantifying the percentage of transfected cells. The percentage of transfected cells was increased nearly 2-fold on FBS-PS relative to PS, independent of quantity immobilized and the lipoplex composition (FIG. 20A, B; p<0.05). Substrate-mediated delivery from FBS-PS resulted in similar or greater percentages of transfected cells relative to bolus delivery. Polyplexes delivered from FBS-PS surfaces also had greater percentages of cells transfected compared to PS surfaces; however, transfection efficiencies were low (<10%, data not shown).

Cell-Complex Interaction

Figure 21A:
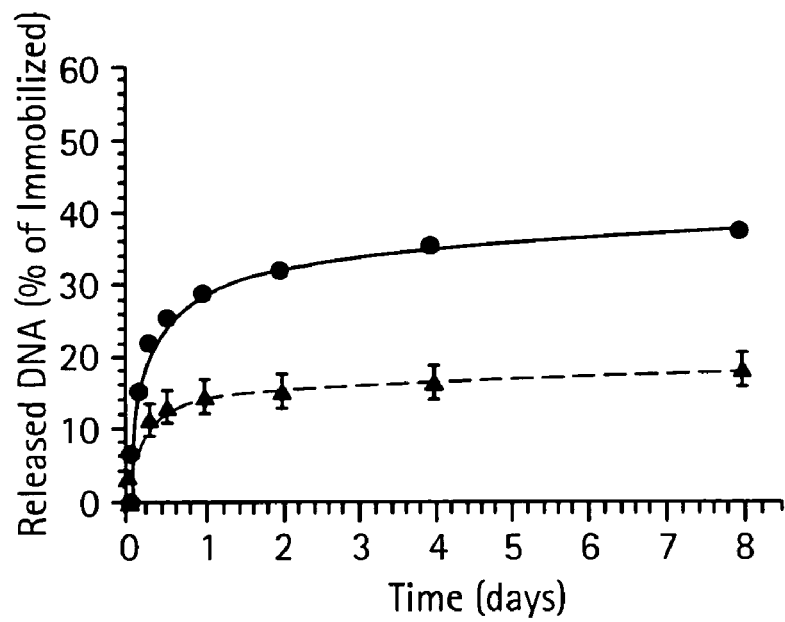
FIG. 21 shows release of adsorbed complexes upon exposure to conditioned media. Polyplexes (circles) and lipoplexes (triangles) (2 μg) were adsorbed to (A) PS and (B) FBS-PS substrates and exposed to conditioned media at 37° C. Data is presented as average ±standard deviation of the mean. Data points at 0.5 days and above are at $p<0.05$ relative to delivery with the other vector at each time point for each surface.
Figure 21B:
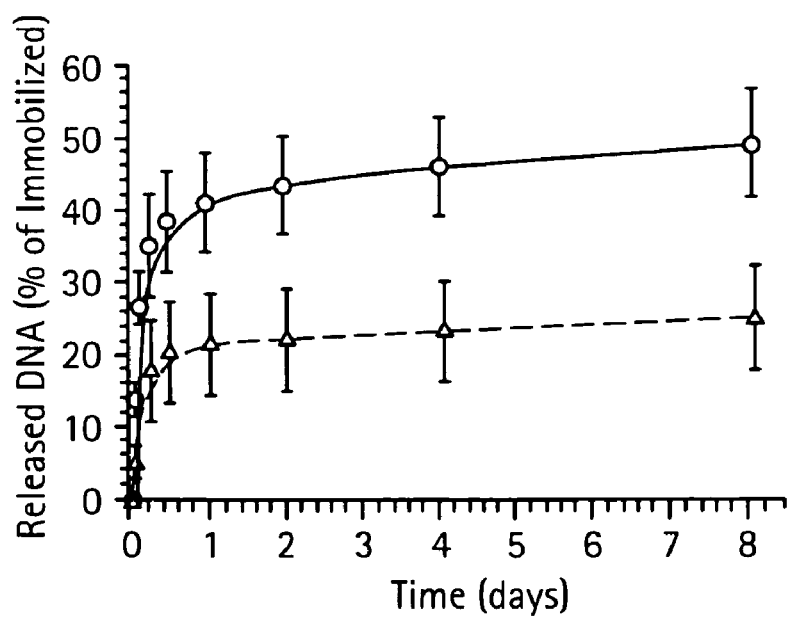

The ability of cells to promote release of complexes from the substrate for subsequent internalization was examined by performing release studies with conditioned growth media. In conditioned media, the release of DNA complexes was greater with FBS-PS surfaces compared with PS (FIG. 21A). After 8 days, 35% of polyplexes were released from PS surfaces and 47% were released from FBS-PS surfaces in conditioned media. These numbers are significantly greater than release studies in PBS (FIG. 17B). Lipoplexes exhibited similar dependence on serum coating, with 23% and 15% released from FBS-PS and PS substrates, respectively. This quantity released in conditioned media is consistent with amount released in PBS, with the primary difference being that maximal release was reached sooner in conditioned media. The differences in transfection observed between PS and FBS-PS were subsequently examined using confocal microscopy to determine the relative distribution of polyplexes and cells on the substrate. Conditions with relatively low (PS) and high (FBS-PS) transfection were compared to identify differences in the complex distribution, (N/P 25, 2 μg incubated on the surface). Polyplexes immobilized to PS, which had low transfection were distributed across the surface, with a fraction of the complexes associated with cells (FIG. 22A). For cells seeded onto DNA adsorbed FBS-PS substrates that yielded higher transfection, polyplexes were not distributed across the substrate, but were localized to the cells or their vicinity. Thus, polyplexes had a higher cellular association when delivered from serum-modified surfaces than compared to unmodified surfaces.

Primary Cell Transfection

The ability of substrate-mediated delivery to transfect primary cells was assessed using human dermal fibroblasts, a cell that has been difficult to transfect due to cytotoxicity. Polyplexes delivered as a bolus resulted in large amounts of cellular debris, poor cell morphology and reduced cellular viability (FIG. 23A). For substrate-mediated delivery, the fibroblasts had a morphology similar to that observed during typical cell culture (FIG. 23B). Transgene expression was greatest for fibroblasts cultured on FBS-PS, with both immobilized polyplexes and lipoplexes (FIG. 23C, 23D). Polyplexes delivered from a FBS-PS surface yielded 10.7 fold greater luciferase expression when compared to PS, with bolus delivery producing luciferase activity similar to FBS-PS. Lower doses of complexes delivered as a bolus resulted in insignificant luciferase activity (data not shown). Consistent with the NIH/3T3 culture, lipoplex delivery by substrate immobilization resulted in similar expression levels independent of surface modification (FBS-PS, PS) and the lipid content. Additionally, transgene expression for polyplexes and lipoplexes were similar; however, the percentage of transfected cells using lipoplexes was approximately 26%, whereas polyplex immobilization resulted in less than 5% of the cells transfected.

Transfection from a Biomaterial Scaffold

Figure 24:
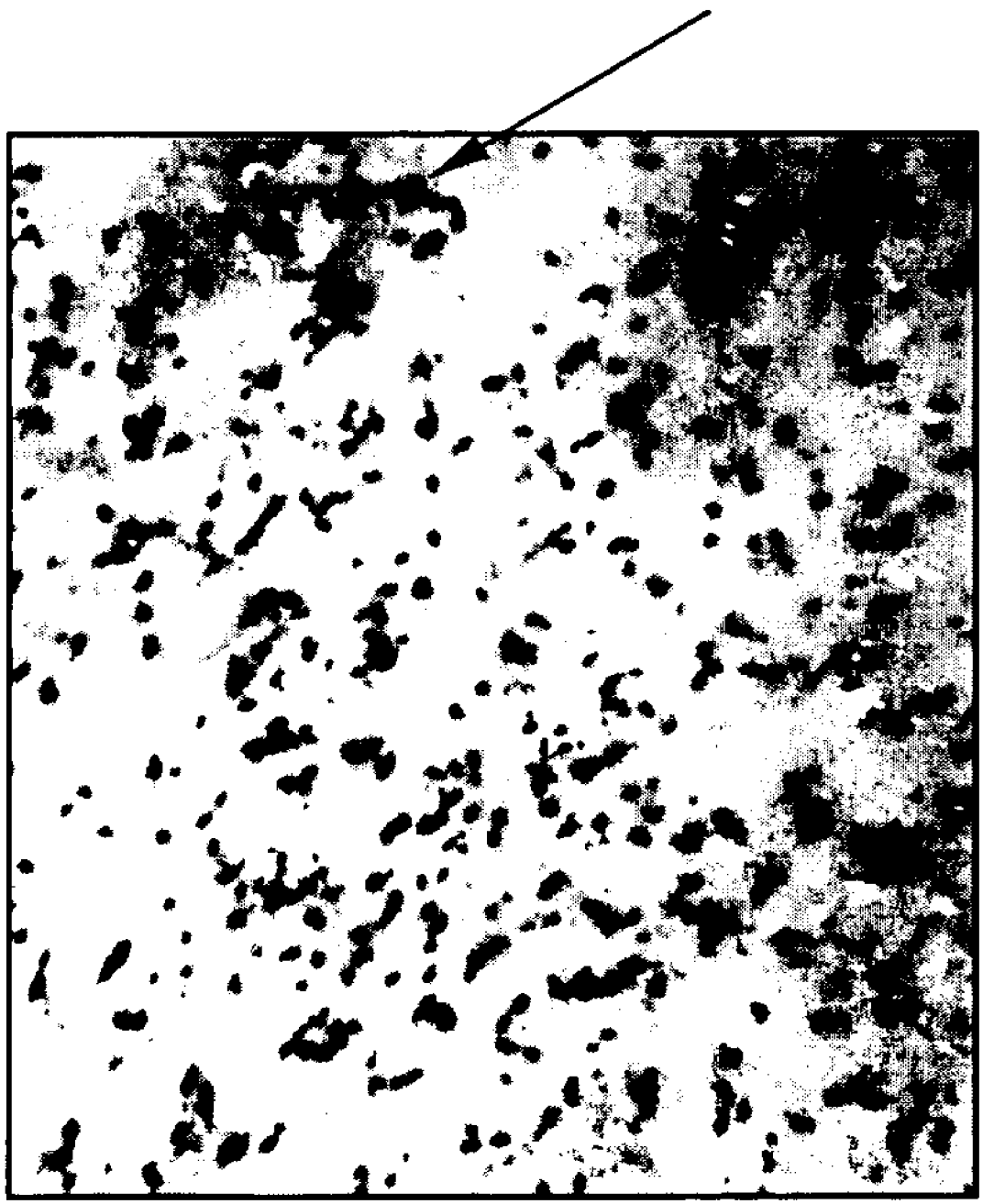
FIG. 24 shows substrate-mediated transfection from serum coated PLG. Polyplexes (5 μg) containing plasmid encoding for β-galactosidase were incubated for 24 hours. Transfected cells appear blue, as indicated with the arrow.

Substrate-mediated gene delivery can be applied to substrates other than PS, which may expand the applications of this delivery mechanism. Poly(lactide-co-glycolide) (PLG) disks were incubated with polyplexes, resulting in the immobilization of 1.3 μg/cm2. Transfected cells were visible across the substrate (FIG. 24A), and transgene expression was measured at $1.3 \times 10^5$ RLU/5000 cells seeded. These results demonstrate the potential to apply substrate-mediated delivery to alternative substrates other than PS, including biomaterials used in biomedical applications such as tissue engineering.

Summary of Example 5

Polyplexes immobilized to FBS-PS provided greater transfection than polyplexes immobilized to PS, and equivalent or greater transfection than bolus delivery of complexes. Lipoplexes, however, provide similar levels of transgene expression on serum coated and uncoated surfaces. Interestingly, transfection on serum coated surfaces increases the number of transfected cells relative to uncoated surfaces. Immobilized complexes are able to transfect primary cells, and result in lower cytotoxicity relative to bolus delivery. Finally, this delivery mechanism can be adapted to biomaterial surfaces, such as PLG, which is commonly used for biomedical applications such as tissue engineering.

Example 6

DNA Delivery from Hyaluronic Acid-Collagen

Materials and Methods

Sodium hyaluronan (HA) was a gift from Genzyme Corporation (1330 kDa, Cambridge, Mass.). The crosslinker poly(ethylene glycol) diglycidyl ether (CH2OCH-(CH2CH2O)n-CHOCH2, PEGDG, n=200) was purchased from Polysciences (Warrington, Pa.). Adipic acid dihydrazide (AAD), N-(3-dimethylpropyl)-N-ethylcarbodiimide hydrochloride (EDC) and N-hydroxysulfosuccinimide sodium salt (sulfo-NHS) were purchased from Sigma (St Louis, Mo.). Collagen was isolated from rat tails according to the procedure described by Choe et al. (Choe M M, Sporn P H, Swartz M A., Am J Physiol Lung Cell Mol Physiol, 2003;285(2):L427). Plasmid DNA encoding for luciferase or green fluorescent protein was purified from bacteria culture using Qiagen (Santa Clara, Calif.) reagents and stored in Tris-EDTA buffer solution (pH=7.4). Linear PEI, biotinylated linear PEI (PEI-Biotin), and arginine—glycine-aspartic acid modified linear PEI (RGD-PEI) were purchased from PolyTransfection (7 mm amine content, Strasbourg, France). Neutravidin (NA) and biotin reagents for HA modification were purchased from Pierce (Rockford, Ill.). All other reagents were obtained from Fisher Scientific (Fairlawn, N.J.) unless otherwise noted.

Synthesis of Biotinylated-Hyaluronic Acid

HA was biotinylated by first modifying its backbone with adipic acid dihydrazide (AAD) and then reacting the pendant hydrazide groups with sulfo-NHS-Lcbiotin (NHS-Biotin) (Segura T, Anderson B C, Chung P H, Webber R E, Shull K R, Shea L D. Crosslinked hyaluronic acid hydrogels: a strategy to functionalize and pattern. Biomaterials 2004; in press). Briefly, EDC (0.5 equivalents) and sulfo-NHS (0.5 equivalents) were added as solids to the HA solution (10 mg/ml), followed by AAD (30 equivalents) addition. The reaction proceeded at room temperature for 16 h with mixing. HA-AAD was precipitated and washed in cold ethanol. The precipitate was stored at 4° C. until use. Biotin was introduced to HA-AAD (HA-Biotin) using NHS-Biotin. NHS-Biotin (100 mg) was added as a solid to HA-AAD (300 mg, 3 mg/ml in PBS, pH 7.4). The reaction proceeded for 16 h at room temperature with stirring, and the product was purified by ethanol precipitation.

Hyaluronic Acid/Collagen Hydrogel Synthesis

HA-collagen hydrogels were formed using the reaction of the alcohols of biotinylated HA with the PEGDG crosslinker as previously described (Segura T, Anderson B C, Chung P H, Webber R E, Shull K R, Shea L D., Biomaterials 2004; in press). The hydrogels were formed with a final collagen concentration of 0.19 mg/ml. A topographical pattern was introduced into the hydrogel using a pattern transfer method. NA was bound by hydration of the hydrogel in a 1 mm NA solution in PBS for 1 h, followed by PBS wash.

Size and Zeta Potential Measurements

Size and zeta potential of DNA/PEI complexes were measured using a Zetasizer Nano Z S instrument (Malvern, Worcestershire, UK). For complexation, DNA (50 ml, 40 mg/ml) was mixed with PEI at nitrogen to phosphate (N/P) ratios ranging from 2.5 to 20. Complexes were formed in either water or 150 mm NaCl in a volume of 100 ml. After a 10-min incubation, complexes were diluted 10 times with either water or 150 mm NaCl. To examine complex aggregation, complexes were formed in water and diluted 10 times with 150 mm NaCl, with size monitored over time.

DNA/PEI Complex Immobilization

DNA complexes were immobilized to HA-collagen hydrogels by incubation of complexes with the NA bound HA-collagen hydrogel. DNA (50 ml of 40 mg/ml in 150 mm NaCl or water) was complexed with PEI (50 ml of 150 mm NaCl or water) at a N/P ratio of 5. Mixing biotinylated and non-biotinylated PEI prior to mixing with DNA varied the degree of biotinylation for the complex. The complexes were incubated for 10 min, transferred to NA bound HA-collagen surfaces, and incubated for 2 h at room temperature. The unbound complexes were removed and the surfaces were washed extensively with PBS buffer. Surface binding of the DNA/PEI complexes was examined using labeled DNA. Plasmid DNA was radiolabeled with a-32P dATP using a nick translation kit (Amersham Pharmacia Biotech, Piscataway, N.Y.) (Segura T, Volk M J, Shea L D., J Control Release 2003;93(1):69–84). 32P-DNA/PEI complexes were formed and immobilized to the surface using the described procedures. Following immobilization, the hydrogels were placed in scintillation cocktail (5 ml, ScintiVerse II) and radioactivity measured with a scintillation counter. The measured activity was correlated to DNA mass with a standard curve. For visualization of immobilized DNA/PEI complexes, DNA was labeled with tetramethyl rhodamine using a commercially available kit (label IT TMRhodamine, Mirus, Madison, Wis.). Images of the complexes on HA after extensive washing with PBS buffer were captured using a fluorescence microscope (Leica, Bannockburn, Ill.) equipped with a digital camera.

DNA/Cationic Polymer Release

The percentage of DNA/PEI complexes released from the hydrogel was determined using $^{32}$P-DNA complexes immobilized to NA bound HA-collagen hydrogels. After washing the hydrogels, PBS (pH 7.4), conditioned media (DMEM with 10% FBS from 2-day NIH/3T3 culture) or hyaluronidase (HAase, 100 U/ml) was added (200 ml) and the surfaces were incubated at 37° C. in a humid chamber. The HAase concentration was chosen to obtain significant hydrogel degradation during the 8-day study. At predetermined time-points, solution (100 ml) was removed with replacement, to minimize hydrogel disruption. The activity of the collected sample was measured in a scintillation counter, with the hydrogel also measured at the final time point. The percentage of DNA released was calculated by dividing the amount released at a given time-point by the initial amount immobilized.

Cell Culture and Transfection

All transfection studies were performed using an N/P ratio of 5 with complexes formed in either 150 mm NaCl or water. NIH/3T3 cells, a fibroblast cell line, were used to simulate in vivo delivery to fibroblasts (Bonadio J, Smiley E, Patil P, Goldstein S., Nat Med 1999;5 (7):753–9). Cells were plated (10,000 cells/well) on the modified hydrogel substrates and cultured for 2 days at 37° C. and 5% $CO_2$ in DMEM (Invitrogen, Gaithersburg, Md.) supplemented with 10% heat-inactivated FBS and 1% penicillin/streptomycin. The ability of complexes released from the hydrogel to promote gene transfer was examined by placing the hydrogels in culture above NIH/3T3 cells (15,000 cells/well) in 48-well plates. The DNA-modified hydrogels were not in direct contact with the adhered cells. Additionally, cellular interactions with the immobilized DNA complex was investigated through incorporation of an RGD peptide into the complex, which increase cellular interactions with the complex through integrin receptor binding to RGD (Kunath K, Merdan T, Hegener O, Haberlein H, Kissel T., J Gene Med 2003;5(7):588–99). Complexes were formed with a constant amount of PEIBiotin (25%) and varying amounts of RGD-PEI (10–75%). The extent of transgene expression elicited by the DNA-modified surfaces was examined using the reporter genes luciferase. For measurements of luciferase activity, the cells were lysed and assayed for luciferase enzymatic activity (Promega, Madison, Wis.). The luminometer was set for a 3-s delay and an integration of the signal for 10 s. Transgene expression of luciferase is reported as RLU per number of cells seeded. The number and distribution of transfected cells was determined with green fluorescent protein (GFP) expression and fluorescence microscopy. Complexes with 25% biotinylated PEI were immobilized onto the hydrogel surface. NIH/3T3 cells (7000 cells/well) were plated on topographically patterned-DNA modified hydrogels and cultured for 48 h. The cytoskeleton and nucleus of cells were stained with rhodamine phalloidin (1 U/200 ml) and Hoechst (1 mg/ml) stains, respectively (Molecular Probes, Eugene, Oreg.). Five pictures per triplicate were taken with a fluorescence microscope and analyzed. The percentage of transfected cells was calculated as the ratio of GFP-positive cells to total number of nuclei (Hoechst).

Results

DNA/PEI Complex Characterization

Figure 25A:
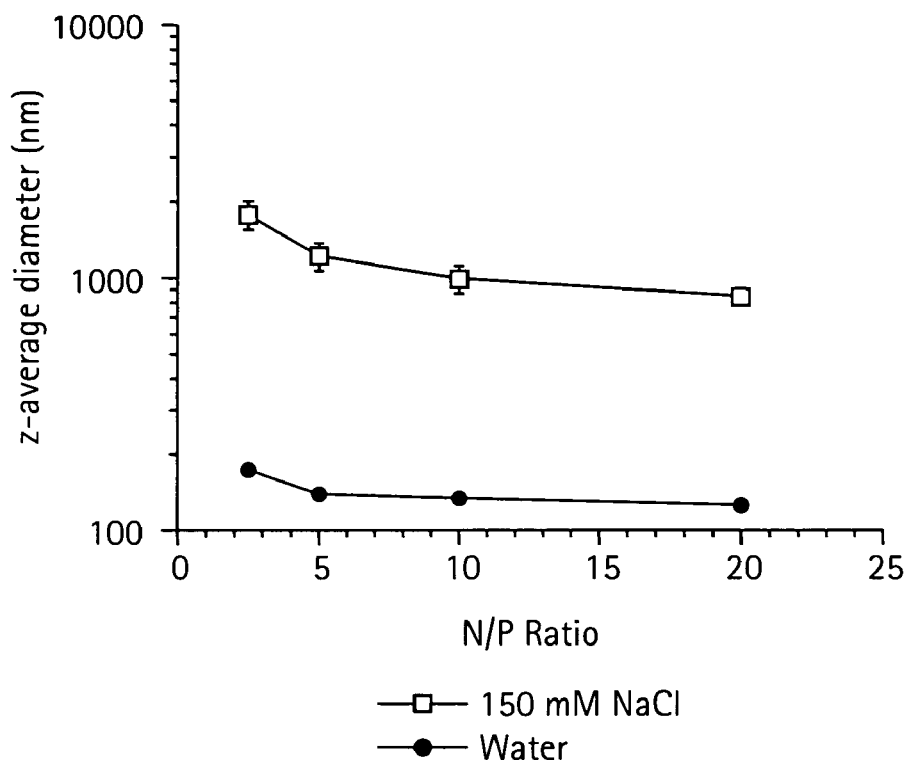
FIG. 25 shows (A) z-average diameter of DNA/PEI complexes at N/P ratios of 2.5, 5, 10 and 20 for complexes formed in 150 mm NaCl or water. (B) Zeta potential of DNA/PEI complexes at N/P ratios of 2.5, 5, 10 and 20 for complexes formed in 150 mm NaCl. Plotted data is an average of triplicate conditions.
Figure 25B:
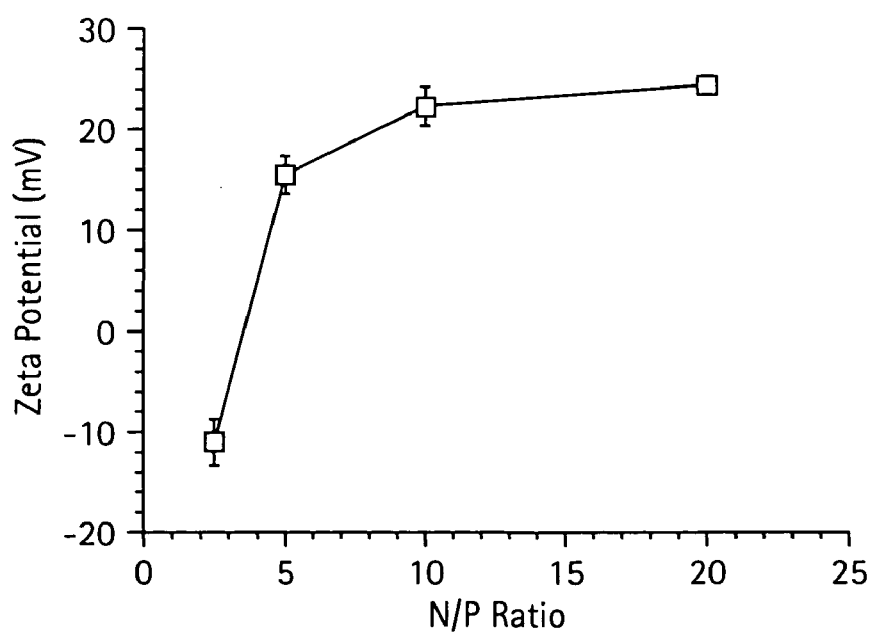

The dependence of the z-average diameter (dz) for the DNA complexes was determined at two salt concentrations (150 mm NaCl, pure water) and varying N/P ratio. dz for PEI/DNA complexes was an order of magnitude larger in the presence of salt (FIG. 25A). At an N/P ratio of 5, dz was equal to 139.4+/−1.3 nm in water, and 1221.7+/−152.3 nm in 150 mm NaCl. Additionally, complex diameter decreased with increasing N/P ratio in both 150 mm NaCl and water (FIG. 25A). For 150 mm NaCl, dz ranged from 848.9+/−63.6 nm (N/P 20) to 1778+/−227.7 nm (N/P 2.5). In water, dz ranged from 125.6+/−2.3 nm (N/P 20) to 173.9+/−2.2 nm (N/P 2.5). The zeta potential of complexes in 150 mm NaCl also increased with increasing N/P ratio with values ranging from −11.0+/−2.3 mV to 24.4+/−0.6 mV for complexes formed with 2.5 and 20 N/P ratios, respectively (FIG. 25B).

Figure 26:
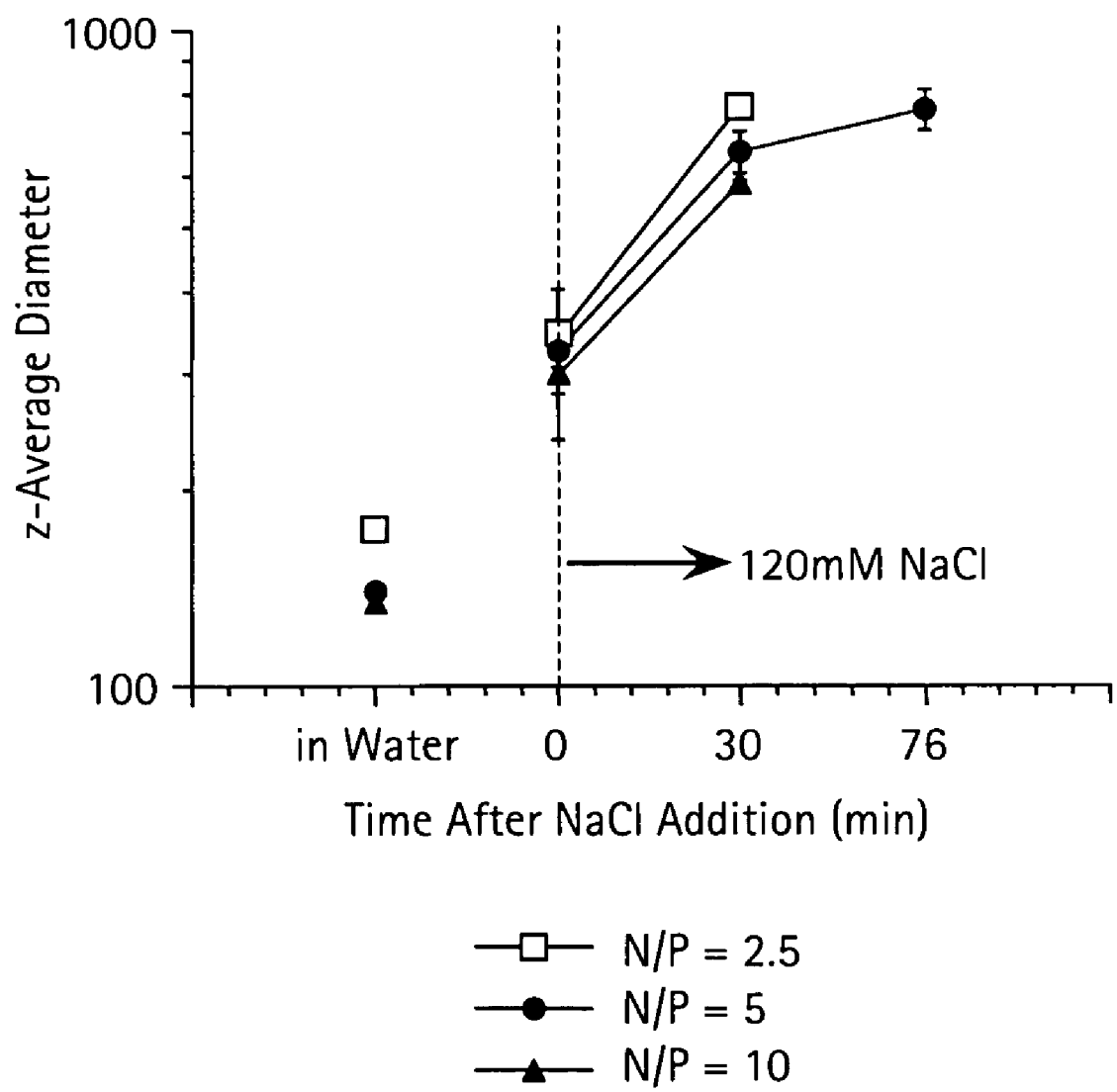
FIG. 26 shows DNA/PEI complex aggregation. Complexes were formed in water at different N/P ratios and complex size was monitored following addition of salt to the complexes. Plotted data is an average of triplicate conditions.

Complexes formed in the absence of salt aggregated upon addition of salt. The dz was monitored before and after salt addition for a total time of 76 min (FIG. 26). The complexes increased in size upon salt addition, with dz increasing from 139.7+/−1.3 nm to 342.7+/−12.8 nm immediately after salt addition for an N/P ratio of 5. PEI/DNA complex dz increased further with increased incubation time, reaching 758.7+/−53.8 nm after 76 min of incubation. This trend of increasing complex diameter with salt and time was observed for all N/P ratios (FIG. 26).

Surface Immobilization

DNA immobilization to the hydrogel was independent of salt content during complex formation and the extent of biotinylation. Quantities immobilized to the hydrogels ranged from 0.411+/−0.042 to 0.484+/−0.014 mg DNA, with no significant difference between conditions ($p>0.05$; FIG. 27A). Immobilization preserved the complex size that was observed in solution. Complexes formed in salt and deposited on the surface were visualized as discrete particles on the surface (FIG. 27B). Conversely, complexes formed in water resulted in more diffuse fluorescence without large aggregates, consistent with small particle deposition (FIG. 27C).

Cellular Transfection

Figure 28A:
FIG. 28 shows spatially controlled gene transfer of NIH/3T3 cells plated on topographically patterned HA-collagen-NA hydrogels with immobilized DNA/PEI complexes. Overlay of GFP positive cells and rhodamine phalloidin staining are shown. Magnifications correspond to 100×(A) and 200×(B).
Figure 28B:

Complexes with plasmid encoding for GFP were immobilized to the topographically patterned hydrogel substrates in order to visualize the distribution of transfected cells. NIH/3T3 cells plated and cultured on HA-collagen hydrogels oriented consistently with the pattern on the hydrogel surface. Visualization of the cytoskeleton (phalloidin) by fluorescence microscopy demonstrated that the cells were aligned with the pattern. Additionally, NIH/3T3 cells cultured on the DNA-modified hydrogel substrates were found to express the transgene in this oriented conformation (FIG. 28).

Figure 29:
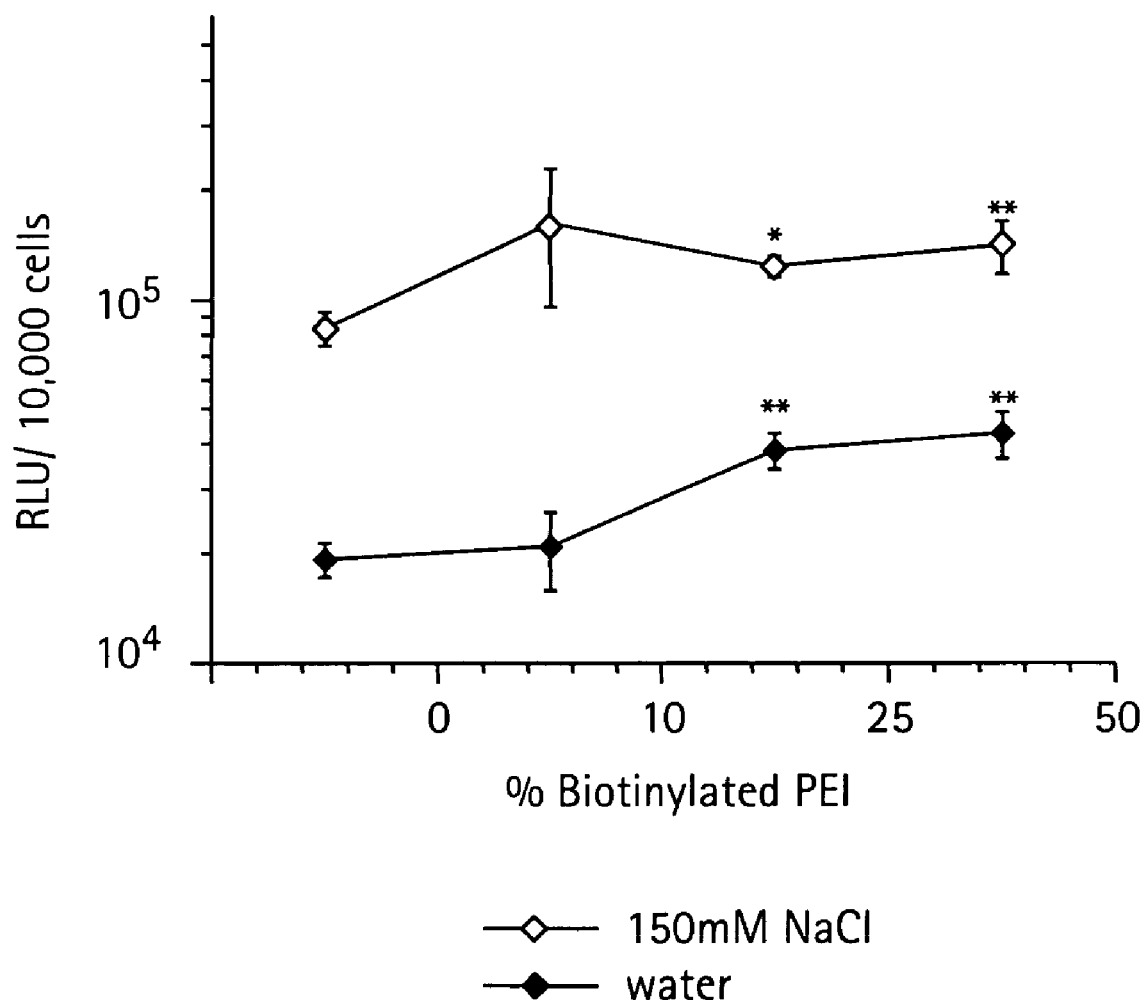
FIG. 29 shows transgene expression in NIH/3T3 cells mediated by immobilized complexes to HA-collagen-NA substrates. % biotinylated PEI indicate the percent biotinylation of the complexes. The symbols * and ** represents a statistically significant level of $p<0.05$ and $<0.01$; respectively, for single comparisons between biotinylated complexes and non-biotinylated complexes. Complexes were formed at an N/P ratio of 5. Plotted data is an average of triplicate conditions.
Figure 30A:
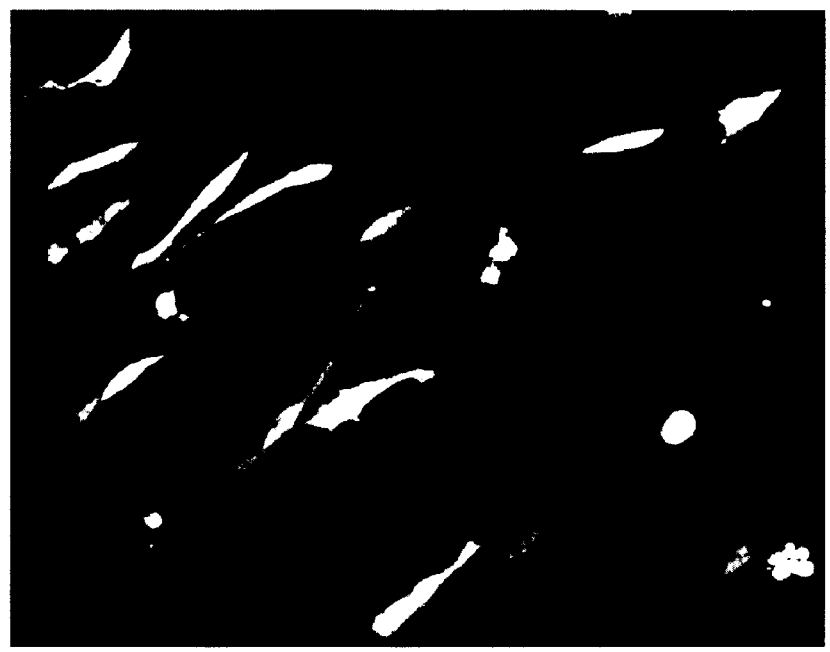
FIG. 30 shows GFP transgene expression in NIH/3T3 cells mediated by immobilized complexes to HA-collagen-NA substrates. The cell nuclei are stained with HOESCHT dye for visualization (A). The percentage of transfected cells was calculated by dividing the number of GFP positive cells by the total number of nuclei. The symbol *** represents a statistically significant level of $p<0.0001$ for a single comparison between large and small complexes. Complexes were formed at an N/P ratio of 5. Plotted data is an average of triplicate conditions.
Figure 30B:
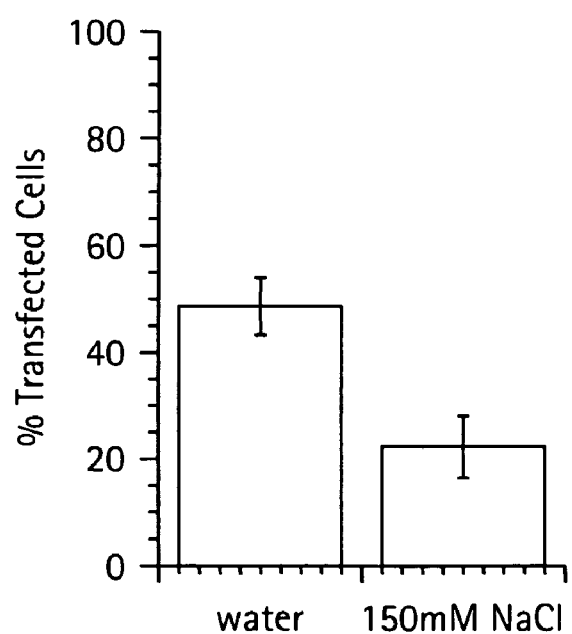

The role of complex size, which was regulated by salt content during complex formation, in gene transfer for substrate-mediated delivery was examined by measuring the extent of transgene expression and percentage of transfected cells. Complex size significantly affected transgene expression, with large diameter complexes (formed in NaCl) resulting in increased luciferase expression relative to small diameter complexes (formed in water, FIG. 29). Maximal transgene expression levels were $1.62+/−0.67\times10^5$ and $4.28+/−0.62\times10^4$ (RLU/10,000 cells) for the large and small-diameter complexes, respectively (FIG. 29). Furthermore, complexes formed with biotinylated PEI resulted in statistically higher luciferase expression than non-biotinylated complexes ($p<0.05$; FIG. 29). No difference in expression was observed for complexes formed with different extents of biotinylation ($p>0.05$). The percentage of transfected cells by the different complexes was subsequently examined to determine if increased luciferase production correlated with a higher percentage of transfected cells (FIG. 30A). However, small diameter complexes resulted in transfection of 48.7+/−5.4% of adhered cells, whereas large diameter complexes resulted in a transfection percentage of 22.3+/−5.8% (FIG. 30B).

Mechanism of DNA Internalization

Figure 31A:
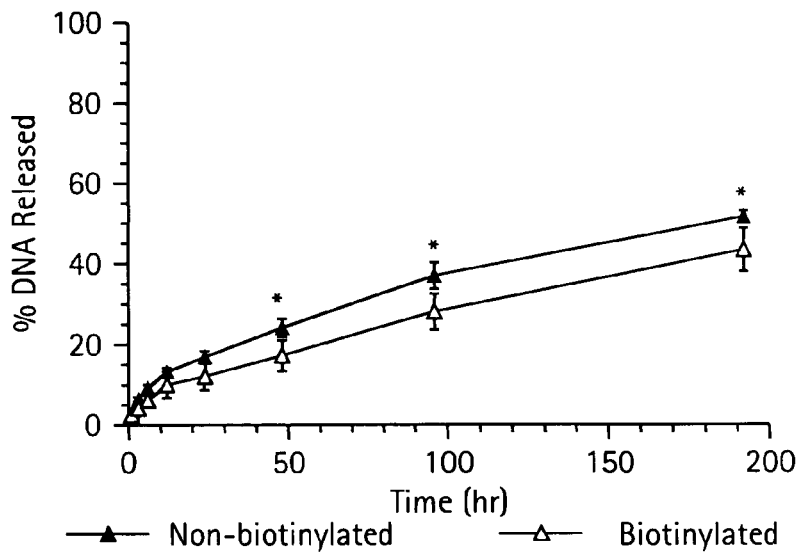
FIG. 31 shows release kinetics of biotinylated and non-biotinylated complexes immobilized to HA-collagen-NA hydrogels against PBS (A), conditioned media (B) or hyaluronidase (C). Complexes containing 0% and 25% biotinylated PEI were immobilized to the hydrogel substrates. The symbols * and *** represents a statistically significant level of $p<0.05$ and $<0.001$; respectively, for single comparisons between biotinylated complexes and non-biotinylated complexes. Plotted data is an average of triplicate conditions.
Figure 31B:
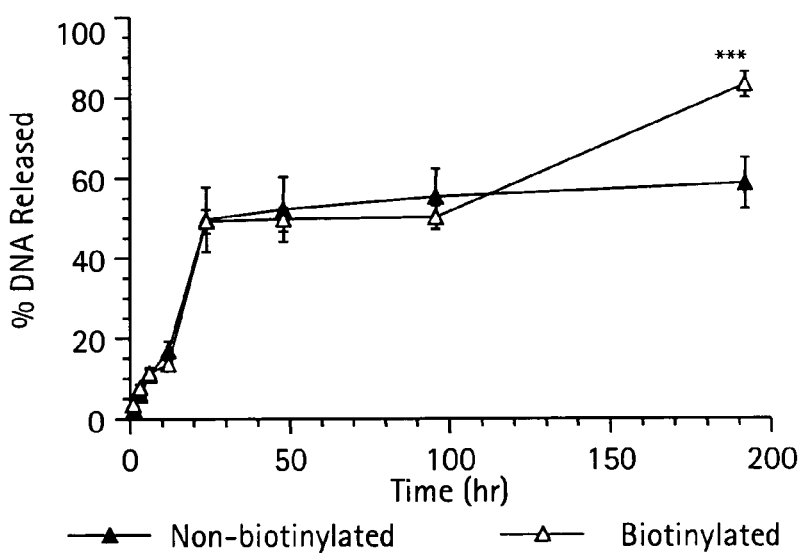
Figure 31C:
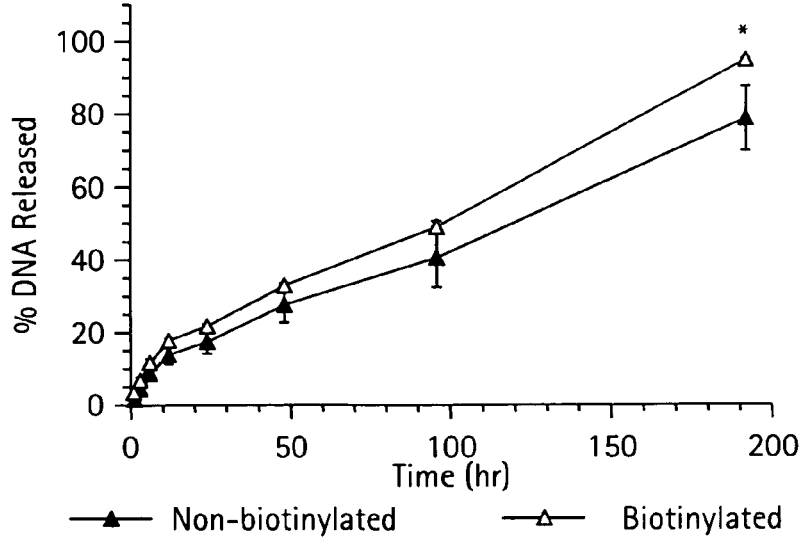

The mechanism of DNA internalization from the substrate was examined by examining release from the substrate, the ability of released complexes to transfect cells, and the role of speci.c cellular interactions with the complexes. Incubation of hydrogels with immobilized DNA complexes in PBS (FIG. 31A), conditioned media (FIG. 31B), and hyaluronidase (FIG. 31C) indicated that complexes were released from the substrate, with conditioned media producing the maximal release. After 24-h incubation, conditioned media induced release for approximately 50% of the immobilized DNA, which is substantially greater than release in either PBS or hyaluronidase. Release of biotinylated or non-biotinylated complexes was significantly different ($p<0.05$) primarily at the 8-day time point, with the greatest difference observed for release in conditioned media.

After 8-day incubation in PBS, conditioned media, and hyaluronidase, the percentage of non-biotinylated complexes released was 51.6+/−1.5, 58.7+/−6.4, and 78.6+/−8.8%, respectively. For biotinylated complexes, the percentage of released complexes was 43.4+/−5.3, 83.3+/−3.1, and 94.7+/−0.5% for substrates incubated in PBS, conditioned media, and hyaluronidase, respectively.

Incubation of DNA-immobilized hydrogels with NIH/3T3 cells cultured on tissue culture polystyrene was performed to assess the role of cellular adhesion to the substrate in gene transfer. Complexes released from the hydrogel did not efficiently transfect cells that were not cultured on the substrate (FIG. 32). Luciferase expression was ol RLU=10; 000 cells by incubation of hydrogels with cells cultured on polystyrene, which is significantly less than expression levels observed when cells were cultured on the hydrogel (>105RLU=10; 000 cells).

Figure 33:
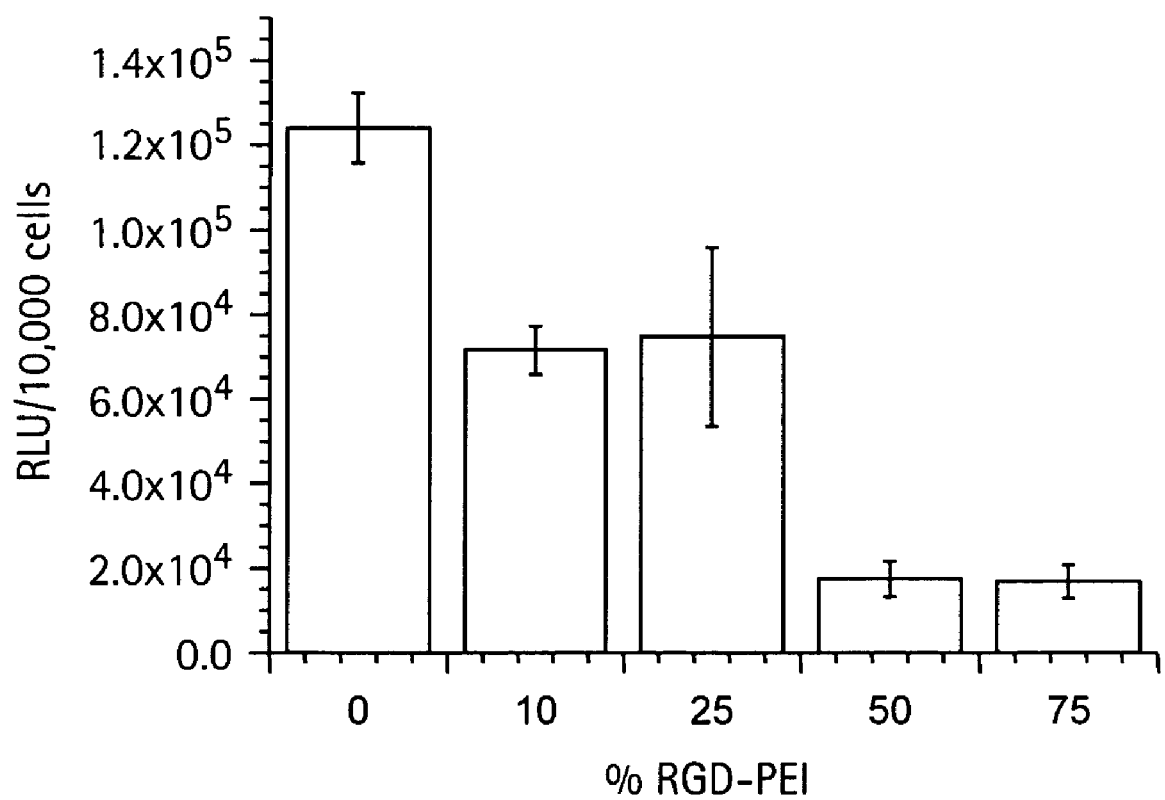
FIG. 33 shows luciferase transgene expression in NIH/3T3 cells mediated by immobilized complexes to HA-collagen-NA substrates. % RGD-PEI indicates the percent RGD modification of the complexes. DNA/PEI complexes were formed (N/P=5) with mixtures of three types of PEI: biotinylated, RGD-modified and unmodified. The percentage of biotinylated PEI was kept constant at 25% and the percentage of RGD-PEI was varied from 0% to 75% to obtain different quantities of RGD in the complex. Plotted data is an average of triplicate conditions.

Incorporation of RGD peptides into the DNA complexes, which was hypothesized to increase cellular interactions with the complexes through RGD binding to integrin receptors, resulted in lower transgene expression than unmodified complexes (FIG. 33). For all the conditions tested, the presence of RGD in the complex decreased transgene expression relative to the absence of RGD peptides. In the absence of RGD peptides, transgene expression was $1.24+/−0.08\times10^5$ RLU/10,000 cells. The presence of RGD at levels of 10% and 25% resulted in mean expression levels of approximately $7\times10^4$ RLU/10,000 cells. Further increases in PEI-RGD content to 50% and 75% reduced mean transgene expression to less than $2\times10^4$ RLU/10,000 cells.

Summary of Example 6

Complexes formed in the presence of salt had a z-average diameter equal to 1221.7+/−152.3 nm, while formation in water produced complexes with z-average diameter of 139.4+/−1.3 nm. Complexes immobilized to the hydrogel had sizes consistent with their size in solution, and did not aggregate. The quantity of complexes immobilized was independent of the complex size and the extent of biotinylation. DNA release from the hydrogel substrate was enhanced by incubation with conditioned media, with release at 48 h equal to 49.7+/−8.1% and 49.2+/−2.9% for non-biotinylated and biotinylated complexes, respectively. Transfection studies showed that transgene expression mediated by large complexes was 3- to 7-fold greater than with small complexes. However, the number of cells expressing the transgene was increased with small complexes (48.7%), relative to large complexes (22.3%). Finally, the hydrogel was patterned topographically, which guided and oriented cell attachment to the substrate and resulted in spatial patterns of transfected cells on the hydrogel.

In summary, efficient and controlled DNA delivery from biomaterial substrates has the potential to enhance the applicability of gene delivery to tissue engineering. We have fabricated hydrogels with the ability to transfect adherent cells using immobilized DNA complexes, which can be manipulated to alter the number of transfected cells and the extent of transgene expression. Additionally, these hydrogels can be patterned to regulate cell attachment and orient cell growth, which results in spatial patterns of transfected cells.

Example 7

Patterned Transfection on Gold Substrates

Figure 34:
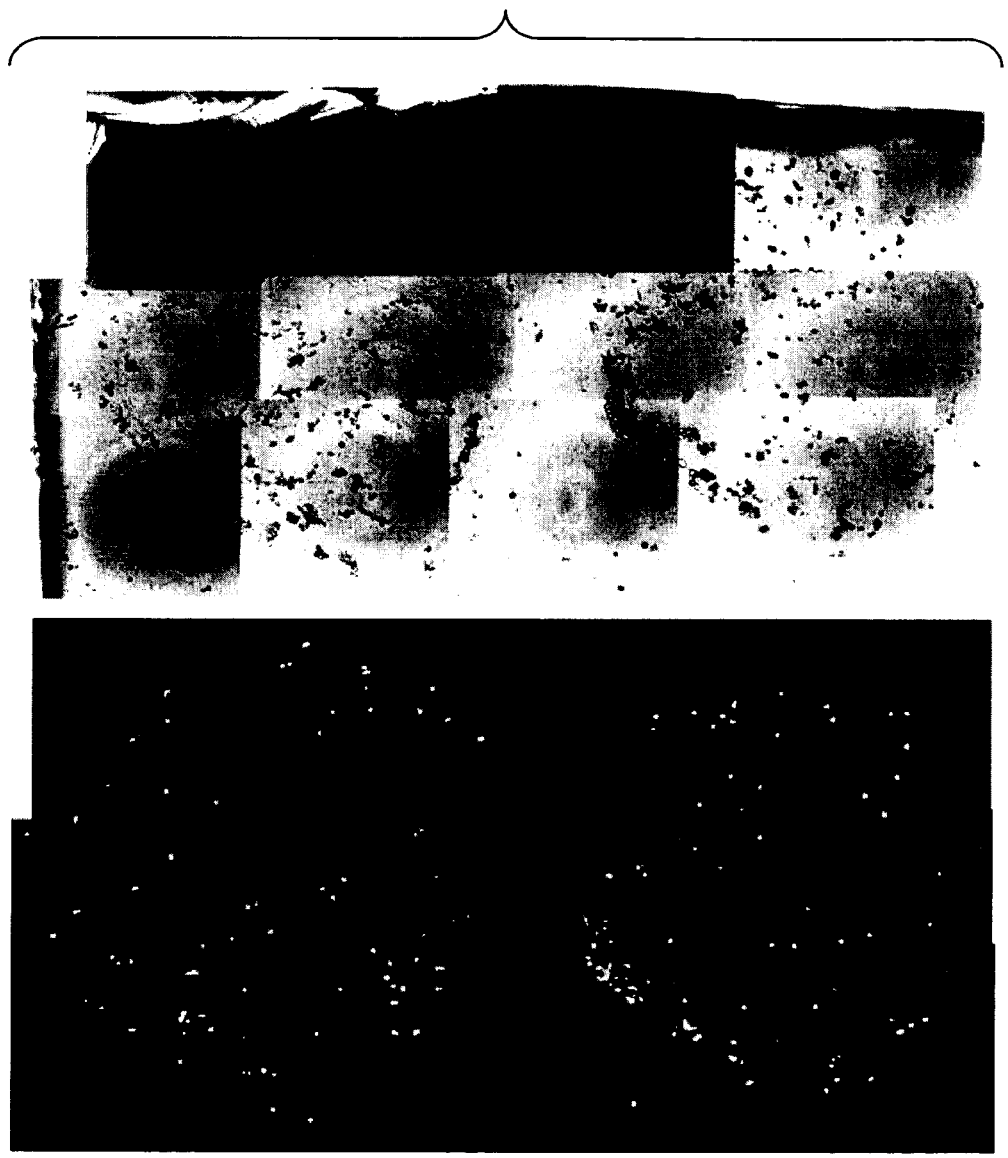
FIG. 34 shows photomicrographs of GFP expressing cells in patterns on gold surfaces. a) Overlay of GFP photomicrograph on phase photomicrograph. b) Photomicrograph of just GFP-expressing cells.
Figure 35:
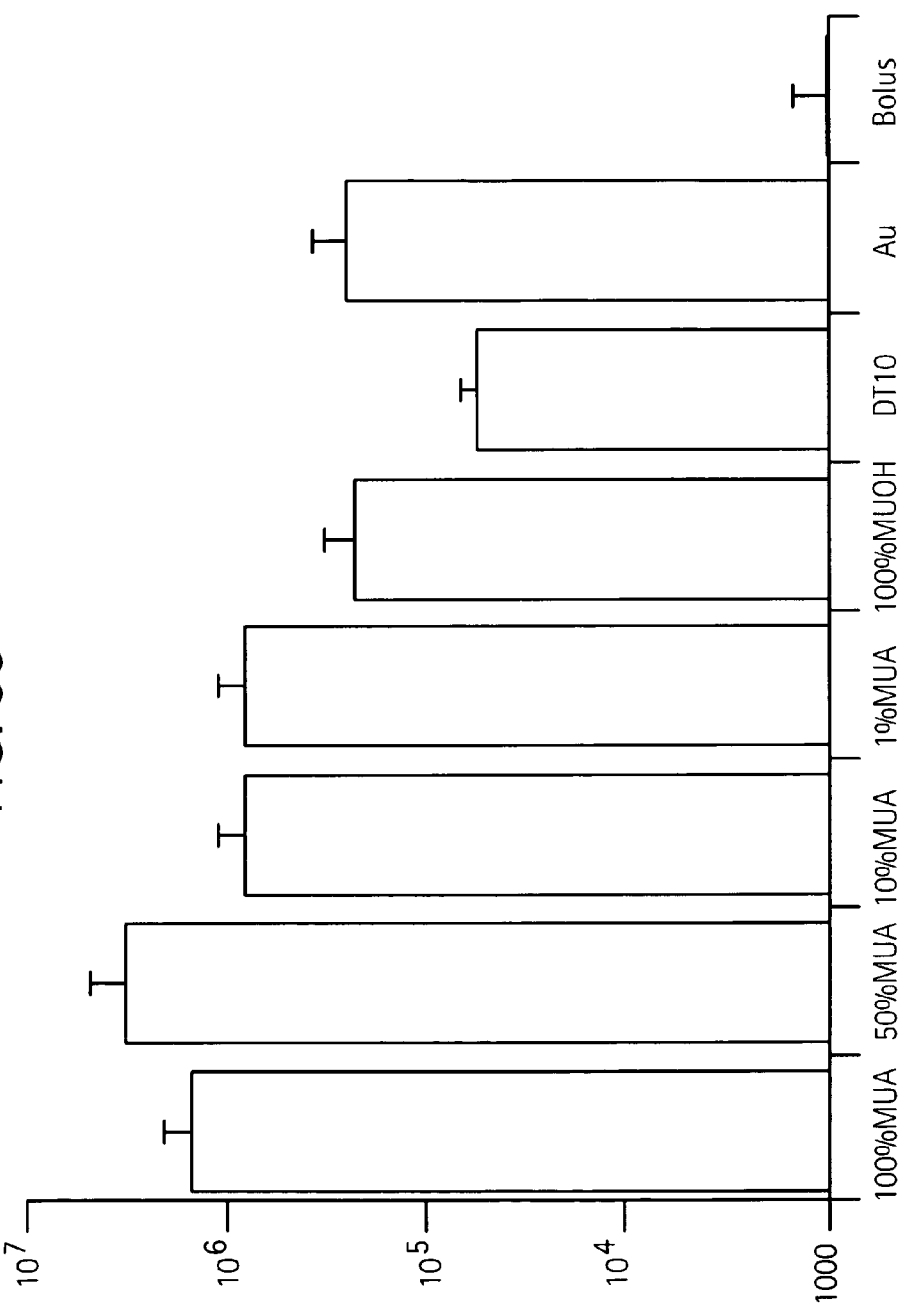
FIG. 35 shows luciferase transgene expression in NIH/3T3 cells mediated by immobilized complexes to alkanethiol modified gold surfaces. DNA was complexed with Lipofectamine, deposited onto gold for 2 hours, surfaces were washed and cells were then seeded. Luciferase expression was assayed for 24 hours later.

Self-assembled monolayers (SAMs) of alkanethiols on gold were used to spatially pattern surfaces with chemically active groups to regulate the location of DNA delivery from the surface (FIGS. 34 and 35). A self-assembled monolayer is a single layer of molecules on a substrate in which the molecules exhibit a high degree of orientation, molecular order, and packing. The monolayer spontaneously forms upon exposure of the substrate to an ethanol solution containing the molecules. Alkanethiols form well-packed and stable monolayers on gold through a thiolate linkage. A poly(dimethylsiloxane) (PDMS) stamp was used to imprint gold surfaces with specific patterns of SAMs of mercapto-1-undecanol (MUOH) or 11-mercaptoundecanoic acid (MUA) according to the method of Ulman, A. (1996). Formation and Structure of Self-Assembled Monolayers. Chem Rev 96, 1533–1554. The stamped surface was then immersed into a solution of 2 mM 1-decanethiol (DT10), creating regions with different properties allowing for physically distinct regions of complexes. Complexes were formed with a plasmid encoding for eGFP/Luciferase, complexed with Lipofectamine at a 1:2.5 DNA: Lipofectamine ratio. The complexes were then deposited on the surface for 2 hours. The surfaces were then washed and NIH/3T3 fibroblasts were seeded. Luciferase expression was assayed 24 hours later. Alternatively, cells were seeded onto the alkanethiol modified gold surface and DNA complexes were then added as a bolus.

As shown in FIG. 35, complexes adsorbed on the hydrophilic, charged MUA transfected with greater efficiency than complexes adsorbed on MUOH, DT10, or on the unmodified gold surface. Very little complex was transfected when DNA was delivered as a bolus.

The present invention is not to be limited in terms of the particular embodiments described in this application, which are intended as single illustrations of individual aspects of the invention. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. The contents of each reference, patent and patent application cited in this application is hereby incorporated by reference in its entirety.

TABLE 1

Contact Angle Measurements for Substrates (water)

| Surface | Contact Angle (deg) |
| --- | --- |
| Tissue Culture Polystyrene (PS) | 47.75 +/− 6.64 |
| FBS Modified Tissue Culture Polystyrene (FBS-PS) | 12.67 +/− 3.13 |

What is claimed is:

1. A method for increasing transgene expression, comprising making a controlled nucleic acid delivery system, said system comprising forming nucleic acid polylinker complexes capable of being delivered to cells cultured on a support substrate, wherein said complexes are formed prior to being covalently or non-covalently immobilized to the surface of a support substrate, and wherein said method comprises:
   a) contacting a nucleic acid with a polylinker to form a nucleic acid-polylinker complex, said complex being formed prior to attachment to a support substrate; and
   b) immobilizing the nucleic acid-polylinker complex to a support substrate; and
wherein said cells are added to the support substrate after immobilization of the nucleic acid-polylinker complex to the support substrate.

2. The method of claim 1, further comprising modification of the support substrate with serum prior to addition of the nucleic acid-polylinker complex, and wherein said modification allows for an increase in transgene expression.

3. The method of claim 1, wherein the extent of transgene expression is dependent upon substrate modification and complex formation.

4. The method of claim 1, wherein said nucleic acid polylinker complexes are polyplexes or lipoplexes.

5. The method of claim 1, wherein said support substrate is polystyrene, gold, hyaluronic acid collagen hydrogels or polylactide-co-glycolide (PLG).

6. The method of claim 2, wherein said substrate modification is made by treatment with serum.

7. The method of claim 1, wherein delivery of the nucleic acid-polylinker complexes to cells occurs from a polystyrene surface treated with serum, and wherein said delivery results in similar or greater percentage of transfected cells relative to bolus delivery.

8. The method of claim 1, said method further comprising release of the nucleic acid from the nucleic acid-polylinker complexes, wherein said release is maximized when the support substrate is treated with serum.

9. A method for increasing transgene expression, comprising making a controlled nucleic acid delivery system, said system comprising forming nucleic acid polylinker complexes capable of being delivered to cells cultured on a support substrate, wherein said complexes are covalently or non-covalently immobilized to the surface of a support substrate, and wherein said method comprises:
   a) contacting a nucleic acid with a polylinker to form a nucleic acid-polylinker complex;
   b) immobilizing the nucleic acid-polylinker complex to a support substrate; and
   c) adding cells to the support substrate after immobilization of the nucleic acid-polylinker complex to the support substrate,
wherein the release of nucleic acid from the nucleic acid-polylinker complexes is further enhanced when the support substrate containing the complexes is treated with serum or is incubated in conditioned medium.

10. The method of claim 2, wherein the delivery of the nucleic acid-polylinker complexes to cells from a serum-modified support substrate results in higher cellular association of the nucleic acid-polylinker complexes with the support substrate.

11. A method for increasing transgene expression, comprising the steps of:
   a) making a controlled nucleic acid delivery system by contacting a nucleic acid with a polylinker to form a nucleic acid-polylinker complex, wherein said complex is formed prior to addition to a support substrate;
   b) immobilizing the nucleic acid-polylinker complex to a support substrate; wherein said immobilizing is accomplished by covalent or non-covalent means, and
   c) adding the cells into which transgene expression is desired to the support substrate after immobilization of the nucleic acid-polylinker complex to the support substrate.

12. The method of claim 11, wherein said support substrate comprises a biodegradable or non-biodegradable material.

13. The method of either one of claim 1 or 11, wherein said complexes are formed prior to attachment to the solid support substrate.

14. The method of claim 12, wherein said biodegradable material is a hydrogel and said non-biodegradable material is polystyrene or gold.

15. The method of claim 12, wherein said hydrogel comprises a mixture of hyaluronic acid and collagen.

16. A method for increasing transgene expression, wherein said method promotes transfection of primary cells, comprising the steps of:
   a) making a controlled nucleic acid delivery system by contacting a nucleic acid with a polylinker to form a nucleic acid-polylinker complex;
   b) immobilizing the nucleic acid-polylinker complex to a support substrate; wherein said immobilizing is accomplished by covalent or non-covalent means, and
   c) adding the cells into which transgene expression is desired to the support substrate after immobilization of the nucleic acid-polylinker complex to the support substrate, wherein the biodegradable material is a hydrogel and the non-biodegradable material is polystyrene or gold, and wherein the hydrogel comprises a mixture of hyaluronic acid and collagen.

17. The method of either one of claim 1 or 11, wherein said nucleic acid polylinker complexes are immobilized to the support substrate using biotin and avidin, or an avidin derivative, or by non-specific adsorption.

18. The method of claim 17, wherein said avidin derivative is streptavidin or neutravidin.

19. The method of any one of claim 11–15, wherein the method further comprises controlling the size of the nucleic acid polylinker complex by regulating the salt content during complex formation.

20. The method of claim 19, wherein controlling the size of said complex formation is accomplished by the presence or absence of salt during the formation of the complexes, wherein the forming of large diameter complexes in the presence of salt results in increased transgene expression, and wherein the forming of small diameter complexes in the absence of salt results in a greater percentage of cells being transfected.

21. The method of claim 19, wherein the salt is sodium chloride.

22. A method for increasing transgene expression, comprising the steps of:
   a) making a controlled nucleic acid delivery system by contacting a nucleic acid with a polylinker to form a nucleic acid-polylinker complex;
   b) immobilizing the nucleic acid-polylinker complex to a support substrate; wherein said immobilizing is accomplished by covalent or non-covalent means, and
   c) adding the cells into which transgene expression is desired to the support substrate after immobilization of the nucleic acid-polylinker complex to the support substrate,
wherein said method further comprises release of the nucleic acid from the substrate, wherein the release is optimized by using conditioned medium.

23. The method of claim 11, wherein said method further comprises biotinylation of said complex to enhance release of said complex from said substrate.

24. The method of either of claim 1 or 11, wherein the nucleic acid is DNA, RNA or an oligonucleotide.

25. The method of claim 24, wherein said oligonucleotide is an antisense oligonucleotide or a catalytic RNA capable of interfering with the expression of a gene.

26. The controlled nucleic acid delivery system of either of claim 1 or 11, wherein the polylinker is a cationic polymer, cationic lipid, cationic protein, or cationic peptide.

* * * * *